United States Patent
Scheidereit et al.

(10) Patent No.: US 11,028,084 B2
(45) Date of Patent: Jun. 8, 2021

(54) SELECTIVE INHIBITORS OF GENTOTOXIC STERESS-INDUCED IKK/NF-κB PATHWAYS

(71) Applicants: Max-Delbrück-Centrum für Molekulare Medizin in der Helmholtz-Gemeinschaft, Berlin (DE); Forschungsverbund Berlin e.V., Berlin (DE)

(72) Inventors: Claus Scheidereit, Berlin (DE); Michael Willenbrock, Berlin (DE); Peter Lindemann, Berlin (DE); Silke Radetzki, Berlin (DE); Jens-Peter Von Kries, Panketal (DE); Marc Nazare, Berlin (DE)

(73) Assignees: Max-Delbrück-Centrum für Molekulare Medizin in der Helmholtz-Gemeinschaft, Berlin (DE); Forschungsverbund Berlin e.V, Berlin (DE)

( * ) Notice: Subject to any disclaimer, the term of this patent is extended or adjusted under 35 U.S.C. 154(b) by 0 days.

(21) Appl. No.: 16/349,580

(22) PCT Filed: Nov. 14, 2017

(86) PCT No.: PCT/EP2017/079181
§ 371 (c)(1),
(2) Date: May 13, 2019

(87) PCT Pub. No.: WO2018/087389
PCT Pub. Date: May 17, 2018

(65) Prior Publication Data
US 2019/0276452 A1 Sep. 12, 2019

(30) Foreign Application Priority Data
Nov. 14, 2016 (EP) .................................. 16198731

(51) Int. Cl.
*C07D 471/04* (2006.01)
*A61P 35/00* (2006.01)
*C07D 209/56* (2006.01)
*C07D 221/06* (2006.01)
*C07D 471/14* (2006.01)
*C07D 487/04* (2006.01)
*C07D 471/16* (2006.01)

(52) U.S. Cl.
CPC ............ *C07D 471/04* (2013.01); *A61P 35/00* (2018.01); *C07D 209/56* (2013.01); *C07D 221/06* (2013.01); *C07D 471/14* (2013.01); *C07D 471/16* (2013.01); *C07D 487/04* (2013.01)

(58) Field of Classification Search
CPC .................................................. C07D 471/04
See application file for complete search history.

(56) References Cited

FOREIGN PATENT DOCUMENTS

| EP | 1 634 881 A1 | | 3/2006 |
|---|---|---|---|
| WO | WO2007/097981 | * | 8/2007 |
| WO | WO 2007/097981 A2 | | 8/2007 |
| WO | WO 2011/011186 A2 | | 1/2011 |

OTHER PUBLICATIONS

Almerico et al., J'nal of Mol. Graphics and Modelling. 42(2013) 60-72.*
Clemo et al., The Constitution of Yohimbine, Part. II, (1949)pp. 487-492.*
Mandour, Acta Pharm., 60 (2010) 73-88 Markgraf et al., Tetrahedron 61 (2005) pp. 6102-9100.*
McMahon et al. (2000) Pinedo et al. (2000).*
Almerico, A.M. et al. 2013 "A3 adenosine receptor: homology modeling and 3D-QSAR studies" *Journal of Molecular Graphics and Modelling* 42: 60-72.
Chen, Q. et al. 2004 "Antitumor and neurotoxic effects of novel harmine derivatives and structure-activity relationship analysis" *Int J Cancer* 114: 675-682.
Clemo, G. R. and Swan G.A. 1949 "The constitution of yohimbine. Part II" *J Chem Soc* 1949 pp. 487-492.
Du, H. et al. 2016 "Synthesis and biological evaluation of $N^9$-substituted harmine derivatives as potential anticancer agents" *Bioorganic & Medicinal Chemistry Letters* 26: 4015-4019.
Lamchouri, F. et al. "Quantitative structure activity relationship of antitumor and neurotoxic β-carbolines alkaloids: nine harmine derivatives" *Res Chem Intermed* 39: 2219-2236.
Hsu, M-J. et al. 2005 "Cell apoptosis induced by a synthetic carbazole compound LCY-2-CHO is mediated through activation of caspase and mitochondrial pathways" *Biochemical Pharmacology* 70: 102-112.
International Search Report in PCT/EP2017/079181, dated Jan. 16, 2018.
Lamkanfi, M. et al. 2006 "Caspases leave the beaten track: caspase-mediated activation of NF-kB" *The Journal of Cell Biology* 173: 165-171.
Lin, Y.-C. et al. 2016 "Synthesis and structure-activity relationship studies of novel 3,9-substituted a-carboline derivatives with high cytotoxic activity against colorectal cancer cells" *European Journal of Medicinal Chemistry* 110: 98-114.
Mandour, A.H. et al. 2010 "Synthesis, ant-inflammatory, analgesic and anticonvulsant activities of 1,8-dihydro-1-8-alkyl pyrazolo(3,4-b)indoles" *Acta Pharm* 60: 73-88.
Markgraf, J.H. et al. 2005 "A versatile route to benzocanthinones" *Tetrahedron* 61: 9102-9110.

(Continued)

*Primary Examiner* — Paul V Ward
(74) *Attorney, Agent, or Firm* — Knobbe, Martens, Olson & Bear, LLP

(57) ABSTRACT

A method is for treatment of a disease associated with genotoxic stress-induced inhibitor of nuclear factor-κB kinase/nuclear factor kappa-light chain enhancer of activated B cells (IKK/NF-κB) signaling. The method can include administering a compound to a subject having a cancer exhibiting genotoxic stress induced IKK/NF-κB activation.

19 Claims, 23 Drawing Sheets

(56) References Cited

OTHER PUBLICATIONS

Rocca, R. et al. 2016 "Hit identification of a novel dual binder for h-telo/c-myc G-quadruplex by a combination of pharmacophore structure-based virtual screening and docking refinement" *ChemMedChem* 11: 1721-1733.

Silva, C.M.B.L. et al. 2012 "Synthesis, antitumor, antitrypanosomal and antileishmanial activities of Benzo[4,5]cathin-6-ones bearing the N'(substituted benzylidene)-carbohydrazide and N-Alkylcarboxamide groups at C-2" *Chem Pharm Bull* 60(11): 1372-1379.

Zhang, Q. et al. 2013 "Synthesis and structure-activity relationships of $N^2$-alkylated quaternary b-carbolines as novel antitumor agents" *European Journal of Medicinal Chemistry* 65: 21-31.

Jin, Hyung-Seung, et al., "cIAP1, cIAP2, and XIAP Act Cooperatively via Nonredundant Pathways to Regulate Genotoxic Stress-Induced Nuclear Factor-kB Activation," Cancer Res 2009; 69: 1782-1791.

Willemann, C., et al., "Synthesis and cytotoxic activity of 5,6-heteroaromatically annulated pyridine-2,4-diamines," Bioorganic & Medicinal Chemistry (2009) 17: 4406-4419.

\* cited by examiner

A

B

C

D

A

B

A

B

A

B

C

A

MW01C1    MW01C2    MW01C3

MW01C4    MW01C5    MW01

B

C

D

*Variations of preferred ring C structures of Formulae I-VII*

*Variations at ring B:*

R6 = OMe; R7 = H, OMe
R6 = H; R7 = H, OMe

R6 = Me, R7 = H
R6 = H; R7 = Me whereby R5 and R8 are H

A

B

SELECTIVE INHIBITORS OF GENTOTOXIC STERESS-INDUCED IKK/NF-κB PATHWAYS

The invention relates to chemical compounds and their use as a medicament in the treatment of a disease associated with genotoxic stress-induced IKK/NF-κB (NF-kappaB) activation, preferably in the treatment of a subject suffering from cancer exhibiting genotoxic stress-induced IKK/NF-κB activation. The invention further relates to a pharmaceutical composition comprising a compound of the invention for the treatment of a subject afflicted by a disease associated with genotoxic stress-induced IKK/NF-κB activation.

BACKGROUND OF THE INVENTION

Adaptation to changes is crucial for survival of organisms. Environmental, chemical and physical as well as microbiological changes threaten normal tissue functions and cellular homeostasis and represent a source of stress for development and physiology. A major response to stress is cellular signaling exerting an impact on cellular functions by altering gene expression programs. The NF-κB (nuclear factor kappa-light-chain-enhancer of activated B-cells) system is a major player of cellular responses to stress. NF-κB is a widespread and rapidly inducible transcription factor (TF). Several hundred target genes regulated by NF-κB have been identified. Most of the target genes are involved in the regulation of the immune system and inflammation, cell cycle, proliferation and cell death. Besides its prominent functions in development and response to stress, dysregulated NF-κB contributes to a multitude of diseases including, most importantly, chronic inflammation, autoimmune diseases and cancer.

Stimuli inducing NF-κB activation include pro-inflammatory cytokines, PAMPS (pathogen associated molecular patterns), engagement of immune receptors and different kinds of cellular stresses, such as γ-irradiation (IR). Activated NF-κB pathways regulate different cellular outcomes by transcriptional regulation of target genes that encode for non-coding RNA (ribonucleic acid) or proteins controlling cell survival and proliferation, adhesion and matrix remodelling, lymphocyte activation, host defence or immunity and inflammation.

NF-κB is a family of TFs that includes five members, p65/RelA, RelB, c-Rel and p105/p50 and p100/p52 that form combinatorial homo- and heterodimers (Hayden and Ghosh; 2012). Structurally, all NF-κB subunits feature a Rel homology domain (RHD), which is comprised of a N-terminal domain (NTD), and a dimerisation domain (DID) followed by a nuclear localisation signal (NLS). The RHD is facilitating most of the critical functions like dimerisation with other subunits, nuclear localisation, DNA binding and binding to IκB proteins.

The Rel-proteins are further characterised by the presence of a C-terminal transactivation domain (TAD) that is required for transcription initiation. The precursor proteins p105 and p100 are gene products of NFKB1 and NFKB2, respectively. By ubiquitination and proteasomal processing, p105 and p100 give rise to the mature NF-κB subunits p50 and p52, respectively.

Different post-translational modifications (PTMs) of the NF-κB subunits, such as phosphorylation and acetylation, induce conformational changes and thus have an impact on ubiquitination, stability, protein-protein interactions and regulation of target gene expression (Christian et al.; 2016).

Inactive NF-κB dimers are sequestered in cytoplasm by association to IκB proteins. Upon activation of IKK/NF-κB pathways, the IKK complex phosphorylates IκBα and thus marks it for lysine-48-linked (K48) ubiquitination and subsequent proteasomal degradation (Scheidereit, 1998, Hayden and Ghosh; 2008, Scheidereit; 2006). The released NF-κB dimers then translocate into the nucleus and regulate target genes transcription.

The IκB (inhibitor of nuclear factor-κB) proteins are inhibitors of NF-κB and represent a molecular switch by retaining NF-κB from nuclear translocation. The IκB proteins harbour an ankyrin repeat domain (ARD) as a specific structural feature, which facilitates binding to NF-κB dimers.

IκBα, IκBβ and IκBε sequester NF-κB dimers in the cytoplasm by masking of the NLS and activation of NF-κB requires the release from the IκBs. Liberation of NF-κB from its major inhibitor IκBα involves phosphorylation at two serines (S, Ser) within the N-terminus at positions S32 and S36. To release NF-κB from IκBα, phosphorylation is essential but not sufficient and proteolytic degradation of IκBα as an additional step is obligatory.

Activation of the IKK complex is the fundamental mechanism of NF-κB signaling. The prototypical complex consists of the two catalytic subunits IKKα and IKKβ and the regulatory subunit IKKγ/NEMO (NF-κB essential modifier) (Hinz and Scheidereit; 2014). Upon stimulation, the IKK complex phosphorylates IκBα on the critical serine residues. As a consequence of the phosphorylation, the E3 ligase SCF$^{\beta TrCP}$ attaches K48-linked ubiquitin chains onto IκBα. This degradation signal leads to the destruction of IκBα by the 26S proteasome and consequently to the release of free NF-κB heterodimers.

Different signaling events are required for IKK complex activation. Most IKK/NF-κB pathways involve upstream signaling that leads to ubiquitin-mediated auto-phosphorylation of the kinase TAK1 (TGFβ (transforming growth factor β)-activated kinase-1). Auto-phosphorylation of TAK1 is achieved by recruitment of TAK1/TAB2/3 complexes to K63-linked ubiquitin chains. Activated TAK1 phosphorylates IKKα and IKKβ in the activation loop at S176 and S177, respectively (Zhang et al.; 2014). The IKK complex not solely phosphorylates IκB proteins, but also the NF-κB subunit p65.

Canonical IKK/NF-κB activation is most powerfully activated by inflammatory stimuli such as cytokines like IL-1 (interleukin-1) and TNFα (Tumour necrosis factor alpha) and Toll-like receptor agonists (Zhang et al.; 2014). Upon binding of ligands to their cell membrane bound receptors, the signal is transduced into the cytoplasm. Here, adapter proteins recruit signaling components like kinases and ubiquitin ligases to the receptor complex. Activation of canonical NF-κB is mediated by complex interplay of different ubiquitin chain attachments and protein recruitments that finally lead to poly-ubiquitin binding of IKKγ and to the phosphorylation of IKKα/β by TAK1.

The activated IKK complex phosphorylates p65 at S536 and IκBα at S32 and S36, which leads to proteasomal degradation. The liberated active p65/p50 heterodimer translocates into the nucleus and regulates target gene transcription. As a negative feedback loop IκBα is resynthesised, which diminishes NF-κB activation. Another negative feedback loop represents the expression of the deubiquitinating enzyme A20. A20 deubiquitinates RIP1 (receptor-interacting protein 1) by cleaving attached K63-ubiquitin chains.

Non-canonical (or alternative) NF-κB signaling depends on the proteasomal processing of the precursor p100, which results in the formation of p52. Hallmarks of non-canonical are the requirement of de novo protein synthesis and, in contrast to canonical NF-κB signaling, its distinctive slower kinetics. Central components of the activation of non-canonical NF-κB activation are NF-κB inducing kinase (NIK) and IKKα.

NIK is constantly degraded under steady-state conditions by the proteasome through a mechanism involving ubiquitination mediated by a TRAF3 (Tumour necrosis factor (TNF) receptor-associated factor-3)-TRAF2-cIAP (inhibitor of apoptosis protein) destruction complex.

Trigger of non-canonical NF-κB signaling are ligands of a subset of TNF receptor superfamily members including LT-β (lymphotoxin-β), BAFF (B-cell-activating factor belonging to TNF family), CD40, RANK (receptor activator for nuclear factor KB), TNFR2, Fn14 and others. Upon stimulation of the receptors, TRAF3 is degraded and consequently NIK accumulates in the cell. Accumulated NIK phosphorylates IKKα on its T-loop serines, which in turn phosphorylates p100 within the c-terminus. Phosphorylated precursor molecules are modified with K48-linked ubiquitin chains to trigger proteasomal processing of p100.

As a result of non-canonical NF-κB signaling, p52 is produced, which preferentially binds to RelB. The activated NF-κB heterodimer p52/RelB translocates into the nucleus and binds to its consensus sequences to regulate specific immunological processes like secondary lymphoid organogenesis, B-cell survival and maturation, dendritic cell activation, and bone metabolism (Sun; 2012). However, pathological mechanisms can lead to deregulated NIK stabilisation or IKKα activation. As a consequence the non-canonical NF-κB pathway is constitutively activated, which has been linked to the development of numerous serve disorders such as autoimmunity, inflammation and lymphatic malignancies like Hodgkin's lymphomas.

Genotoxic stress induces a complex cellular process called DNA damage response (DDR). The DDR regulates cell fate decisions like cell cycle arrest and DNA repair, senescence, quiescence apoptosis or other kinds of cell death, depending on the extent of genotoxic stress. DNA double strand breaks induce a nuclear-to-cytoplasmic signaling cascade, which finally cause IKK activation analogously to cytokine-induced NF-κB activation (Stilmann et al.; 2009).

The genotoxic stress-induced NF-κB activation is mediated by a bifurcated pathway (FIG. 1). Two independent molecular sensors, ATM (ataxia telangiectasia mutated) and PARP1 (poly(ADP-ribose)-polymerase-1), recognise DNA lesions and initiate the DDR. Both, PARP1 and ATM, exert various functions in the DDR from initiation of stress responses to facilitation of DNA damage repair. The most prominent substrate of the kinase ATM is the tumour suppressor protein p53, which exerts anti-proliferative functions by the regulation of its target genes. Minor extent of DNA damage leads to a reversible cell cycle arrest until the lesions are resolved. Irreparable DNA lesions cause more extensive cellular responses. To protect the organism against malignant transformation affected cells either drive irreversibly into a non-proliferative state called cellular senescence or undergo apoptosis (Shiloh and Ziv; 2013).

The induction of DSBs leads to the activation of ATM by auto-phosphorylation and to the synthesis of poly(ADP-ribose) (PAR) by PARP1, which is thought to have scaffolding functions. Subsequently, activation of PARP1 leads to the formation of a nuclear signalosome containing the sensor proteins ATM and PARP1 as well as the SUMO (small ubiquitin-related modifier) E3-ligase PIASy (protein inhibitor of activated STAT gamma), LRP16/MACROD1 and the IKK complex subunit IKKγ (Stilmann et al.; 2009; Wu et al., 2015).

Upon induction of genotoxic stress, IKKγ is transported into the nucleus by interacting with the nuclear importer IPO3 (importin 3) and is recruited to the signalosome by binding to auto-PARylated PARP1. Consequently, IKKγ is phosphorylated by ATM and SUMOylated by PIASy.

Subsequently, IKKγ is transported into the cytoplasm and most likely incorporated into newly formed IKK holocomplexes. Simultaneously, phosphorylated ATM translocates into the cytoplasm in a $Ca^{2+}$-dependent manner and initiates the formation of a cytoplasmic signalosome (Hinz et al.; 2010). ATM activates TRAF6 resulting in Ubc-13-mediated K63-linked poly-ubiquitination, which functions as a scaffold for cIAP1 and TAB2-TAK1 recruitment and subsequent TAK1 activation, and to linear ubiquitination of IKKγ, which is accomplished by the linear ubiquitin assembly complex (LUBAC). Depending on the cellular context and type of stimulus additional regulatory components (ELKS, XIAP or RIP1) have been proposed to participate in activation of this pathway. Finally, the cIAP1-dependent mono-ubiquitination of IKKγ essentially requires the formation of the nuclear and the cytosolic signalosome for the activation of the IKK complex, IκBα degradation and subsequent NF-κB activation (Hinz et al.; 2010).

The genotoxic stress-induced IKK/NF-κB pathway is a major regulator of cellular pro-survival signaling by either physiologically occurring DNA damage or therapy induced DNA damage. Therefore, genotoxic stress-induced and DDR-induced IKK/NF-κB activation has an impact on the outcome of many conditions including development, genetic diseases, aging and cancer.

Aberrant NF-κB activation is associated with tumour-promoting inflammation, which is a driving force in tumourigenesis by sustaining a proliferative environment as a consequence of inflammatory cytokine secretion (Hanahan and Weinberg; 2011). Moreover, NF-κB can affect cellular proliferation, angiogenesis, and metastasis through transcriptional regulation of target genes (Baud and Karin; 2009). Constitutively activated NF-κB was found in several human cancers and tumour cell lines derived from hematopoietic and lymphoid malignancies, such as multiple myeloma, acute myeloid leukemia, T cell lymphoma and Hodgkin lymphoma. Similarly, elevated NF-κB activation was found in melanoma cells, in lung carcinoma cells, in bladder cancer cells, in breast cancer cells, and in pancreatic adenocarcinoma cells.

Promotion of carcinogenesis by NF-κB is additionally linked to attenuated cell death signaling. TNFα-induced NF-κB activation has a role in the regulation of anti-apoptotic gene expression and consequently in the inhibition of apoptosis. Similarly, the genotoxic stress-activated NF-κB pathway was shown to regulate the expression of anti-apoptotic proteins, such as cIAP1, cIAP2. In addition, NF-κB controls expression of A1/Bfl-1, which strongly suppressed etoposide-induced cell death by inhibiting mitochondrial release of cytochrome c. Importantly, based on its anti-apoptotic activity, NF-κB activation by genotoxic stress is thought to strongly contribute to cancer therapy resistance, and thus inhibition of NF-κB signaling might results in chemo-sensitization (Lim et al.; 2012).

As NF-κB pathway activation is believed to be a driving force of carcinogenesis and cancer therapy resistance mechanisms, pharmacological inhibition has been suggested as context-dependent useful adjuvants for chemotherapeutic treatment. Proteasome inhibitors were the first used NF-κB pathway inhibitors. However, proteasome inhibitors have undefined molecular specificity and target the canonical and the non-canonical NF-κB pathway, because both signaling cascades rely on degradation or processing functions. The dose-limiting toxic effects for patient treatment with proteasome inhibitors include peripheral neuropathy, thrombocytopenia, neutropenia, anaemia, fatigue, and diarrhea. General IKK/NF-κB pathway inhibition causes systemic toxicity and severe adverse effects due to its pleiotropic functions (Baud and Karin; 2009).

Cancer is associated with uncontrolled cellular proliferation and cancer therapies focus on arresting undesired cell division and growth by the induction of DNA damage through treatment with irradiation or chemotherapeutics. Thus, DNA damaging cancer therapies such as chemo- and irradiation therapies trigger the activation of the genotoxic stress-induced IKK/NF-κB pathway as part of the DNA damage response (DDR). Consequently, the IKK/NF-κB pathway is considered as a potential target of novel types of cancer therapy, besides other conditions including aging, genetic diseases, reperfusion injury, stroke, neurodegeneration and oxidative stress induced DNA-damage. Nevertheless, the general inhibition of the IKK/NF-κB pathway leads to broad immunosuppression and severe adverse effects due to the pleotropic functions of IKK and NF-κB and therefore is not applicable as a therapeutic strategy in patients.

In WO 2007/097981 A2 describes alpha-carbolines as inhibitors of IKK for the treatment of cancer. No pathway specific inhibition of IKK has been described.

Hsu M J et al (Biochemical Pharmacology, Elsevier, US, vol. 70, na 1, 1 Jul. 2005) describe the use of similar molecules as disclosed herein for the treatment of cancer in general.

In WO 2011/011186 A2 a group of inhibitors that are similar the compounds of the present invention are disclosed for use in the treatment of cancer.

Du Hongtao et al (Bioorganic & Medicinal Chemistry Letters, Pergamon, Amsterdam, NL, vol. 26, no. 16, 1 Jul. 2016) describe the synthesis and biological evaluation of N9-substituted harmine derivatives as potential anticancer agents.

Lin Yi-Chien et al (European Journal of Medicinal Chemistry, vol. 110, 7 Jan. 2016) disclose the synthesis and structure-activity relationship of novel 3,9-substituted [alpha]-carboline derivatives with high cytotoxic activity against colorectal cancer cells.

In EP 1634881 A1 describes molecules on the basis of beta-carbolines, which are used in cancer therapy in combination with irradiation therapy.

Chen et al (International Journal of Cancer, vol. 114, no. 5, 1 May 2005) describe antitumor and neurotoxic effects of novel harmine derivatives and structure-activity relationship analysis.

Lamchouri et al (Research on Chemical Intermediates, vol. 39, no. 5, 15 Aug. 2012) examine the quantitative structure-activity relationship of antitumor and neurotoxic [beta]-carbolines alkaloids.

Zhang et al (European Journal of Medicinal Chemistry, vol. 65, pages 21-31) describe the synthesis and structure-activity relationships of N2-alkylated quaternary [beta]-carbolines as novel antitumor agents.

Willemann et al: (Bioorganic & Medicinal Chemistry, vol. 17, no. 13, 1 July) disclose the synthesis and cytotoxic activity of 5,6-heteroaromatically annulated pyridine-2,4-diamines.

Rocca et al (ChemMedChem, vol. 11, no. 16, 23 Mar. 2016) describe the hit identification of a novel dual binder for h-telo/c-myc G-quadruplex by a combination of pharmacophore structure-based virtual screening and docking refinement. The use of the identified molecules for the treatment of cancer is suggested.

Almerico et al: (Journal of Molecular Graphics and Modelling, vol. 42, 19 Mar. 2013) describe potential inhibitors of the A3 adenosine receptor.

Silva et al (Chemical and Pharmaceutical Bulletin, 2012, pages 1372-1379) describe the synthesis, antitumor, anti-trypanosomal and antileishmanial activities of benzo[4,5] canthin-6-ones bearing the N'-(Substituted benzylidene)-carbohydrazide and N-alkylcarboxamide groups at C-2.

Lamkanfi et al (The Journal of Cell Biology, vol. 173, no. 2, 17, April 2006) summarize the mechanisms of caspase-mediated activation of NF-κB.

Jin et al (Cancer Research, vol. 69, no. 5, 10 Feb. 2009) show that cIAP1, cIAP2, and XIAP act cooperatively via nonredundant pathways to regulate genotoxic stress-induced nuclear factor-B activation.

None of the cited documents describes a compound for use as a medicament specifically in the treatment of a subject suffering from cancer exhibiting genotoxic stress-induced IKK/NF-κB activation or of a subject where genotoxic cancer treatment induces IKK/NF-κB activation. In the state of the art no compound has been described that specifically acts on the genotoxic stress-induced IKK/NF-κB pathway, but does not directly inhibit IKK and leaves other pathways leading to IKK/NF-κB activation unaffected. Furthermore, the compounds of the present invention have not been described in the prior art.

Thus, there is a need to develop new classes of pathway tailored inhibitors, which interfere only with a stimulus-specific NF-κB activation, while leaving other modes of NF-κB activation intact. Given the important role of NF-κB in cancer treatment resistance mechanisms, there is an urgent need to develop targeted therapy approaches aiming against the genotoxic stress-induced pro-survival IKK/NF-κB pathway. To the knowledge of the inventors, no NF-κB inhibitor specific for this pathway has been previously reported.

In light of the prior art there remains a significant need in the art to provide additional means for the treatment of a disease associated with genotoxic stress-induced IKK/NF-κB activation.

SUMMARY OF THE INVENTION

In light of the prior art the technical problem underlying the present invention is to provide means for the treatment of a disease associated with genotoxic stress-induced IKK/NF-κB activation.

This problem is solved by the features of the independent claims. Preferred embodiments of the present invention are provided by the dependent claims.

The invention relates to a compound according to Formula I for use as a medicament in the treatment of a disease associated with genotoxic stress-induced IKK/NF-κB activation,

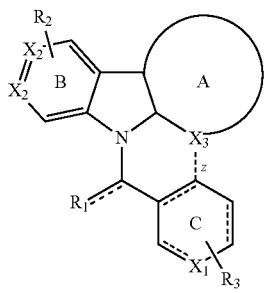

Formula I wherein
R1=H, O;
R2=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

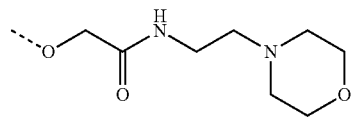

(OCH2CONHC2H4NC4H8O) or OC2H4OC2H2NH2;

R3=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms;
X1, X2, X3=N or C; preferably C,
ring A is an aromatic cyclic structure of 5 or 6 members, optionally comprising 0, 1, or 2 heteroatoms selected from O and/or N, preferably forming a pyrazolyl, imidazolyl, pyridyl, pyrimidyl, pyridazyl, pyrazinyl ring, wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3;
the bond z may be present or not present, wherein when bond z is not present:
the C of bond z of ring C is substituted with R3, and X3 of the A ring is substituted with H, OH, halogen, preferably Br, Cl or F, C1-C7 alkyl, alkenyl, alkynyl, alkoxy, carbonyl, carboxyl, alkoxycarbonyl, amine.

In a preferred embodiment the compound of formula I is characterized in that at least one of R2 from 0-4 is not H.

In a preferred embodiment the compound of formula I is characterized in that X3 is C.

In a preferred embodiment the compound of formula I is characterized in that R1=O.

In a preferred embodiment the compound of formula I is characterized in that ring A is a heteroaromatic structure of 5 or 6 members comprising 1 or 2 heteroatoms.

In a preferred embodiment the invention relates to a compound according to Formula I, for use as a medicament in the treatment of a disease associated with genotoxic stress-induced IKK/NF-κB activation, wherein ring A is a heteroaromatic structure selected from the group consisting of

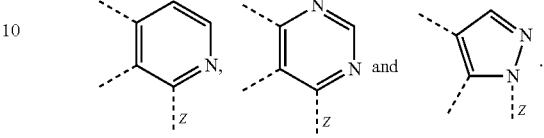

Preferably, the invention relates to the compound according to Formula I for use as a medicament in the treatment of a subject suffering from cancer exhibiting genotoxic stress-induced IKK/NF-κB activation.

It was entirely surprising to find a compound that selectively inhibits the pathway leading to activation of IKK/NF-κB that is activated upon the encounter of genotoxic-stress, such as DNA-damage. So far all attempts to identify such compounds were unsuccessful and NF-κB pathway inhibition has mainly been achieved by directly targeting the IKK complex.

Because of the many effects and functions of the NF-κB pathways, all of which depend on IKK, direct inhibition of the IKK complex or other downstream molecules leads to intolerable side effects including broad immunosuppression, which harbors high risks of infections and might lead to escape of cancer cells from immune surveillance. These disadvantages of known NF-κB pathway inhibitors are overcome by the means of the present invention, in particular those compounds described herein under Formulae I, I-a, I-b, II, II-a, II-b, III, III-a, IV, IV-a, V, VI, VII.

In the prior art, general IKK inhibitors have been described. In contrast, the compounds of the present invention are pathway-selective inhibitors of IKK-NF-κB, which do not directly act on IKK. Previously described IKK inhibitors are direct IKK inhibitors and do not discriminate between gentotoxic stress-induced IKK-NF-κB signaling and the many other pathways that activate NF-κB through IKK.

The compounds according to formula I predominantly inhibit activation of the genotoxic-stress-induced IKK/NF-κB pathway, but not any other pathways of NF-κB activation including the canonical and non-canonical pathway (or to some minor extent, and not to a large extent or as large an extent as the genotoxic-stress-induced IKK/NF-κB pathway). The inhibition shown by these compounds is therefore "genotoxic-stress-induced IKK/NF-κkB pathway-specific", such that this pathway is inhibited more than other IKK/NF-κB pathways. This selective inhibition has the advantage that side-effects resulting from inhibition of other NF-κB activation pathways, including canonical and non-canonical NF-κB activation, can be excluded or reduced. This makes it possible to tolerate treatment with a compound according to the general as described herein over prolonged periods of multiple days, weeks or even years without suffering from disadvantageous side effects, thereby providing a new clinical situation over known means in the art. Novel dosage regimes are therefore enabled.

To the knowledge of the inventors the compounds described herein are defined by novel technical effect, namely by the inhibition of genotoxic stress-induced IKK/NF-κB activation.

The advantageous effect of the present compound is mediated through inhibition of the activation of the IKK/NF-κB pathway in response to genotoxic-stress or DNA double strand breaks (DSB) through functional interference with the unique protein-protein interactions (nuclear PARP1 signalosome), posttranslational modifications (SUMOylation and phosphorylation of IKKγ), translocation processes (cytoplasmic ATM import), or other specific components of the DNA DSB or genotoxic-stress-induced NF-κB signaling cascade, which are not involved in the activation of or shared with shared with any other NF-κB pathways.

Surprisingly the compounds according to the formula described herein were effective in inhibiting genotoxic stress induced NF-κB activation in sub-micromolar concentrations, whereas no inhibition of the canonical NF-κB pathway could be detected. An important surprising advantage of the treatment with the compounds disclosed here is that they inhibited both the nuclear export of ATM and the formation of the PARP1 signalosome, without affecting their enzymatic activity. This is a great advantage of the present invention as the inhibition of the signaling cascade downstream of ATM and PARP1 by the compounds of the present invention is specific for NF-κB activation and does not interfere with the activation of other ATM substrates such as the tumor suppressor protein p53, which prevents the occurrence of side effects resulting from interference with other functions of ATM and PARP1. Another advantage of the treatment with compounds according to formula 1 is the reduction of expression of anti-apoptotic genes, leading to an increase in apoptosis, which is beneficial for example in the case of cancer.

The technical effect achieved by the present compounds therefore enables the treatment of new patient groups, such as patients previously sensitive to off target side effects of NF-κB inhibition, or in particular patients that have cancer conditions that exhibit resistance to DNA damaging cancer treatments. This particular patient population represents a great challenge to medical practitioners and the compounds described herein are a promising solution to this problem.

In a preferred embodiment the invention relates to a compound according to Formula I-a, for use as a medicament in the treatment of a disease associated with genotoxic stress-induced IKK/NF-κB activation, or wherein R2 is alkoxyamine, alkoxyamide, such as

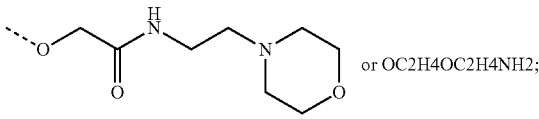 or OC2H4OC2H4NH2;

R3=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms;

R4=can be 0-2, the same or different, selected from H, OH, halogen, preferably Br, Cl or F, C1-C7 alkyl, alkenyl, alkynyl, alkoxy, carbonyl, carboxyl, alkoxycarbonyl, amine, aryl;

X1, X2=N or C, preferably C;

X3=N;

X4=N or C, preferably wherein only one X4 is N;

the bond z may be present or not present, wherein when bond z is not present:

the C atom of bond z of ring C is substituted with R3, and

X3 of the A ring is substituted with H, C1-C7 alkyl, alkenyl, alkynyl, alkoxy, carbonyl, carboxyl, alkoxycarbonyl, amine, aryl.

In a preferred embodiment the compound of formula I-a is characterized in that R4=can be 0-2, the same or different, selected from H, OH, halogen, preferably Br, Cl or F, C1-C7 alkyl, alkenyl, alkynyl, alkoxy, carbonyl, such as CO-phenyl (optionally substituted with halogen, C1-C3 alkyl, alkoxy, amine), carboxyl, alkoxycarbonyl, amine, aryl, such as phenyl (optionally substituted with halogen, C1-C3 alkyl, alkoxy, amine), alkoxyamine, such as CONHC3H6OCH3.

In a preferred embodiment the invention relates to a compound according to Formula I-b, for use as a medicament in the treatment of a disease associated with genotoxic stress-induced IKK/NF-κB activation,

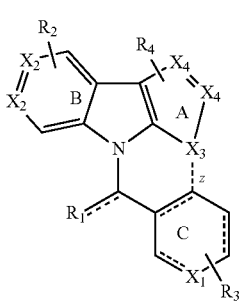

Formula I-a

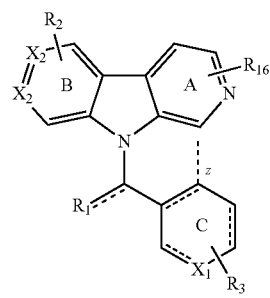

Formula I-b wherein
R1=H, O;
R2=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, wherein
R1=H, O;
R2=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

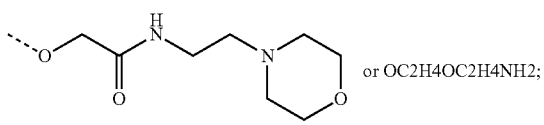 or OC2H4OC2H4NH2;

R3=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms;

X1, X2=N or C, preferably C;

R16=can be 0-3, preferably 0, 1, 2, the same or different, H, halogen, preferably Cl, Br, F, C1-C7, preferably C1-C5, alkyl, alkoxy, preferably methoxy;

the bond z may be present or not present, wherein when bond z is not present:

the C atom of bond z of ring C is substituted with R3, and the C atom of bond z of ring A is substituted with H, C1-C7 alkyl, alkenyl, alkynyl, alkoxy, carbonyl, carboxyl, alkoxycarbonyl, amine, aryl.

In a preferred embodiment the compound of formula I-b is characterized in that at least one of R2 from 0-4 is not H.

In a preferred embodiment the compound of formula I-b is characterized in that R1=O.

In a preferred embodiment the invention relates to a compound according to Formula II, for use as a medicament in the treatment of a disease associated with genotoxic stress-induced IKK/NF-κB activation, Formula II

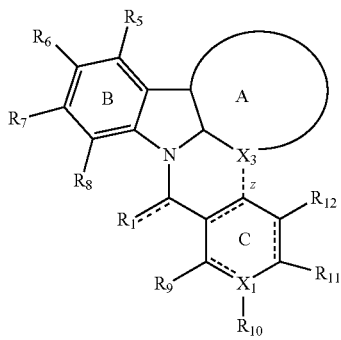

wherein
R1=H, O;
R5=H, halogen, preferably Cl, Br, F, C1-C5, preferably C1-C3, alkyl, alkenyl, alkoxy, amine, most preferably H;
R6=H, OH, halogen, preferably Cl, Br, F, C1-C5, preferably C1-C3, alkyl, alkoxy, preferably methoxy, or alkoxyamine, alkoxyamide, such as

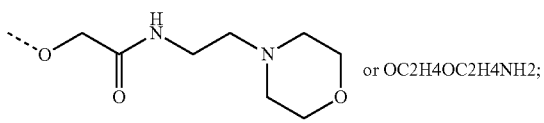 or OC2H4OC2H4NH2;

R7=H, halogen, preferably Cl, Br, F, C1-C5, preferably C1-C3, alkyl, alkoxy, preferably methoxy;

R8=H, halogen, preferably Cl, Br, F, C1-C5, preferably C1-C3, alkyl, alkoxy, preferably methoxy, most preferably H;

R9=H, halogen, preferably Cl, Br, F, C1-C5, preferably C1-C3, alkyl, alkoxy, preferably methoxy;

R10=H, halogen, preferably Cl, Br, F, C1-C5, preferably C1-C3, alkyl, alkoxy, preferably methoxy;

R11=H, halogen, preferably Cl, Br, F, C1-C5, preferably C1-C3, alkyl, alkoxy, preferably methoxy, carboxyl;

R12=H, halogen, preferably Cl, Br, F, C1-C5, preferably C1-C3, alkyl, alkoxy, preferably methoxy;

or wherein when X1 is C, R9 and R10, R10 and R11, R11 and R12, or R12 and the C in the position of bond z of ring C, form an optionally aromatic cyclic structure of 5 or 6 members, comprising 0, 1, or 2 heteroatoms, preferably O or N, more preferably 2 O atoms, or forming phenyl;

X1, X3=N or C;

ring A is an aromatic cyclic structure of 5 or 6 members, comprising 0, 1, or 2 heteroatoms selected from O and/or N, preferably forming a pyrazolyl, imidazolyl, pyridyl, pyrimidyl, pyridazyl, pyrazinyl ring, wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3;

the bond z may be present or not present, wherein when bond z is not present:

the C in the position of bond z of ring C is potentially substituted with halogen, preferably Cl, Br, F, C1-C5, preferably C1-C3, alkyl, and X3 of the A ring is optionally substituted with H, C1-C5, preferably C1-C3, alkyl, or when X3 is C potentially with H, C1-C5, preferably C1-C3, alkyl, OH, halogen, preferably Br, Cl or F.

In a preferred embodiment the compound of formula II is characterized in that at least one of R5 to R8 is not H.

In a preferred embodiment the compound of formula II is characterized in that X3 is C.

In a preferred embodiment the compound of formula II is characterized in that R1=O.

In a preferred embodiment the compound of formula II is characterized in that ring A is a heteroaromatic structure of 5 or 6 members comprising 1 or 2 heteroatoms.

ring A is a heteroaromatic structure selected from the group consisting of

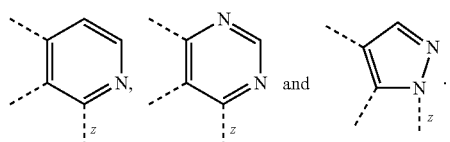

In a preferred embodiment the invention relates to a compound according to Formula II-a, for use as a medicament in the treatment of a disease associated with genotoxic stress-induced IKK/NF-κB activation,

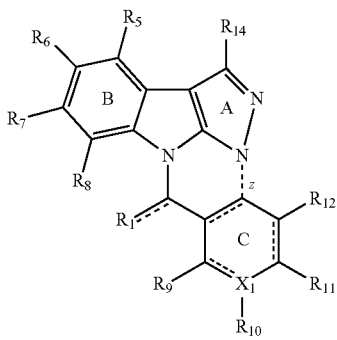

Formula II-a

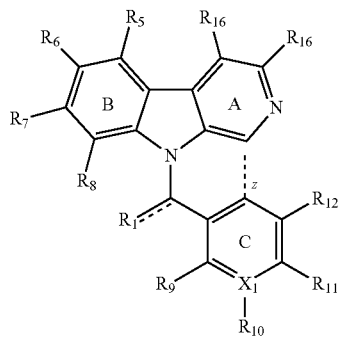

Formula II-b wherein

X1=C or N, preferably C;

R1=H, O;

R5=H, halogen, preferably Cl, Br, F, C1-C5, preferably C1-C3, alkyl, alkoxy, preferably methoxy, most preferably H;

R6=H, halogen, preferably Cl, Br, F, C1-C5, preferably C1-C3, alkyl, alkoxy, preferably methoxy, or OC2H4OC2H4NH2;

R7=H, halogen, preferably Cl, Br, F, C1-C5, preferably C1-C3, alkyl, alkoxy, preferably methoxy;

R8=H, halogen, preferably Cl, Br, F, C1-C5, preferably C1-C3, alkyl, alkoxy, preferably methoxy, most preferably H;

R9=H, halogen, preferably Cl, Br, F;

R10=H, halogen, preferably Cl, Br, F, C1-C5, preferably C1-C3, alkyl, alkoxy, preferably methoxy;

R11=H, halogen, preferably Cl, Br, F, C1-C5, preferably C1-C3, alkyl, alkoxy, preferably methoxy, carboxyl;

R12=H, halogen, preferably Cl, Br, F, C1-C5, preferably C1-C3, alkyl, alkoxy, preferably methoxy;

or wherein when X1 is C, R9 and R10, R10 and R11, R11 and R12, or R12 and the C atom of bond z of ring C when bond z is not present, form an optionally aromatic cyclic structure of 5 or 6 members, optionally comprising 0, 1, or 2 heteroatoms, preferably O or N, more preferably 2 O atoms, or phenyl;

R14=H, C1-C5, preferably C1-C3, alkyl;

wherein the bond z may be present or not present, wherein when bond z is not present:

the C atom of bond z of ring C is substituted with H, halogen, preferably Cl, Br, F, C1-C5, preferably C1-C3, alkyl, alkoxy, preferably methoxy, and the N atom of bond z of ring A is substituted with H, C1-C5, preferably C1-C3, alkyl, alkenyl, alkynyl, alkoxy, carbonyl, carboxyl, alkoxycarbonyl, amine, aryl.

In a preferred embodiment the invention relates to a compound according to Formula II-b, for use as a medicament in the treatment of a disease associated with genotoxic stress-induced IKK/NF-κB activation, wherein X1=C or N, preferably C;

R1=H, O;

R5=H, halogen, preferably Cl, Br, F, C1-C5, preferably C1-C3, alkyl, alkoxy, preferably methoxy, most preferably H;

R6=H, halogen, preferably Cl, Br, F, C1-C5, preferably C1-C3, alkyl, alkoxy, preferably methoxy, or OC2H4OC2H4NH2;

R7=H, halogen, preferably Cl, Br, F, C1-C5, preferably C1-C3, alkyl, alkoxy, preferably methoxy;

R8=H, halogen, preferably Cl, Br, F, C1-C5, preferably C1-C3, alkyl, alkoxy, preferably methoxy, most preferably H;

R9=H, halogen, preferably Cl, Br, F;

R10=H, halogen, preferably Cl, Br, F, C1-C5, preferably C1-C3, alkyl, alkoxy, preferably methoxy;

R11=H, halogen, preferably Cl, Br, F, C1-C5, preferably C1-C3, alkyl, alkoxy, preferably methoxy, carboxyl;

R12=H, halogen, preferably Cl, Br, F, C1-C5, preferably C1-C3, alkyl, alkoxy, preferably methoxy;

R16=the same or different, H, halogen, preferably Cl, Br, F, C1-C5, preferably C1-C3, alkyl, alkoxy, preferably methoxy;

or wherein when X1 is C, R9 and R10, R10 and R11, R11 and R12, or R12 and the C atom of bond z of ring C when bond z is not present, form an optionally aromatic cyclic structure of 5 or 6 members, optionally comprising 0, 1, or 2 heteroatoms, preferably O or N, more preferably 2 O atoms, or phenyl;

R14=H, C1-C5, preferably C1-C3, alkyl;

wherein the bond z may be present or not present, wherein when bond z is not present:

the C atom of bond z of ring C is substituted with H, halogen, preferably Cl, Br, F, C1-C5, preferably C1-C3, alkyl, alkoxy, preferably methoxy, and the C atom of bond z of ring A is substituted with H, halogen, preferably Cl, Br, F, C1-C5, preferably C1-C3, alkyl, alkenyl, alkynyl, alkoxy, carbonyl, carboxyl, alkoxycarbonyl, amine, aryl.

In a preferred embodiment the compound of formula II-b is characterized in that at least one of R5 to R8 is not H.

In a preferred embodiment the compound of formula II-b is characterized in that R1=O.

A further aspect of the invention relates to a compound, and preferably its medical use as described herein, according to Formula III,

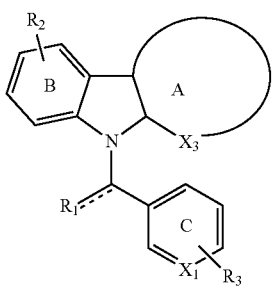

wherein the substituents of Formula III are:

R1=H, O;

R2=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

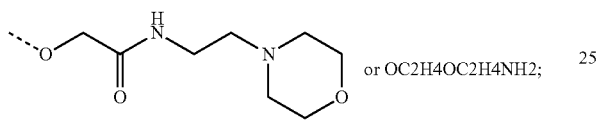 or OC2H4OC2H4NH2;

R3=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents form an optionally aromatic cyclic structure of 5 or 6 members, optionally comprising 0, 1, or 2 heteroatoms, preferably O or N, more preferably 2 O atoms, or forming phenyl;

X1, X3=N or C;

ring A is a heteroaromatic structure of 5 members, comprising 1 or 2 N atoms, wherein X3 must be N, preferably forming a pyrazolyl or imidazolyl ring, or ring A is a heteroaromatic structure of 6 members, comprising 1 N atom, preferably forming a pyridyle ring, wherein the cyclic structure of ring A is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3.

In one embodiment the substituents described above in the preceding paragraph are characterised in that R2 is not carboxyl, wherein the remaining substituents are the same as described in the preceding paragraph.

In a preferred embodiment the compound of formula III is characterized in that at least one of R2 from 0-4 is not H.

In a preferred embodiment the compound of formula III is characterized in that X3 is C.

In a preferred embodiment the compound of formula III is characterized in that R1=0.

In a preferred embodiment the compound of formula III is characterized in that ring A is a heteroaromatic structure selected from the group consisting of

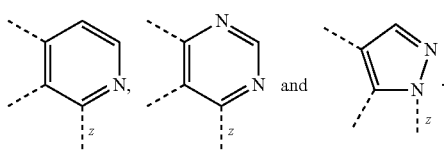

A further aspect of the invention relates to a compound, and preferably its medical use as described herein, according to Formula III-a, Formula III-a

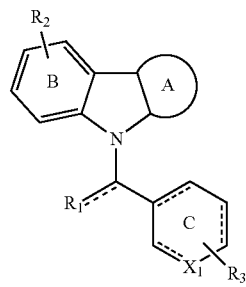

wherein

R1=H, O;

R2=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

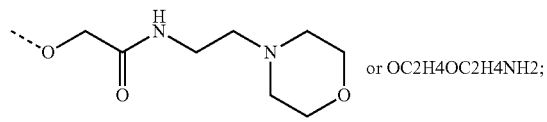 or OC2H4OC2H4NH2;

R3=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents form an optionally aromatic cyclic structure of 5 or 6 members, optionally comprising 0, 1, or 2 heteroatoms, preferably O or N, more preferably 2 O atoms, or forming phenyl;

X1=N or C;

ring A is a heteroaromatic structure of 5 or 6 members, comprising 1 or 2 N atoms, preferably forming a pyrazolyl, imidazolyl, pyridyl, pyrimidyl, pyridazyl, pyrazinyl ring, wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3.

In one embodiment the substituents described above in the preceding paragraph are characterised in that R2 is not carboxyl, wherein the remaining substituents are the same as described in the preceding paragraph.

In a preferred embodiment the compound of formula III-a is characterized in that at least one of R2 from 0-4 is not H.

In a preferred embodiment the compound of formula III-a is characterized in that R1=O.

In a preferred embodiment the compound of formula III-a is characterized in that ring A is a heteroaromatic structure selected from the group consisting of

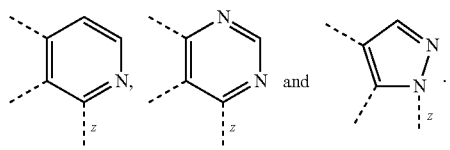

A further aspect of the invention relates to a compound, and preferably its medical use as described herein, according to Formula IV, Formula IV

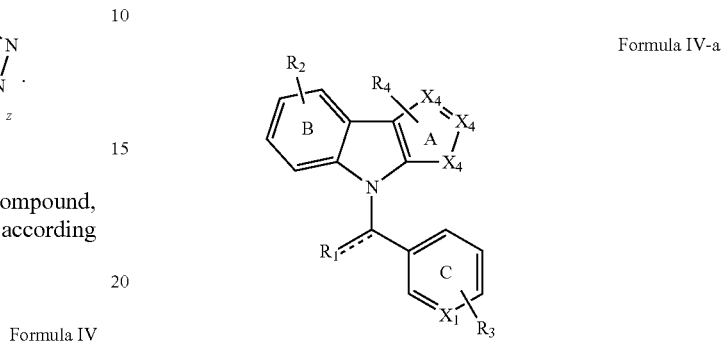

Wherein:
R1=H, O;
R2=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as $$\cdots O \overset{}{\underset{O}{\bigg\langle}} \overset{H}{N} \sim N \bigcirc O \quad \text{or} \quad OC2H4OC2H4NH2;$$

R3=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms, or form phenyl;
X1=C or N;
X3=N;
X4=N or C;
R4=can be 0-2, the same or different, selected from H, OH, halogen, preferably Br, Cl or F, C1-C7 alkyl, alkenyl, alkynyl, alkoxy, carbonyl, carboxyl, alkoxycarbonyl, amine, aryl.

In a preferred embodiment the compound of formula IV is characterized in that R4=can be 0-2, the same or different, selected from H, OH, halogen, preferably Br, Cl or F, C1-C7 alkyl, alkenyl, alkynyl, alkoxy, carbonyl, such as CO-phenyl (optionally substituted with halogen, C1-C3 alkyl, alkoxy, amine), carboxyl, alkoxycarbonyl, amine, aryl, such as phenyl (optionally substituted with halogen, C1-C3 alkyl, alkoxy, amine), alkoxyamine, such as CONHC3H6OCH3.

In a preferred embodiment the invention relates to a compound, and preferably its medical use as described herein, according to Formula IV-a, Formula IV-a wherein
R1=H, O;
R2=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as $$\cdots O \overset{}{\underset{O}{\bigg\langle}} \overset{H}{N} \sim N \bigcirc O \quad \text{or} \quad OC2H4OC2H4NH2;$$

R3=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms, or form phenyl;
X1=C or N, preferably C;
X4=N or C, whereby at least one X4 is N;
R4=can be 0-2, the same or different, selected from H, OH, halogen, preferably Br, Cl or F, C1-C7 alkyl, alkenyl, alkynyl, alkoxy, carbonyl, carboxyl, alkoxycarbonyl, amine, aryl.

In a preferred embodiment the compound of formula IV-a is characterized in that R4=can be 0-2, the same or different, selected from H, OH, halogen, preferably Br, Cl or F, C1-C7 alkyl, alkenyl, alkynyl, alkoxy, carbonyl, such as CO-phenyl (optionally substituted with halogen, C1-C3 alkyl, alkoxy, amine), carboxyl, alkoxycarbonyl, amine, aryl, such as phenyl (optionally substituted with halogen, C1-C3 alkyl, alkoxy, amine), alkoxyamine, such as CONHC3H6OCH3.

In a preferred embodiment the invention relates to a compound, and preferably its medical use as described herein, according to Formula V, Formula V

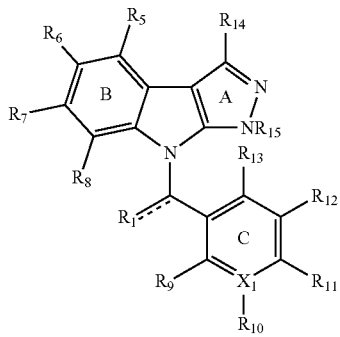

wherein
X1=C or N;
R1=H, O;
R5=H, halogen, preferably Cl, Br, F, C1-C5, preferably C1-C3, alkyl, alkoxy, preferably methoxy, most preferably H;
R6=H, halogen, preferably Cl, Br, F, C1-C5, preferably C1-C3, alkyl, alkoxy, preferably methoxy, or OC2H4OC2H4NH2;
R7=H, halogen, preferably Cl, Br, F, C1-C5, preferably C1-C3, alkyl, alkoxy, preferably methoxy;
R8=H, halogen, preferably Cl, Br, F, C1-C5, preferably C1-C3, alkyl, alkoxy, preferably methoxy, most preferably H;
R9=H, halogen, preferably Cl, Br, F;
R10=H, halogen, preferably Cl, Br, F, C1-C5, preferably C1-C3, alkyl, alkoxy, preferably methoxy;
R11=H, halogen, preferably Cl, Br, F, C1-C5, preferably C1-C3, alkyl, alkoxy, preferably methoxy, carboxyl;
R12=H, halogen, preferably Cl, Br, F, C1-C5, preferably C1-C3, alkyl, alkoxy, preferably methoxy;
R13=halogen, preferably Cl, Br, F,
or wherein when X1 is C, R9 and R10, R10 and R11, R11 and R12, or R12 and R13, form an optionally aromatic cyclic structure of 5 or 6 members, optionally comprising 0, 1, or 2 heteroatoms, preferably O or N, more preferably 2 O atoms, or phenyl;
R14=H, C1-C5, preferably C1-C3, alkyl;
R15=H, C1-C5, preferably C1-C3, alkyl, carbonyl, CO-aryl, preferably benzoyl optionally substituted with halogen, preferably Cl, Br, F, C1-C5, preferably C1-C3, alkyl, alkoxy.

In a preferred embodiment the invention relates to a compound, and preferably its medical use as described herein, according to Formula VI, Formula VI

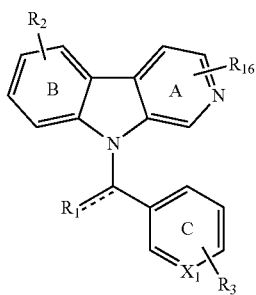

wherein
R1=H, O;
R2=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

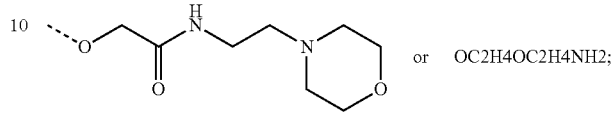

R3=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms, or form phenyl;
X1=N or C;
R16=can be 0-3, preferably 0, 1, 2, the same or different, H, halogen, preferably Cl, Br, F, C1-C5, preferably C1-C3, alkyl, alkoxy, preferably methoxy.

In a preferred embodiment the invention relates to a compound, and preferably its medical use as described herein, according to Formula VI, wherein at least one of R2 from 0-4 is not H.

In a preferred embodiment the invention relates to a compound, and preferably its medical use as described herein, according to Formula VI, wherein R1=O.

In a preferred embodiment the invention relates to a compound, and preferably its medical use as described herein, according to Formula VII, Formula VII

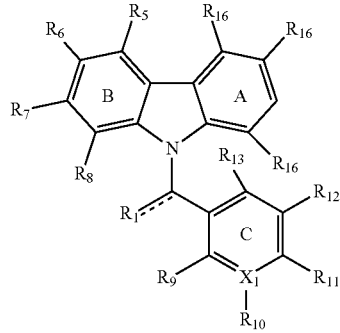

wherein
X1=C or N;
R1=H, O;
R5=H, halogen, preferably Cl, Br, F, C1-C5, preferably C1-C3, alkyl, alkoxy, preferably methoxy, most preferably H;
R6=H, halogen, preferably Cl, Br, F, C1-C5, preferably C1-C3, alkyl, alkoxy, preferably methoxy, or OC2H4OC2H4NH2;
R7=H, halogen, preferably Cl, Br, F, C1-C5, preferably C1-C3, alkyl, alkoxy, preferably methoxy;
R8=H, halogen, preferably Cl, Br, F, C1-C5, preferably C1-C3, alkyl, alkoxy, preferably methoxy, most preferably H;

R9=H, halogen, preferably Cl, Br, F,
R10=H, halogen, preferably Cl, Br, F, C1-C5, preferably C1-C3, alkyl, alkoxy, preferably methoxy;
R11=H, halogen, preferably Cl, Br, F, C1-C5, preferably C1-C3, alkyl, alkoxy, preferably methoxy, carboxyl;
R12=H, halogen, preferably Cl, Br, F, C1-C5, preferably C1-C3, alkyl, alkoxy, preferably methoxy;
R13=H, halogen, preferably Cl, Br, F,
or wherein when X1 is C, R9 and R10, R10 and R11, R11 and R12, or R12 and R13, form an optionally aromatic cyclic structure of 5 or 6 members, optionally comprising 0, 1, or 2 heteroatoms, preferably O or N, more preferably 2 O atoms, or phenyl;
R16=the same or different, H, halogen, preferably Cl, Br, F, C1-C5, preferably C1-C3, alkyl, alkoxy, preferably methoxy.

A further aspect of the invention relates to a compound, and preferably its medical use as described herein, according to Formula VII, wherein the substituents of Formula VII are:
X1=C or N;
R1=H, O;
R5=H, halogen, preferably Cl, Br, F, C1-C5, preferably C1-C3, alkyl, alkoxy, preferably methoxy, most preferably H;
R6=H, halogen, preferably Cl, Br, F, C1-C5, preferably C1-C3, alkyl, alkoxy, preferably methoxy, or OC2H4OC2H4NH2;
R7=H, halogen, preferably Cl, Br, F, C1-C5, preferably C1-C3, alkyl, alkoxy, preferably methoxy;
R8=H, halogen, preferably Cl, Br, F, C1-C5, preferably C1-C3, alkyl, alkoxy, preferably methoxy, most preferably H;
R9=H, halogen, preferably Cl, Br, F,
R10=H, halogen, preferably Cl, Br, F, C1-C5, preferably C1-C3, alkyl, alkoxy, preferably methoxy;
R11=H, halogen, preferably Cl, Br, F, C1-C5, preferably C1-C3, alkyl, alkoxy, preferably methoxy, carboxyl;
R12=H, halogen, preferably Cl, Br, F, C1-C5, preferably C1-C3, alkyl, alkoxy, preferably methoxy;
R13=H, halogen, preferably Cl, Br, F,
or wherein when X1 is C, R9 and R10, R10 and R11, R11 and R12, or R12 and R13, form an optionally aromatic cyclic structure of 5 or 6 members, optionally comprising 0, 1, or 2 heteroatoms, preferably O or N, more preferably 2 O atoms, or phenyl;
R16=the same or different, H, halogen, preferably Cl, Br, F, C1-C5, preferably C1-C3, alkyl, alkoxy, preferably methoxy;
wherein ring C is substituted with only one Cl atom, if R16 is methyl.

In a preferred embodiment the invention relates to a compound, and preferably its medical use as described herein, according to Formula VII, wherein at least one of R5 to R8 is not H.

In a preferred embodiment the invention relates to a compound, and preferably its medical use as described herein, according to Formula VII, wherein R1=O.

In a preferred embodiment the compound of the invention is selected from the group provided in Table 1. In a preferred embodiment the invention relates to the compounds in table 1 as a medicament in the treatment of a disease associated with genotoxic stress-induced IKK/NF-κB activation.

TABLE 1

| Compounds of the present invention. | | | | |
|---|---|---|---|---|
| Structure | ID | Ex. | IUPAC | MS (ES+) [M + H]: m/e |
| | D12 | 11 | (6-Methoxy-9H-pyrido[3,4-b]indol-9-yl)(4-methoxyphenyl)methanone | 333 |
| | D11 | 10 | (6-Methoxy-9H-pyrido[3,4-b]indol-9-yl)(phenyl)methanone | 303 |

TABLE 1-continued

Compounds of the present invention.

| Structure | ID | Ex. | IUPAC | MS (ES+) [M + H]: m/e |
|---|---|---|---|---|
| 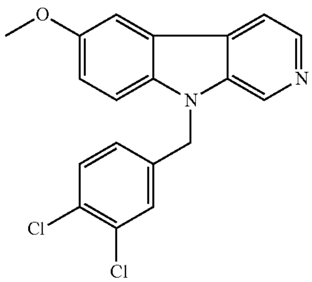 [SMILES: COc1ccc2c(c1)c1ccncc1n2Cc1ccc(Cl)c(Cl)c1] | D06 | 6 | 9-(3,4-Dichlorobenzyl)-6-methoxy-9H-pyrido[3,4-b]indole | 357/359 dichloro pattern |
| 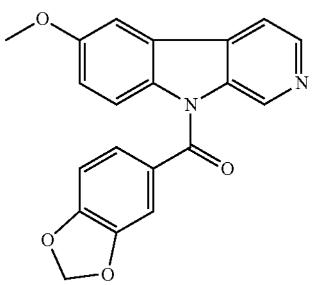 [SMILES: COc1ccc2c(c1)c1ccncc1n2C(=O)c1ccc2c(c1)OCO2] | D13 | 12 | Benzo[d][1,3]dioxol-5-yl(6-methoxy-9H-pyrido[3,4-b]indol-9-yl)methanone | 347 |
| 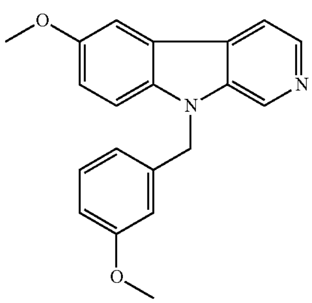 [SMILES: COc1cccc(Cn2c3ccc(OC)cc3c3ccncc32)c1] | D04 | 4 | 9-Benzyl-6-methoxy-9H-pyrido[3,4-b]indole | 319 |
| 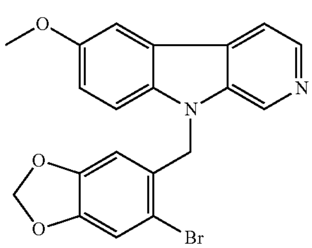 [SMILES: COc1ccc2c(c1)c1ccncc1n2Cc1cc2c(cc1Br)OCO2] | D07 | 7 | 9-((6-Bromobenzo[d][1,3]dioxol-5-yl)methyl)-6-methoxy-9H-pyrido[3,4-b]indole | 411/413 bromo pattern |
| 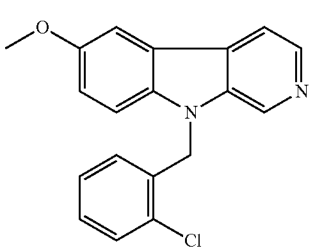 [SMILES: COc1ccc2c(c1)c1ccncc1n2Cc1ccccc1Cl] | D01 | 1 | 9-(2-Chlorobenzyl)-6-methoxy-9H-pyrido[3,4-b]indole | 323 |

TABLE 1-continued

Compounds of the present invention.

| Structure | ID | Ex. | IUPAC | MS (ES+) [M + H]: m/e |
|---|---|---|---|---|
| 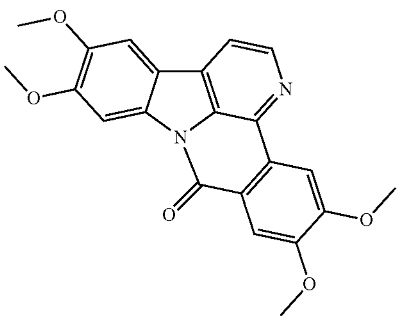 | D16 | 17 | 5,6,11,12-Tetramethoxy-8H-benzo[c]indolo[3,2,1-ij][1,5]naphthyridin-8-one | 391 |
| 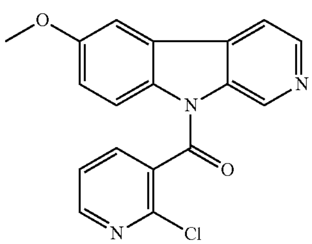 [SMILES: COc1ccc2c(c1)c1ccncc1n2C(=O)c1cccnc1Cl] | D15 | 14 | (2-Chloropyridin-3-yl)(6-methoxy-9H-pyrido[3,4-b]indol-9-yl)methanone | 338 |
| 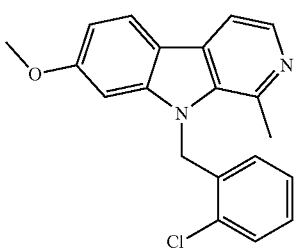 [SMILES: COc1ccc2c3ccnc(C)c3n(Cc3ccccc3Cl)c2c1] | D02 | 2 | 9-(2-Chlorobenzyl)-7-methoxy-1-methyl-9H-pyrido[3,4-b]indole | 337 |
| 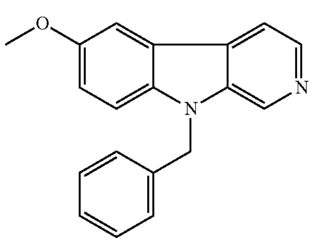 [SMILES: COc1ccc2c(c1)c1ccncc1n2Cc1ccccc1] | D05 | 5 | 9-Benzyl-6-methoxy-9H-pyrido[3,4-b]indole | 289 |
| 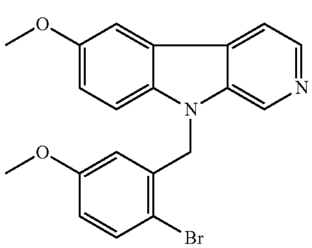 [SMILES: COc1ccc(Br)c(Cn2c3ccc(OC)cc3c3ccncc32)c1] | D18 | 8 | 9-(2-Bromo-5-methoxybenzyl)-6-methoxy-9H-pyrido[3,4-b]indole | 397/399 bromo pattern |

TABLE 1-continued

Compounds of the present invention.

| Structure | ID | Ex. | IUPAC | MS (ES+) [M + H]: m/e |
|---|---|---|---|---|
| 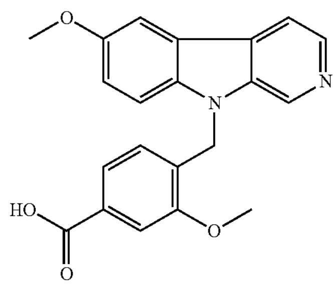 [SMILES: COc1ccc2c(c1)c1ccncc1n2Cc1ccc(C(=O)O)cc1OC] | D03 | 3 | 3-Methoxy-4-((6-methoxy-9H-pyrido[3,4-b]indol-9-yl)methyl)benzoic acid | 363 |
| 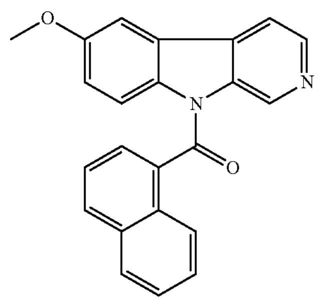 [SMILES: COc1ccc2c(c1)c1ccncc1n2C(=O)c1cccc2ccccc12] | D17 | 15 | (6-Methoxy-9H-pyrido[3,4-b]indol-9-yl)(naphthalen-1-yl)methanone | 353 |
| 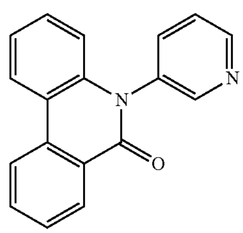 [SMILES: O=c1c2ccccc2c2ccccc2n1-c1cccnc1] | D09 | 24 | 5-(Pyridin-3-yl)phenanthridin-6(5H)-one | 273 |
| 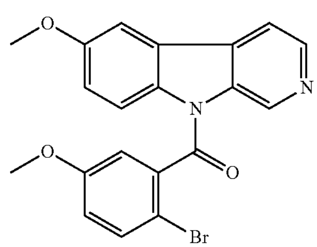 [SMILES: COc1ccc(Br)c(C(=O)n2c3ccc(OC)cc3c3ccncc32)c1] | D14 | 13 | (2-Bromo-5-methoxyphenyl)(6-methoxy-9H-pyrido[3,4-b]indol-9-yl)methanone | 411/413 (bromo pattern) |
| | | 18 | (3-Bromophenyl)(3-methylpyrazolo[3,4-b]indol-8(1H)-yl)methanone | 354/356 bromo pattern |

TABLE 1-continued

Compounds of the present invention.

| Structure | ID | Ex. | IUPAC | MS (ES+) [M + H]: m/e |
|---|---|---|---|---|
| | | 19 | (4-Methoxyphenyl)(3-methylpyrazolo[3,4-b]indol-8(1H)-yl)methanone | 323 |
| | | 20 | (3-Methylpyrazolo[3,4-b]indol-8(1H)-yl)(phenyl)methanone | 276 |
| | | 21 | (3-Methylpyrazolo[3,4-b]indole-1,8-diyl)bis(phenylmethanone) | 380 |
| | | 22 | (2-Chloropyridin-3-yl)(3-methylpyrazolo[3,4-b]indol-8(1H)-yl)methanone | 311/313 chloro pattern |
| | | 23 | (2-Bromo-6-chlorophenyl)(3-methylpyrazolo[3,4-b]indol-8(1H)-yl)methanone | 388/390 isotope pattern |

In a further embodiment the invention relates to a compound for use as a medicament in the treatment of a disease associated with genotoxic stress-induced IKK/NF-κB activation, wherein the compound is selected from the group provided in Table 1 or Table 2.

TABLE 2

Compounds of the present invention for use as a medicament.

| Structure | Ex. | IUPAC | [M + H]: m/e |
|---|---|---|---|
| 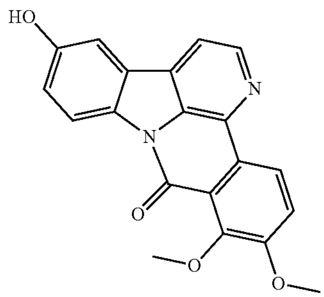 [SMILES: COc1ccc2c(c1OC)c(=O)n1c3ccc(O)cc3c3ccnc2c31] | 45 (ID MW01) | 12-hydroxy-6,7-dimethoxy-8H-benzo[c]indolo[3,2,1-ij][1,5]naphthyridin-8-one | 347 |
| 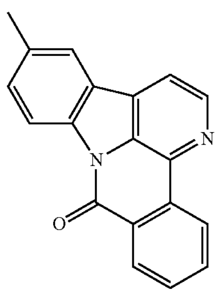 [SMILES: Cc1ccc2c(c1)c1ccnc3c4ccccc4c(=O)n2c13] | C3 | 12-methyl-8H-benzo[c]indolo[3,2,1-ij][1,5]naphthyridin-8-one | 285 |
| 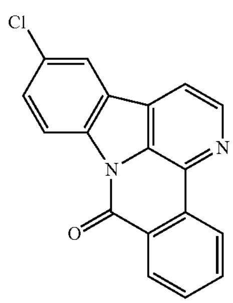 [SMILES: O=c1c2ccccc2c2nccc3c4cc(Cl)ccc4n1c32] | C4 | 12-chloro-8H-benzo[c]indolo[3,2,1-ij][1,5]naphthyridin-8-one | 305 |
| 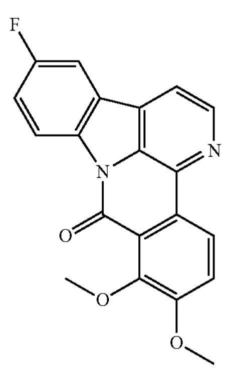 [SMILES: COc1ccc2c(c1OC)c(=O)n1c3ccc(F)cc3c3ccnc2c31] | C2 | 12-fluoro-6,7-dimethoxy-8H-benzo[c]indolo[3,2,1-ij][1,5]naphthyridin-8-one | 349 |

TABLE 2-continued

Compounds of the present invention for use as a medicament.

| Structure | Ex. | IUPAC | [M + H]: m/e |
|---|---|---|---|
| 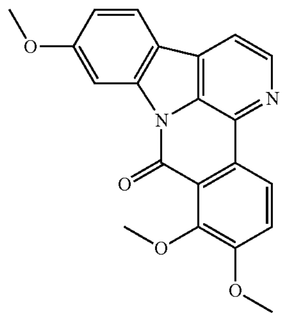 | C1 | 6,7,11-trimethoxy-8H-benzo[c]indolo[3,2,1-ij][1,5]naphthyridin-8-one | 361 |
| 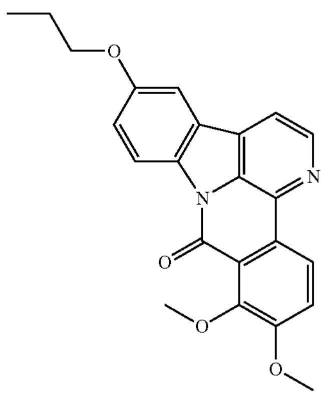 [SMILES: CCCOc1ccc2c(c1)c1ccnc3c4ccc(OC)c(OC)c4c(=O)n2c13] | B7 | 6,7-dimethoxy-12-propoxy-8H-benzo[c]indolo[3,2,1-ij][1,5]naphthyridin-8-one | 389 |
| 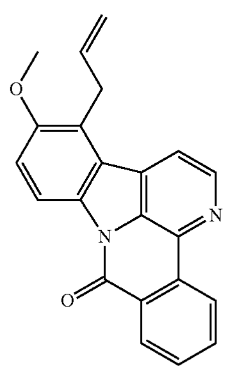 [SMILES: C=CCc1c(OC)ccc2c1c1ccnc3c4ccccc4c(=O)n2c13] | C5 | 13-allyl-12-methoxy-8H-benzo[c]indolo[3,2,1-ij][1,5]naphthyridin-8-one | 341 |
| 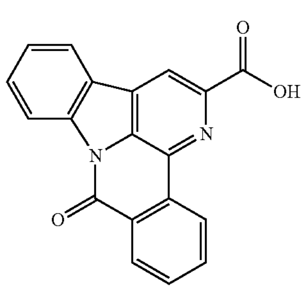 [SMILES: O=C(O)c1cc2c3ccccc3n3c(=O)c4ccccc4c(n1)c23] | A5 | 8-oxo-8H-benzo[c]indolo[3,2,1-ij][1,5]naphthyridine-2-carboxylic acid | 315 |

TABLE 2-continued
Compounds of the present invention for use as a medicament.
| Structure | Ex. | IUPAC | [M + H]: m/e |
|---|---|---|---|
| 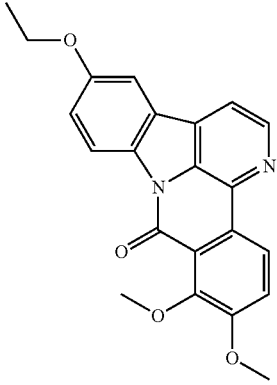 [SMILES: CCOc1ccc2c(c1)c1ccnc3c4ccc(OC)c(OC)c4c(=O)n2c13] | B5 | 12-ethoxy-6,7-dimethoxy-8H-benzo[c]indolo[3,2,1-ij][1,5]naphthyridin-8-one | 375 |
| 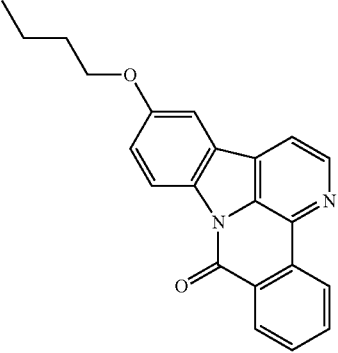 [SMILES: CCCCOc1ccc2c(c1)c1ccnc3c4ccccc4c(=O)n2c13] | B4 | 12-butoxy-8H-benzo[c]indolo[3,2,1-ij][1,5]naphthyridin-8-one | 343 |
| 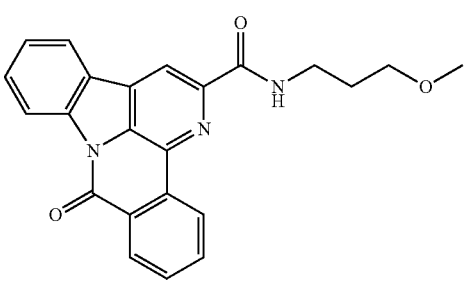 [SMILES: COCCCNC(=O)c1cc2c3ccccc3n3c(=O)c4ccccc4c(n1)c23] | A7 | N-(3-methoxypropyl)-8-oxo-8H-benzo[c]indolo[3,2,1-ij][1,5]naphthyridine-2-carboxamide | 386 |
| 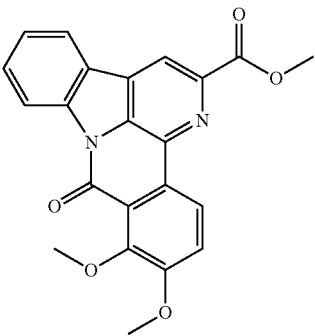 [SMILES: COC(=O)c1cc2c3ccccc3n3c(=O)c4c(OC)c(OC)ccc4c(n1)c23] | A4 | methyl 6,7-dimethoxy-8-oxo-8H-benzo[c]indolo[3,2,1-ij][1,5]naphthyridine-2-carboxylate | 389 |

TABLE 2-continued

Compounds of the present invention for use as a medicament.

| Structure | Ex. | IUPAC | [M + H]: m/e |
|---|---|---|---|
| 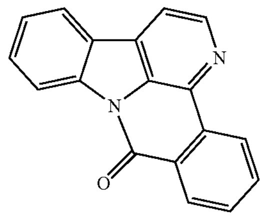 [SMILES: O=c1c2ccccc2c2nccc3c4ccccc4n1c32] | A6 (= Ex.16; ID: D10) | 8H-Benzo[c]indolo[3,2,1-ij][1,5]naphthyridin-8-one | 271 |
| 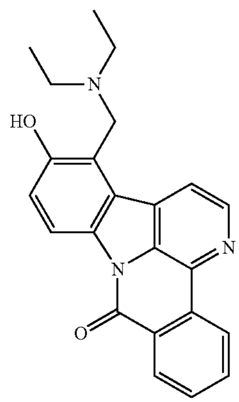 [SMILES: CCN(CC)Cc1c(O)ccc2c1c1ccnc3c4ccccc4c(=O)n2c13] | B2 | 13-((diethylamino)methyl)-12-hydroxy-8H-benzo[c]indolo[3,2,1-ij][1,5]naphthyridin-8-one | 372 |
| 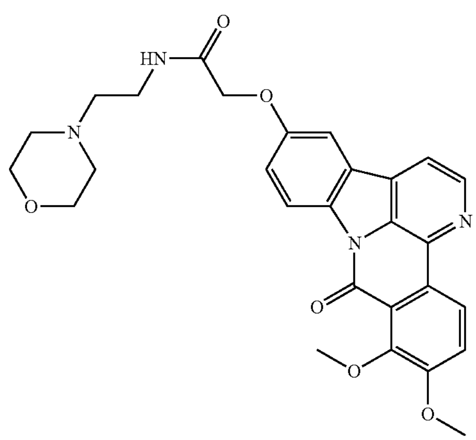 [SMILES: COc1ccc2c(c1OC)c(=O)n1c3ccc(OCC(=O)NCCN4CCOCC4)cc3c3ccnc2c31] | B3 | 2-((6,7-dimethoxy-8-oxo-8H-benzo[c]indolo[3,2,1-ij][1,5]naphthyridin-12-yl)oxy)-N-(2-morpholinoethyl)acetamide | 517 |
| 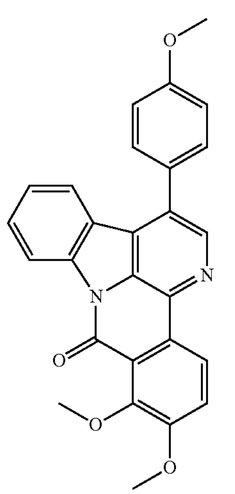 [SMILES: COc1ccc(-c2cnc3c4ccc(OC)c(OC)c4c(=O)n4c5ccccc5c2c34)cc1] | A3 | 6,7-dimethoxy-1-(4-methoxyphenyl)-8H-benzo[c]indolo[3,2,1-ij][1,5]naphthyridin-8-one | 437 |

TABLE 2-continued

Compounds of the present invention for use as a medicament.

| Structure | Ex. | IUPAC | [M + H]: m/e |
|---|---|---|---|
| 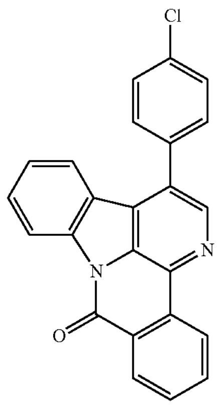 [SMILES: O=c1c2ccccc2c2ncc(-c3ccc(Cl)cc3)c3c4ccccc4n1c23] | A1 | 1-(4-chlorophenyl)-8H-benzo[c]indolo[3,2,1-ij][1,5]naphthyridin-8-one | 381 |
| 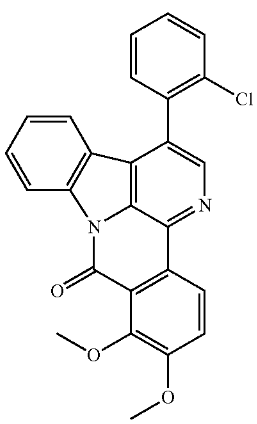 [SMILES: COc1ccc2c(c1OC)c(=O)n1c3ccccc3c3c(-c4ccccc4Cl)cnc2c31] | A2 | 1-(2-chlorophenyl)-6,7-dimethoxy-8H-benzo[c]indolo[3,2,1-ij][1,5]naphthyridin-8-one | 441 |
| | | 12-(2-(2-aminoethoxy)ethoxy)-6,7-dimethoxy-8H-benzo[c]indolo[3,2,1-ij][1,5]naphthyridin-8-one | 434 |
| 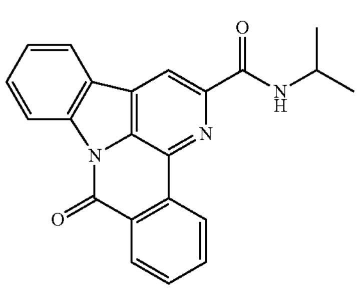 [SMILES: CC(C)NC(=O)c1cc2c3ccccc3n3c(=O)c4ccccc4c(n1)c23] | A8 | N-isopropyl-8-oxo-8H-benzo[c]indolo[3,2,1-ij][1,5]naphthyridine-2-carboxamide | 356 |

TABLE 2-continued

Compounds of the present invention for use as a medicament.

| Structure | Ex. | IUPAC | [M + H]: m/e |
|---|---|---|---|
| 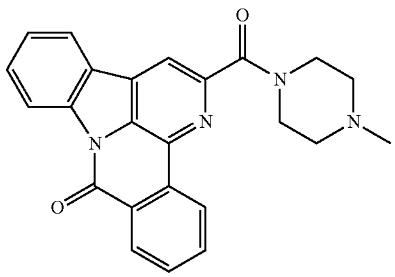 [SMILES: CN1CCN(C(=O)c2cc3c4ccccc4n4c(=O)c5ccccc5c(n2)c34)CC1] | B1 | 2-(4-methylpiperazine-1-carbonyl)-8H-benzo[c]indolo[3,2,1-ij][1,5]naphthyridin-8-one | 397 |
| 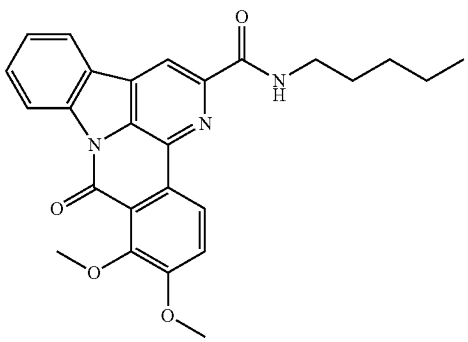 [SMILES: CCCCCNC(=O)c1cc2c3ccccc3n3c(=O)c4c(OC)c(OC)ccc4c(n1)c23] | B6 | 6,7-dimethoxy-8-oxo-N-pentyl-8H-benzo[c]indolo[3,2,1-ij][1,5]naphthyridine-2-carboxamide | 444 |
| 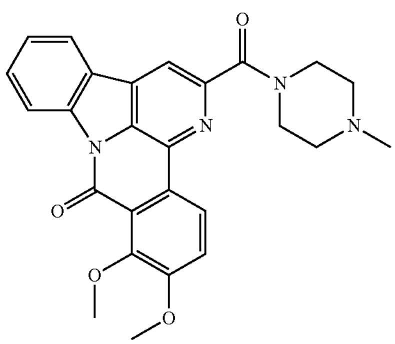 [SMILES: COc1ccc2c(c1OC)c(=O)n1c3ccccc3c3cc(C(=O)N4CCN(C)CC4)nc2c31] | B8 | 6,7-dimethoxy-2-(4-methylpiperazine-1-carbonyl)-8H-benzo[c]indolo[3,2,1-ij][1,5]naphthyridin-8-one | 457 |

In a preferred embodiment the present invention relates to a compound for use as a medicament according to any one of the preceding claims, wherein the compound is

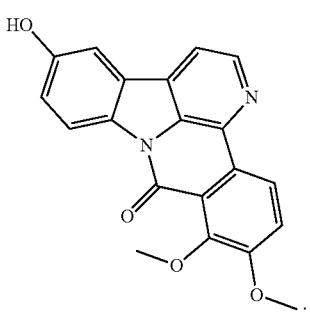 [SMILES: COc1ccc2c(c1OC)c(=O)n1c3ccc(O)cc3c3ccnc2c31 ; "."]

In further preferred embodiments of the invention the Formulae I-VII may be defined by the ring structures B or C as disclosed in FIG. 12 (D). These preferred structures may be incorporated into one or more of Formulae I-VII, whilst the remaining substituents of the Formulae preferably remain as disclosed above.

In another preferred embodiment of the present invention the disease to be treated is associated with genotoxic stress-induced IKK/NF-κB activation.

In another preferred embodiment of the present invention the disease to be treated is cancer.

In another preferred embodiment of the invention the cancer is associated with genotoxic stress-induced IKK/NF-κB activation.

In another preferred embodiment of the invention the compound is more effective in inhibiting NF-κB-signaling induced by genotoxic stress compared to inhibiting NF-κB-signaling induced by TNF-alpha and/or IL-1β. This feature relates to a functional feature of the compound described herein suitable for definition of the compound and for differentiation from other compounds described in the art.

Another preferred embodiment of the invention relates to treatment of a disease, which is associated with genomic instability due to defective DNA-repair mechanisms. In a preferred embodiment of the invention the defects of the DNA-repair mechanisms are based on genetic or epigenetic alterations of one or more DNA repair genes.

In another preferred embodiment of the present invention, the cancer to be treated is associated with NF-κB-mediated resistance to therapy-induced tumor cell apoptosis.

In another preferred embodiment of the present invention the compound is administered in combination with one or more other cancer therapies, preferably DNA damage-inducing cancer therapies.

In a preferred embodiment of the present invention the compound is administered in combination with irradiation therapy. In another preferred embodiment of the present invention the compound is administered in combination with genotoxic stress-inducing chemotherapy.

Another preferred embodiment of the present invention relates to the use of a compound according to the present invention in an in vitro method for the inhibition of genotoxic stress-induced NF-κB signaling, preferably in a cell based assay.

In another preferred embodiment of the present invention the compound of the present invention is used in an in vitro method for the inhibition of DNA repair mechanisms, preferably in a cell based assay.

Furthermore, the present invention relates to a pharmaceutical composition for the treatment of a subject afflicted by a disease associated with genotoxic stress-induced IKK/NF-κB activation, said composition comprising a compound according to the present invention and a pharmaceutically acceptable carrier substance.

Further Embodiments of the Invention

In a preferred embodiment, the invention relates to a compound according to Formula I for use as a medicament in the treatment of a disease associated with genotoxic stress-induced IKK/NF-κB activation, wherein
R1=H, O;
R2=from 0-4, can be the same or different, H, OH, halogen, preferably Br, Cl or F, C1-C7 alkyl, alkenyl, alkynyl, alkoxy, carbonyl, carboxyl, alkoxycarbonyl, amine,
or wherein R2 is alkoxyamine, alkoxyamide, such as

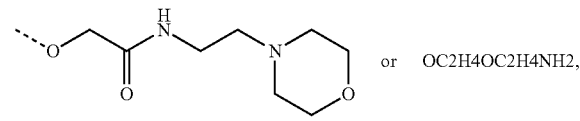 or OC2H4OC2H4NH2, wherein at least one of R2 from 0-4 is not H;
R3=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms;
X1, X2, X3=N or C; preferably C,
ring A is a heteroaromatic cyclic structure of 5 or 6 members, comprising 1 or 2 heteroatoms selected from O and/or N, preferably forming a pyrazolyl, imidazolyl, pyridyl, pyrimidyl, pyridazyl, pyrazinyl ring, more preferably selected from the group consisting of

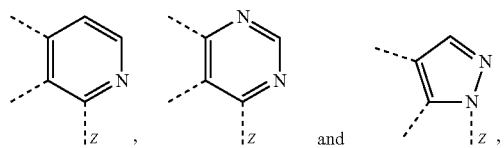

wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3;
the bond z may be present or not present, wherein when bond z is not present:
the C of bond z of ring C is substituted with R3, and
X3 of the A ring is substituted with H, OH, halogen, preferably Br, Cl or F, C1-C7 alkyl, alkenyl, alkynyl, alkoxy, carbonyl, carboxyl, alkoxycarbonyl, amine.

In a preferred embodiment, the invention relates to a compound according to Formula I for use as a medicament in the treatment of a disease associated with genotoxic stress-induced IKK/NF-κB activation, wherein
R1=H, O;
R2=from 0-4, can be the same or different, H, OH, halogen, preferably Br, Cl or F, C1-C7 alkyl, alkenyl, alkynyl, alkoxy, carbonyl, carboxyl, alkoxycarbonyl, amine,
or wherein R2 is alkoxyamine, alkoxyamide, such as

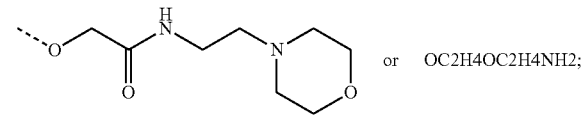 or OC2H4OC2H4NH2;

R3=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms;
X1, X2=N or C; preferably C;
X3=C;
ring A is a heteroaromatic cyclic structure of 5 or 6 members, comprising 1 or 2 heteroatoms selected from O and/or N, preferably forming a pyrazolyl, imidazolyl, pyridyl, pyrimidyl, pyridazyl, pyrazinyl ring, more preferably selected from the group consisting of

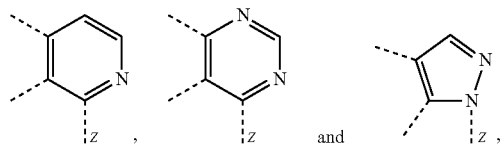

wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3;

the bond z may be present or not present, wherein when bond z is not present:

the C of bond z of ring C is substituted with R3, and

X3 of the A ring is substituted with H, OH, halogen, preferably Br, Cl or F, C1-C7 alkyl, alkenyl, alkynyl, alkoxy, carbonyl, carboxyl, alkoxycarbonyl, amine.

In a preferred embodiment, the invention relates to a compound according to Formula I for use as a medicament in the treatment of a disease associated with genotoxic stress-induced IKK/NF-κB activation, wherein

R1=O;

R2=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

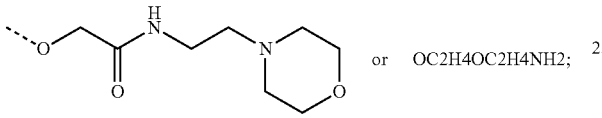 or OC2H4OC2H4NH2;

R3=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms;

X1, X2, X3=N or C; preferably C;

ring A is a heteroaromatic cyclic structure of 5 or 6 members, comprising 1 or 2 heteroatoms selected from O and/or N, preferably forming a pyrazolyl, imidazolyl, pyridyl, pyrimidyl, pyridazyl, pyrazinyl ring, more preferably selected from the group consisting of

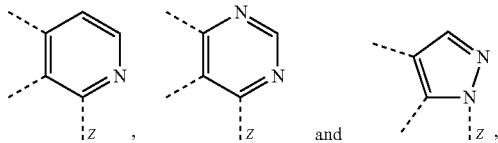

wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3;

the bond z may be present or not present, wherein when bond z is not present:

the C of bond z of ring C is substituted with R3, and

X3 of the A ring is substituted with H, OH, halogen, preferably Br, Cl or F, C1-C7 alkyl, alkenyl, alkynyl, alkoxy, carbonyl, carboxyl, alkoxycarbonyl, amine.

In a preferred embodiment, the invention relates to a compound according to Formula I for use as a medicament in the treatment of a disease associated with genotoxic stress-induced IKK/NF-κB activation, wherein

R1=O;

R2=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

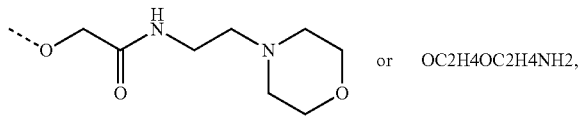 or OC2H4OC2H4NH2, wherein at least one of R2 from 0-4 is not H;

R3=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms;

X1, X2, X3=N or C; preferably C;

ring A is a heteroaromatic cyclic structure of 5 or 6 members, comprising 1 or 2 heteroatoms selected from O and/or N, preferably forming a pyrazolyl, imidazolyl, pyridyl, pyrimidyl, pyridazyl, pyrazinyl ring, more preferably selected from the group consisting of

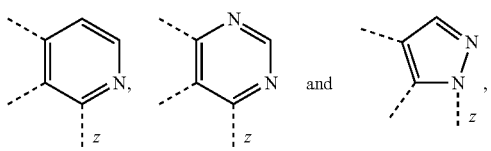

wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3;

the bond z may be present or not present, wherein when bond z is not present:

the C of bond z of ring C is substituted with R3, and

X3 of the A ring is substituted with H, OH, halogen, preferably Br, Cl or F, C1-C7 alkyl, alkenyl, alkynyl, alkoxy, carbonyl, carboxyl, alkoxycarbonyl, amine.

In a preferred embodiment, the invention relates to a compound according to Formula I for use as a medicament in the treatment of a disease associated with genotoxic stress-induced IKK/NF-κB activation, wherein

R1=O;

R2=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

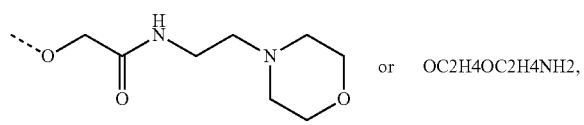 or OC2H4OC2H4NH2, wherein at least one of R2 from 0-4 is not H;

R3=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms;

X1, X2=N or C; preferably C;

X3=C;

ring A is a heteroaromatic cyclic structure of 5 or 6 members, comprising 1 or 2 heteroatoms selected from O and/or N, preferably forming a pyrazolyl, imidazolyl, pyridyl, pyrimidyl, pyridazyl, pyrazinyl ring, more preferably selected from the group consisting of

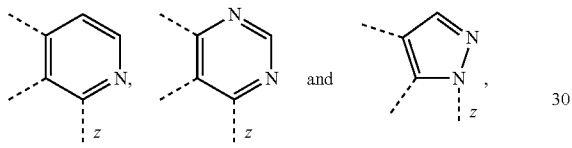

wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3;

the bond z may be present or not present, wherein when bond z is not present:

the C of bond z of ring C is substituted with R3, and

X3 of the A ring is substituted with H, OH, halogen, preferably Br, Cl or F, C1-C7 alkyl, alkenyl, alkynyl, alkoxy, carbonyl, carboxyl, alkoxycarbonyl, amine.

A further aspect of the invention relates to a compound, and preferably its medical use as described herein, according to Formula I, Formula I

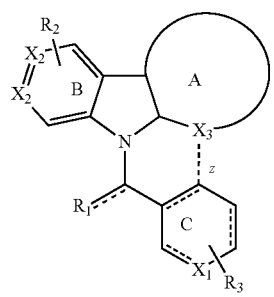

wherein:

R1=O;

R2=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

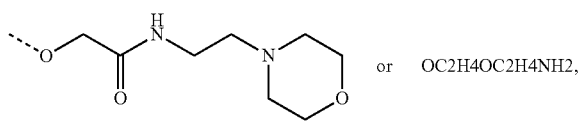 or OC2H4OC2H4NH2, wherein at least one of R2 from 0-4 is not H;

R3=from 0-4, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms;

X1, X2=N or C; preferably C;

ring A is a heteroaromatic cyclic structure of 5 or 6 members, comprising 1 or 2 heteroatoms selected from O and/or N, preferably forming a pyrazolyl, imidazolyl, pyridyl, pyrimidyl, pyridazyl, pyrazinyl ring, more preferably selected from the group consisting of

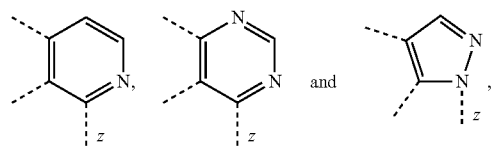

wherein when ring A is a cyclic structure of 5 members X3=N and when ring A is a cyclic structure of 6 members X3=C, wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3;

the bond z may be present or not present, wherein when bond z is not present:

the C of bond z of ring C is substituted with R3, and

X3 of the A ring is substituted with H, OH, halogen, preferably Br, Cl or F, C1-C7 alkyl, alkenyl, alkynyl, alkoxy, carbonyl, carboxyl, alkoxycarbonyl, amine.

A further aspect of the invention relates to a compound, and preferably its medical use as described herein, according to Formula II,

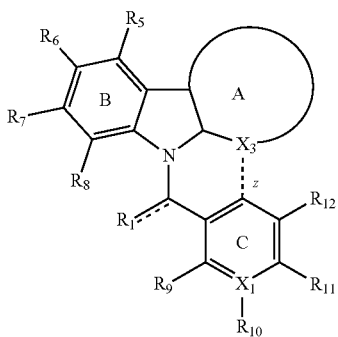

Formula II wherein
R1=O;
R5=H, halogen, preferably Cl, Br, F, C1-C5, preferably C1-C3, alkyl, alkenyl, alkoxy, amine, most preferably H;
R6=H, OH, halogen, preferably Cl, Br, F, C1-C5, preferably C1-C3, alkyl, alkoxy, preferably methoxy, or alkoxyamine, alkoxyamide, such as

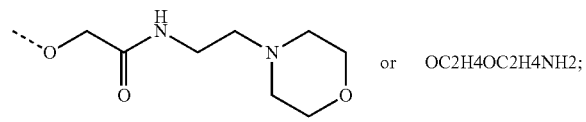 or OC2H4OC2H4NH2;

R7=H, halogen, preferably Cl, Br, F, C1-C5, preferably C1-C3, alkyl, alkoxy, preferably methoxy;
R8=H, halogen, preferably Cl, Br, F, C1-C5, preferably C1-C3, alkyl, alkoxy, preferably methoxy, most preferably H;
wherein at least one of R5 to R8 is not H;
R9=H, halogen, preferably Cl, Br, F, C1-C5, preferably C1-C3, alkyl, alkoxy, preferably methoxy;
R10=H, halogen, preferably Cl, Br, F, C1-C5, preferably C1-C3, alkyl, alkoxy, preferably methoxy;
R11=H, halogen, preferably Cl, Br, F, C1-C5, preferably C1-C3, alkyl, alkoxy, preferably methoxy, carboxyl;
R12=H, halogen, preferably Cl, Br, F, C1-C5, preferably C1-C3, alkyl, alkoxy, preferably methoxy;
or wherein when X1 is C, R9 and R10, R10 and R11, R11 and R12, or R12 and the C in the position of bond z of ring C, form an optionally aromatic cyclic structure of 5 or 6 members, comprising 0, 1, or 2 heteroatoms, preferably O or N, more preferably 2 O atoms, or forming phenyl;
X1, X3=N or C;
ring A is a heteroaromatic cyclic structure of 5 or 6 members, comprising 1 or 2 heteroatoms selected from O and/or N, preferably forming a pyrazolyl, imidazolyl, pyridyl, pyrimidyl, pyridazyl, pyrazinyl ring, more preferably selected from the group consisting of

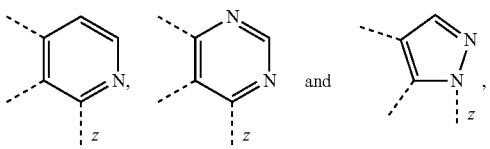

wherein when ring A is a cyclic structure of 5 members X3=N and when ring A is a cyclic structure of 6 members X3=C,
wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3;
the bond z may be present or not present, wherein when bond z is not present:
the C in the position of bond z of ring C is potentially substituted with halogen, preferably Cl, Br, F, C1-C5, preferably C1-C3, alkyl,
and X3 of the A ring is optionally substituted with H, C1-C5, preferably C1-C3, alkyl, or when X3 is C potentially with H, C1-C5, preferably C1-C3, alkyl, OH, halogen, preferably Br, Cl or F.

A further aspect of the invention relates to a compound, and preferably its medical use as described herein, according to Formula III,

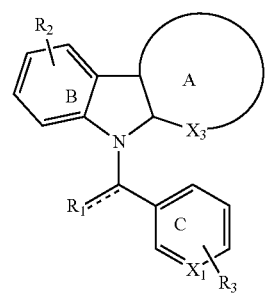

wherein the substituents of Formula III are:
R1=O;
R2=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine,
or wherein R2 is alkoxyamine, alkoxyamide, such as

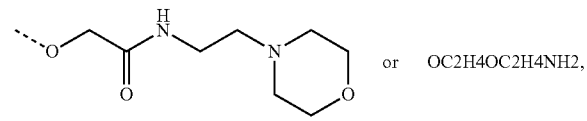 or OC2H4OC2H4NH2, wherein at least one of R2 from 0-4 is not H;
R3=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents form an optionally aromatic cyclic structure of 5 or 6 members, optionally comprising 0, 1, or 2 heteroatoms, preferably O or N, more preferably 2 O atoms, or forming phenyl;
X1, X3=N or C;
ring A is a heteroaromatic structure of 5 members, comprising 1 or 2 N atoms, wherein X3 must be N, preferably forming a pyrazolyl or imidazolyl ring, preferably

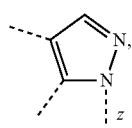

or ring A is a heteroaromatic structure of 6 members, comprising 1 or 2 N atom, wherein X3 must be C, preferably selected from the group consisting of

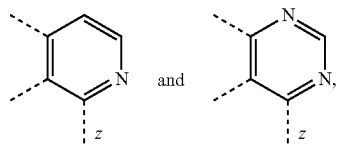

wherein the cyclic structure of ring A is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3.

A further aspect of the invention relates to a compound, and preferably its medical use as described herein, according to Formula III-a,

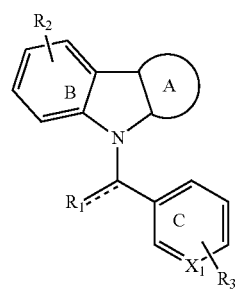

Formula III-a wherein
R1=O;
R2=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

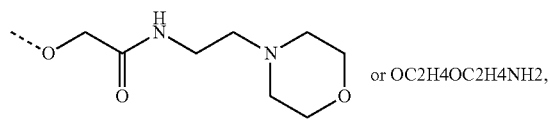

or OC2H4OC2H4NH2, wherein at least one of R2 from 0-4 is not H;
R3=from 0-4, preferably 0, 1 or 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents form an optionally aromatic cyclic structure of 5 or 6 members, optionally comprising 0, 1, or 2 heteroatoms, preferably O or N, more preferably 2 O atoms, or forming phenyl;

X1=N or C;

ring A is a heteroaromatic structure of 5 or 6 members, comprising 1 or 2 N atoms, preferably forming a pyrazolyl, imidazolyl, pyridyl, pyrimidyl, pyridazyl, pyrazinyl ring, more preferably selected from the group consisting of

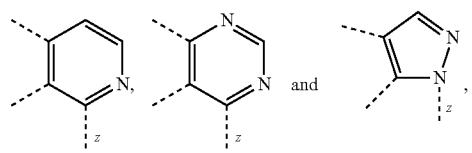

wherein said cyclic structure is optionally substituted with 0-3 substituents that can be the same or different, selected from H, OH, halogen, preferably Br, Cl or F, C1-C7 alkyl, alkenyl, alkynyl, alkoxy, carbonyl, such as CO-phenyl, carboxyl, alkoxycarbonyl, amine, aryl, such as phenyl (optionally substituted with halogen, C1-C3 alkyl, alkoxy, amine), alkoxyamine, such as CONHC3H6OCH3.

A further aspect of the invention relates to a compound, and preferably its medical use as described herein, according to Formula VIII,

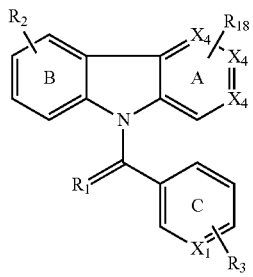

Formula VIII wherein
R1=O;
R2=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

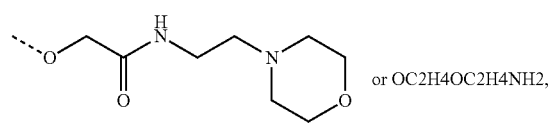

or OC2H4OC2H4NH2, wherein at least one of R2 from 0-4 is not H;
R3=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms, or form phenyl;
X1=N or C, preferably C;
X4=N or C, whereby at least one X4 is N;

R16=can be 0-3, preferably 0, 1, 2, the same or different, H, halogen, preferably Cl, Br, F, C1-C5, preferably C1-C3, alkyl, alkoxy, preferably methoxy.

A further aspect of the invention relates to a compound, and preferably its medical use as described herein, according to Formula IX,

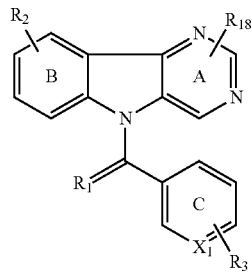

Formula IX wherein
R1=O;
R2=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

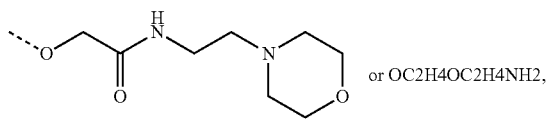 or OC2H4OC2H4NH2, wherein at least one of R2 from 0-4 is not H;
R3=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms, or form phenyl;
X1=N or C, preferably C;
R16=can be 0-3, preferably 0, 1, 2, the same or different, H, halogen, preferably Cl, Br, F, C1-C5, preferably C1-C3, alkyl, alkoxy, preferably methoxy.

A further aspect of the invention relates to a compound, and preferably its medical use as described herein, according to Formula X,

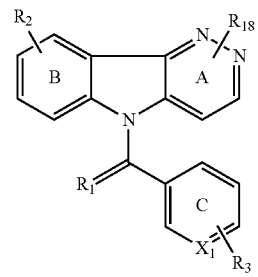

Formula X wherein
R1=O;
R2=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

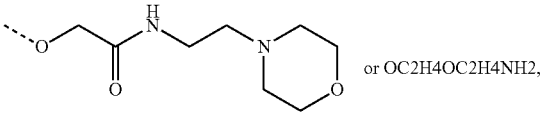 or OC2H4OC2H4NH2, wherein at least one of R2 from 0-4 is not H;
R3=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms, or form phenyl;
X1=N or C, preferably C;
R16=can be 0-3, preferably 0, 1, 2, the same or different, H, halogen, preferably Cl, Br, F, C1-C5, preferably C1-C3, alkyl, alkoxy, preferably methoxy.

In a preferred embodiment the invention relates to a compound, and preferably its medical use as described herein, according to Formula VI,

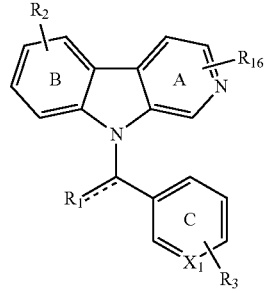

Formula VI wherein
R1=O;
R2=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein R2 is alkoxyamine, alkoxyamide, such as

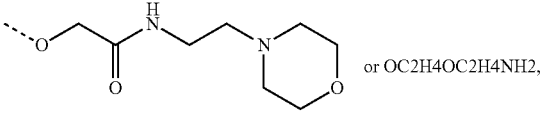 or OC2H4OC2H4NH2, wherein at least one of R2 from 0-4 is not H;
R3=from 0-4, preferably 0, 1, 2, can be the same or different, H, OH, halogen, preferably Br, Cl or F, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms, preferably O or N, more preferably 2 O atoms, or form phenyl;
X1=N or C;
R16=can be 0-3, preferably 0, 1, 2, the same or different, H, halogen, preferably Cl, Br, F, C1-C5, preferably C1-C3, alkyl, alkoxy, preferably methoxy.

In a preferred embodiment the compound of the invention is selected from the group provided in Table 1 and/or Table 3. In a preferred embodiment the invention relates to the compounds in table 1 and/or table 3 as a medicament in the treatment of a disease associated with genotoxic stress-induced IKK/NF-κB activation.

TABLE 3

Further compounds of the present invention.

| Structure | Ex. | IUPAC | MS (ES+) [M + H]: m/e |
|---|---|---|---|
| 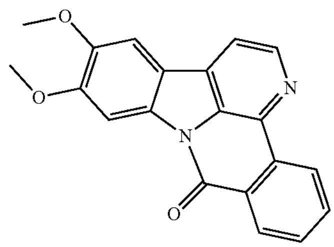 [SMILES: COc1cc2c3ccnc4c5ccccc5c(=O)n(c2cc1OC)c34] | 27 | 11,12-dimethoxy-8H-benzo[c]indolo[3,2,1-ij][1,5]naphthyridin-8-one | 331 |
| 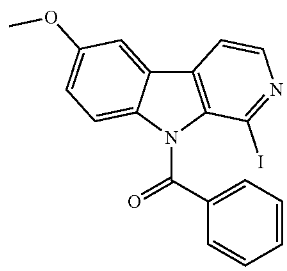 [SMILES: COc1ccc2c(c1)c1ccnc(I)c1n2C(=O)c1ccccc1] | 28 | (1-iodo-6-methoxy-9H-pyrido[3,4-b]indol-9-yl)(phenyl)methanone | 428 |
| 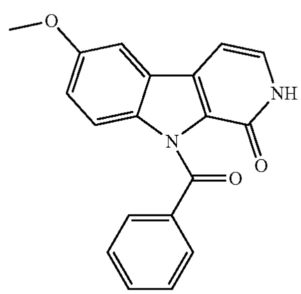 [SMILES: COc1ccc2c(c1)c1cc[nH]c(=O)c1n2C(=O)c1ccccc1] | 29 | 9-benzoyl-6-methoxy-2,9-dihydro-1H-pyrido[3,4-b]indol-1-one | 319 |
| 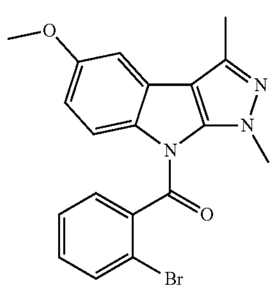 | 30 | (2-bromophenyl)(5-methoxy-1,3-dimethylpyrazolo[3,4-b]indol-8(1H)-yl)methanone | 398/400 isotope pattern |
| 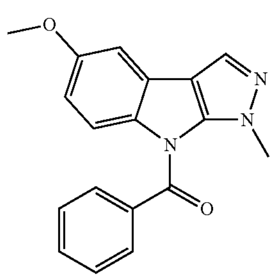 | 31 | (5-methoxy-1-methylpyrazolo[3,4-b]indol-8(1H)-yl)(phenyl)methanone | 306 |

TABLE 3-continued

Further compounds of the present invention.

| Structure | Ex. | IUPAC | MS (ES+) [M + H]: m/e |
|---|---|---|---|
| 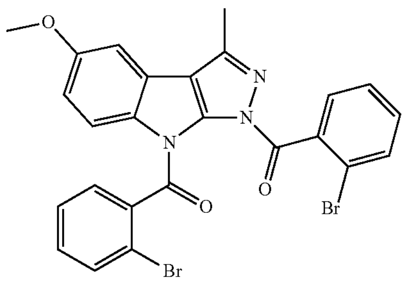 [SMILES: COc1ccc2c(c1)c1c(C)nn(C(=O)c3ccccc3Br)c1n2C(=O)c1ccccc1Br] | 32 | (5-methoxy-3-methylpyrazolo[3,4-b]indole-1,8-diyl)bis((2-bromophenyl)methanone) | 566/568/570 isotope pattern |
| 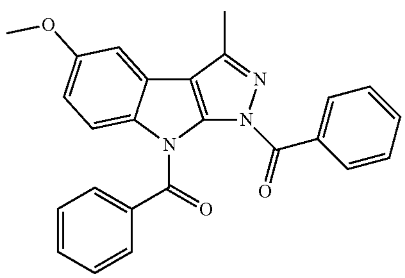 [SMILES: COc1ccc2c(c1)c1c(C)nn(C(=O)c3ccccc3)c1n2C(=O)c1ccccc1] | 33 | (5-methoxy-3-methylpyrazolo[3,4-b]indole-1,8-diyl)bis(phenylmethanone) | 410 |
| 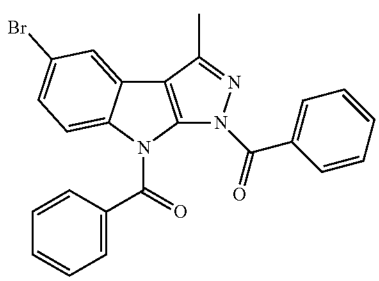 [SMILES: Cc1nn(C(=O)c2ccccc2)c2c1c1cc(Br)ccc1n2C(=O)c1ccccc1] | 34 | (5-bromo-3-methylpyrazolo[3,4-b]indole-1,8-diyl)bis(phenylmethanone) | 458 isotope pattern |
| 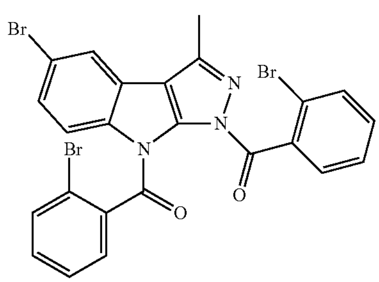 [SMILES: Cc1nn(C(=O)c2ccccc2Br)c2c1c1cc(Br)ccc1n2C(=O)c1ccccc1Br] | 35 | (5-bromo-3-methylpyrazolo[3,4-b]indole-1,8-diyl)bis((2-bromophenyl)methanone) | 616 isotope pattern |
| 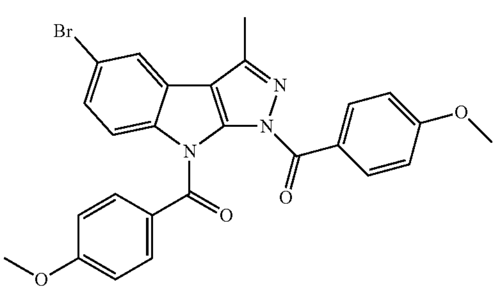 | 36 | (5-bromo-3-methylpyrazolo[3,4-b]indole-1,8-diyl)bis((4-methoxyphenyl)methanone) | 518/520 isotope pattern |

TABLE 3-continued
Further compounds of the present invention.
| Structure | Ex. | IUPAC | MS (ES+) [M + H]: m/e |
|---|---|---|---|
| 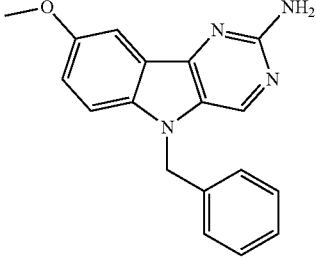 [SMILES: COc1ccc2c(c1)c1nc(N)ncc1n2Cc1ccccc1] | 37 | 5-benzyl-8-methoxy-5H-pyrimido[5,4-b]indol-2-amine | 305 |
| 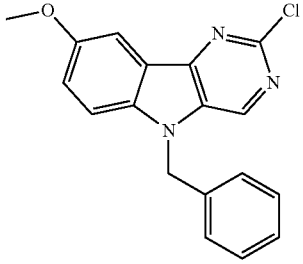 [SMILES: COc1ccc2c(c1)c1nc(Cl)ncc1n2Cc1ccccc1] | 38 | 5-benzyl-2-chloro-8-methoxy-5H-pyrimido[5,4-b]indole | 324 |
| 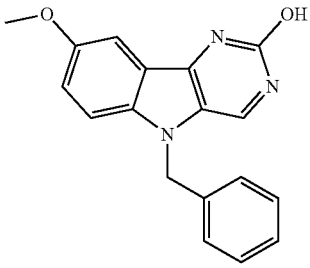 [SMILES: COc1ccc2c(c1)c1nc(O)ncc1n2Cc1ccccc1] | 39 | 5-benzyl-8-methoxy-5H-pyrimido[5,4-b]indol-2-ol | 306 |
| 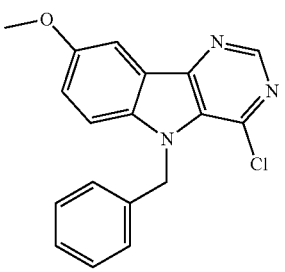 [SMILES: COc1ccc2c(c1)c1ncnc(Cl)c1n2Cc1ccccc1] | 40 | 5-benzyl-4-chloro-8-methoxy-5H-pyrimido[5,4-b]indole | 324 |
| 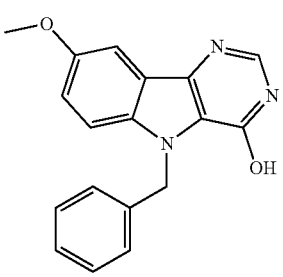 [SMILES: COc1ccc2c(c1)c1ncnc(O)c1n2Cc1ccccc1] | 41 | 5-benzyl-8-methoxy-5H-pyrimido[5,4-b]indol-4-ol | 306 |

TABLE 3-continued

Further compounds of the present invention.

| Structure | Ex. | IUPAC | MS (ES+) [M + H]: m/e |
|---|---|---|---|
| 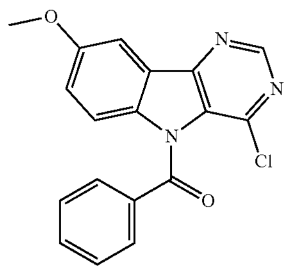 [SMILES: COc1ccc2c(c1)c1ncnc(Cl)c1n2C(=O)c1ccccc1] | 42 | (4-chloro-8-methoxy-5H-pyrimido[5,4-b]indol-5-yl)(phenyl)methanone | 338 |
| 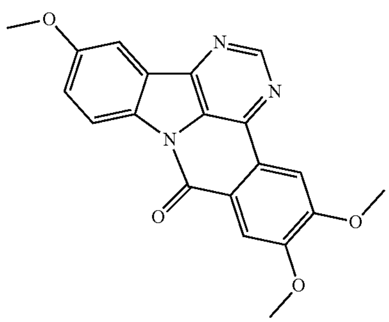 | 43 | 5,6,12-trimethoxy-8H-dibenzo[b,f]pyrimido[4,5,6-hi]indolizin-8-one | 362 |
| 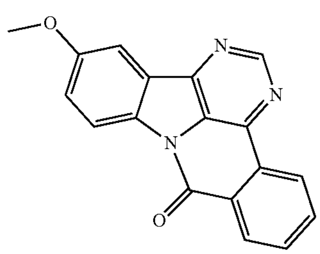 [SMILES: COc1ccc2c(c1)c1ncnc3c4ccccc4c(=O)n2c31] | 44 | 12-methoxy-8H-dibenzo[b,f]pyrimido[4,5,6-hi]indolizin-8-one | 302 |

In a further embodiment the invention relates to a compound for use as a medicament in the treatment of a disease associated with genotoxic stress-induced IKK/NF-κB activation, wherein the compound is selected from the group provided in Table 1, Table 2, Table 3 and/or Table 4.

TABLE 4

Further compounds of the present invention for use as a medicament.

| Structure | Ex. | IUPAC | MS (ES+) [M + H]: m/e |
|---|---|---|---|
| 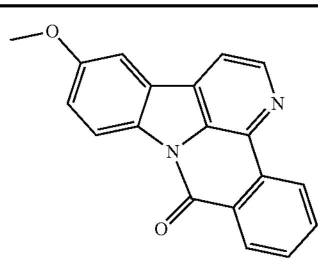 | 25 | 12-methoxy-8H-benzo[c]indolo[3,2,1-ij][1,5]naphthyridin-8-one | 301 |

TABLE 4-continued

Further compounds of the present invention for use as a medicament.

| Structure | Ex. | IUPAC | MS (ES+) [M + H]: m/e |
|---|---|---|---|
| 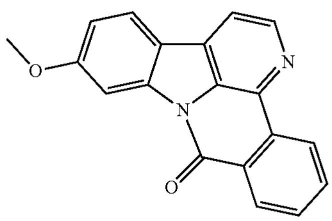 [SMILES: COc1ccc2c3ccnc4c5ccccc5c(=O)n(c2c1)c34] | 26 | 11-methoxy-8H-benzo[c]indolo[3,2,1-ij][1,5]naphthyridin-8-one | 301 |

DETAILED DESCRIPTION OF THE INVENTION

All cited documents of the patent and non-patent literature are hereby incorporated by reference in their entirety.

The invention relates to chemical compounds and their use as a medicament in the treatment of a disease associated with genotoxic stress, preferably a disease associated with genotoxic stress-induced IKK/NF-κB (NF-kappaB) activation.

With respect to the chemical compounds described herein, the term "alkyl" refers to a branched or unbranched saturated hydrocarbon group of 1 to 7 carbon atoms, such as methyl, ethyl, n-propyl, isopropyl, w-butyl, isobutyl, f-butyl, pentyl, hexyl, heptyl, and the like. Preferred alkyl groups have 1 to 7 carbon atoms, more preferably 1 to 4 carbon atoms. Any one or more of the alkyl groups described herein may be "substituted alkyls", wherein one or more hydrogen atoms are substituted with a substituent such as halogen, cycloalkyl, alkoxy, amino, hydroxyl, aryl, or carboxyl.

The term "alkenyl" refers to a straight, branched or cyclic hydrocarbon configuration and combinations thereof, including preferably 2 to 7 carbon atoms, more preferably 2 to 4 carbon atoms, that would form if a hydrogen atom is removed from an alkene, for example resulting in ethenyl, or the like.

The term "alkynyl" refers a straight, branched or cyclic hydrocarbon configuration and combinations thereof, including preferably 2 to 7 carbon atoms, more preferably 2 to 4 carbon atoms, that would form if a hydrogen atom is removed from an alkyne, for example resulting in ethynyl, or the like.

The term "cycloalkyl" refers to a configuration derived from a cycloalkane by removal of an atom of hydrogen, thereby forming preferably cyclopropyl, cyclobutyl, cyclopentyl or cyclohexyl, or the like.

The term "alkoxy" refers to a straight, branched or cyclic hydrocarbon configuration and combinations thereof, including preferably 1 to 7 carbon atoms, more preferably 1 to 4 carbon atoms, that include an oxygen atom at the point of attachment (such as O-alkyl). An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, cyclohexyloxy, and the like.

The term "alkylthio" refers to a configuration containing a carbon-bonded sulfhydryl or sulphydryl (—C—SH or R—SH, wherein R is alkyl), including preferably 1 to 7 carbon atoms, more preferably 1 to 4 carbon atoms, that include an S atom at the point of attachment (such as S-alkyl). An alkylthio may be represented as RS(O)n wherein n=0. The groups RS(O)n, wherein n=1, 2, refer to sulphoxides and sulphones and are also substituents of the compounds of the present invention.

The term "acyl" refers to configurations derived by the removal of one or more hydroxyl groups from an oxoacid containing a double bonded oxygen atom and an alkyl group, forming —RC(=O)—.

The acyl therefore comprises carbonyl, which refers to a radical of the formula —C(=O)—. Carbonyl-containing groups include any substituent containing a carbon-oxygen double bond (C=O), including amides, carboxy groups, esters, ureas, carbamates, carbonates and ketones and aldehydes, such as substituents based on —COR or —RCHO where R is alkyl, heteroalkyl, hydroxyl, or a secondary, tertiary, or quaternary amine.

"Alkoxycarbonyl" refers to an alkoxy substituted carbonyl radical (such as —C(=O)OR), wherein R represents an optionally substituted alkyl, aryl, aralkyl, cycloalkyl, cycloalkylalkyl or similar moiety.

The term "aryl" refers to any carbon-based aromatic group including, but not limited to, benzene, and the like. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "amine" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above. The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

The term 5- or 6-membered ring structure, optionally comprising one or more of N or O, relates preferably a cycloalkyl, cycloalkane and non-aromatic heterocycles (such as morpholine, piperidine, piperazine, thiomorpholine, tetrahydrofuran), aromatic cyclic structures such as phenyl, naphthalene, heterocyclic aromatic rings, such as furan, pyrrole, oxazole, thiophene, thiazole, pyrazole, imidazole, in addition to pyridine, pyrazine, pyrimidine, pyran, thiopyran, oxazine, azepine, thiepine, oxepane, and the like. The 5- or 6-membered cyclic structure preferably forms preferably forming a pyrazolyl, imidazolyl, pyridyl, pyrimidyl, pyridazyl, pyrazinyl ring.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine, phenyl, a substituted phenyl (substituted with, for example, halogen, C1-C3 alkyl, alkoxy, amine), carboxyl, alkoxycarbonyl, amine, aryl.

The term "alkyl amino" refers to alkyl groups as defined above where at least one hydrogen atom is replaced with an amino group.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R).

"Carboxyl" refers to a —COOH radical. Substituted carboxyl refers to —COOR where R is aliphatic, heteroaliphatic, alkyl, heteroalkyl, or a carboxylic acid or ester.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

The term "aralkyl" refers to an aryl group having an alkyl group, as defined above, attached to the aryl group, as defined above. An example of an aralkyl group is a benzyl group.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. In particular, optionally substituted alkyl groups include, by way of example, haloalkyl groups, such as fluoroalkyl groups, including, without limitation, trifluoromethyl groups. These potential optional substituents apply to any group of the formula disclosed herein where an optional substituent is recited. Preferable optional substituents are hydroxyl, alkyl, alkoxy, carbonyl, alkoxycarbonyl, NO2, amine.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

A dashed line in the position of a double bond represents an optional double bond, which may be present or absent.

Protected derivatives of the disclosed compound also are contemplated, for example for use in the synthesis of the disclosed compounds. A variety of suitable protecting groups for use with the disclosed compounds are disclosed in Greene and Wuts Protective Groups in Organic Synthesis; 3rd Ed.; John Wiley & Sons, New York, 1999. In general, protecting groups are removed under conditions which will not affect the remaining portion of the molecule. These methods are well known in the art and include acid hydrolysis, hydrogenolysis and the like.

The compounds of the invention may also exist in various polymorphous forms, for example as amorphous and crystalline polymorphous forms. All polymorphous forms of the compounds of the invention belong within the framework of the invention and are a further aspect of the invention.

The compound of the invention may also comprise deuterium replacing hydrogen. This replacement may in some circumstances lead to improved metabolic stability (Nature Reviews Drug Discovery 15, 219-221 (2016)).

It is understood that substituents and substitution patterns of the compounds described herein can be selected by one of ordinary skill in the art to provide compounds that are chemically stable and that can be readily synthesized by techniques known in the art and further by the methods set forth in this disclosure.

The present invention relates further to pharmaceutically acceptable salts of the compounds described herein. The term "pharmaceutically acceptable salt" refers to salts or esters of the compounds described herein prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. Any chemical compound recited in this specification may alternatively be administered as a pharmaceutically acceptable salt thereof. Also included are acidic salts of inorganic and organic bases, including but not limited to sodium, potassium, ammonium, triethylamine and the like.

"Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

Another aspect of the disclosure includes pharmaceutical compositions prepared for administration to a subject and which include a therapeutically effective amount of one or more of the compounds disclosed herein. In certain embodiments, the pharmaceutical compositions are useful for treating pain. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. Remington's Pharmaceutical Sciences, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

Any references herein to a compound for use as a medicament in the treatment of a medical condition also relate to a method of treating said medical condition comprising the administration of a compound, or composition comprising said compound, to a subject in need thereof, or to the use of a compound, composition comprising said compound, in the treatment of said medical condition.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The present invention also relates to a method of treatment of subjects suffering from the various medical conditions disclosed herein. The method of treatment comprises preferably the administration of a therapeutically effective amount of a compound disclosed herein to a subject in need thereof.

In the context of the present invention, the term "medicament" refers to a drug, a pharmaceutical drug or a medicinal product used to diagnose, cure, treat, or prevent disease. It refers to any substance or combination of substances presented as having properties for treating or preventing disease. The term comprises any substance or combination of substances, which may be used in or administered either with a view to restoring, correcting or modifying physiological functions by exerting a pharmacological, immunological or metabolic action, or to making a medical diagnosis. The term medicament comprises biological drugs, small molecule drugs or other physical material that affects physiological processes.

According to the present invention, the term "treatment" refers to a therapeutic intervention that ameliorates a sign or symptom of a disease or pathological condition after it has begun to develop. As used herein, the term "ameliorating", with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease.

The present invention encompasses both treatment and prophylactic treatment of a subject. A "prophylactic" treatment is a treatment administered to a subject who does not exhibit signs of a disease or exhibits only early signs for the purpose of decreasing the risk of developing pathology.

The term "disease" refers to a particular abnormal condition, a disorder of a structure or function that affects part or all of an organism in the context of the present invention. It refers to any condition that causes pain, dysfunction, distress, or death to the person afflicted and includes injuries, disabilities, disorders, syndromes, infections, isolated symptoms, deviant behaviors, and atypical variations of structure and function. Diseases are associated with dysfunctioning of the body's normal homeostatic processes. Diseases can be acquired, congenital, chronic, acute, genetic, idiopathic, hereditary or inherited. Other equivalent terms in the context of the present invention are illness, disorder, medical condition, syndrome or predisease. A disease can be localized, disseminated or systemic.

When used in the context of the present invention, the term "genotoxic stress" refers to a stress signal, including any given substance, chemical compound, environmental signal, environmental material, irradiation, and/or cellular metabolite, including ROS, which induces damages to genetic material, including all kinds of nucleic acids such as DNA and RNA. The genome is exposed to potentially deleterious genotoxic events during every cell division cycle. This endogenous source of DNA damage results from cellular metabolism or routine errors in DNA replication and recombination. In addition, cellular and organismal exposure to exogenous genotoxic agents including ultraviolet light, oxidative stress, and chemical mutagens, leads to a variety of nucleotide modifications and DNA strand breaks. In order to combat these attacks on the genome, the cell has evolved a response system that induces cell cycle arrest to allow sufficient time to repair the incurred damage. Genotoxic stress induces DNA damage, which leads to the activation of DNA repair. The genotoxic stress response system comprises the DNA repair and activates the appropriate DNA repair pathway, or, in the case of irreparable damage, induces apoptosis. DNA damage in the form of mutations or genomic instability result from genotoxic stress caused by exposure to toxic agents, such as cytotoxic agents administered as anticancer drugs, ultraviolet sun light, background ionizing radiation, chemicals in food and the environment and highly reactive molecules produced within cells during metabolism. Similar types of DNA damage occur in response to various agents and include mutations, removal of bases and nucleotides, formation of dimers, strand breaks, cross-links, and chromosomal aberrations. Some of these types of damage accumulate in nuclear or mitochondrial DNA during aging (e.g., point mutations, single-strand breaks, DNA cross-links, additions/deletions, oxidative damage, and methylated bases).

NF-κB (nuclear factor kappa-light-chain-enhancer of activated B cells) is a protein complex that controls, without limitation, transcription of DNA, cytokine production and survival, differentiation and proliferation of cells. NF-κB is found in almost all animal cell types and is involved in cellular responses to stimuli such as stress, cytokines, free radicals, heavy metals, ultraviolet irradiation, oxidized LDL, and bacterial or viral antigens. NF-κB plays a key role in regulating the immune response to infection and plays various important roles in adaptive and innate immunity. Incorrect regulation of NF-κB has been linked to cancer, inflammatory and autoimmune diseases, septic shock, viral infection, and improper immune system development. NF-κB has also been implicated in processes of synaptic plasticity and memory. All proteins of the NF-κB family share a Rel homology domain in their N-terminus.

A subfamily of NF-κB proteins, including RelA, RelB, and c-Rel, have a transactivation domain in their C-termini. In contrast, the NF-κB1 and NF-κB2 proteins are synthesized as large precursors, p105, and p100, which undergo processing to generate the mature NF-κB subunits, p50 and p52, respectively. The processing of p105 and p100 is mediated by the ubiquitin/proteasome pathway and involves selective degradation of their C-terminal region containing ankyrin repeats. Whereas the generation of p52 from p100 is a tightly regulated process, p50 is produced from constitutive processing of p105. The p50 and p52 proteins have no intrinsic ability to activate transcription and thus have been proposed to act as transcriptional repressors when binding κB elements as homodimers. Indeed, this confounds the interpretation of p105-knockout studies, where the genetic manipulation is removing an IκB (full-length p105) and a likely repressor (p50 homodimers) in addition to a transcriptional activator (the RelA-p50 heterodimer).

NF-κB is important in regulating cellular responses because it belongs to the category of "rapid-acting" primary transcription factors, i.e., transcription factors that are present in cells in an inactive state and do not require new protein synthesis in order to become activated. This allows NF-κB to be a fast responder to harmful cellular stimuli. Known inducers of NF-κB activity are highly variable and include reactive oxygen species (ROS), tumor necrosis factor alpha (TNFα), interleukin 1-beta (IL-1p), bacterial lipopolysaccharides (LPS), isoproterenol, cocaine, and ionizing radiation. Many bacterial products and stimulation of a wide variety of cell-surface receptors lead to NF-κB activation and fairly rapid changes in gene expression. The identification of Toll-like receptors (TLRs) as specific pattern recognition molecules and the finding that stimulation of TLRs leads to activation of NF-κB improved our understanding of how different pathogens activate NF-κB. For example, studies have identified TLR4 as the receptor for the LPS component of Gram-negative bacteria. TLRs are key regulators of both innate and adaptive immune responses.

In unstimulated cells, the NF-κB dimers are sequestered in the cytoplasm by a family of inhibitors, called IκBs (Inhibitor of KB), which are proteins that contain multiple copies of a sequence called ankyrin repeats. By virtue of their ankyrin repeat domains, the IκB proteins mask the nuclear localization signals (NLS) of NF-κB proteins and keep them sequestered in an inactive state in the cytoplasm. IκBs are a family of related proteins that have an N-terminal regulatory domain, followed by six or more ankyrin repeats and a PEST domain near their C terminus. Although the IκB family consists of IκBα, IκBβ, IκBε, and Bcl-3, the best-studied and major IκB protein is IκBα. Due to the presence of ankyrin repeats in their C-terminal halves, p105 and p100 also function as IκB proteins. The c-terminal half of p100, that is often referred to as IκBδ, also functions as an inhibitor. IκBδ degradation in response to developmental stimuli, such as those transduced through LTβR, potentiate NF-κB dimer activation in a NIK dependent non-canonical pathway.

Activation of the NF-κB is initiated by the signal-induced degradation of IκB proteins. This occurs primarily via activation of a kinase called "IKK" or IκB kinase. Therefore, the term "IKK/NF-κB activation" as used in the present patent application refers to the activation of NF-κB through activation of IKK.

IKK is composed of a heterodimer of the catalytic IKKα and IKK subunits and a "master" regulatory protein termed NEMO (NF-κB essential modulator) or IKKγ. When activated by signals, the IκB kinase phosphorylates two serine residues located in an IκB regulatory domain. Upon phosphorylation of these serines (e.g., serines 32 and 36 in human IκBα), the IκB inhibitor molecules are modified by a process called ubiquitination leading to degradation by the proteasome. With the degradation of IκB, the NF-κB complex is then freed to enter the nucleus where it can 'turn on' the expression of specific genes that have DNA-binding sites for NF-κB nearby. The activation of these genes by NF-κB then leads to the given physiological response, for example, an inflammatory or immune response, a cell survival response, or cellular proliferation. NF-κB turns on expression of its own repressor, IκBα. The newly synthesized IκBα then re-inhibits NF-κB and, thus, forms an auto feedback loop, which results in oscillation, dampening and downregulation of NF-κB activity levels.

According to the present invention, genotoxic stress-induced IKK/NF-κB activation relates to the signaling pathway that is induced through the occurrence of genotoxic stress, which leads to the activation of IKK and consequently to the activation of NF-κB. Genotoxic stress triggers two corresponding signaling axes to activate the IκB kinase (IKK) complex analogously to the canonical NF-κB signaling cascades. The first axis is initiated by the DNA strand break sensor poly(ADP-ribose)-polymerase-1 (PARP-1), which sets up a transient nucleoplasmic complex and triggers PIASy mediated SUMOylation and ataxia telangiectasia mutated (ATM) mediated phosphorylation of nuclear IKKγ. Modified IKKγ shuttles back into the cytoplasm and assembles into newly formed IKK complexes. At the same ATM translocates into the cytoplasm, binds to TRAF6 and triggers its K63-linked polyubiquitination. Activated TRAF6 recruits cIAP1 and TAB2-TAK1, resulting in TAK1 activation and IKK phosphorylation. However, final activation of the IKK complex requires cIAP1-dependent IKKγ mono-ubiquitination of IKKγ at lysine 285, which is dependent on the formation of the nuclear PARP1 signalosome and the activation of the cytosolic signaling axis by the ATM-dependent activation of TRAF6.

Diseases associated with genotoxic stress-induced IKK/NF-κB activation comprise, without limitation, cancer, either during development of the disease, in the established disease or as a consequence of chemotherapy or radiation therapy of the disease, particularly colon cancer, gastric cancer, breast cancer, melanoma, myelodysplastic syndrome, acute myeloid leukemia (AML), tumors with increased PARP-1 expression, including Ewing's sarcoma, malignant lymphomas, the early stage of colorectal carcinogenesis, hepatocellular carcinoma, nonatypical and atypical endometrial hyperplasia, breast, uterine, lung, and ovarian cancers. Non-cancer diseases and conditions associated with genotoxic stress-induced IKK/NF-κB activation comprise, without limitation, diabetes type 1, diabetes type 2, stroke, subarachnoid hemorrhage (SAH), reperfusion damage, in particular of the kidney and heart, atherosclerosis, progeriod syndrome and aging.

A person skilled in the art can identify a subject suffering from cancer exhibiting genotoxic stress-induced IKK/NF-κB activation by employing standard means of analysis. There are multiple assays to identify genotoxic stress-induced NF-κB activation in tumor samples from cancer patient in order to identify subjects of the present invention intended for treatment, some of which are indicated below. The following methods represent examples and are not be understood as an exhaustive list of assays for identifying subjects suffering from cancer exhibiting genotoxic stress-induced IKK/NF-κB activation:

The following five protein-modifications indicate that IKK/NF-κB activation was induced by genotoxic stress, such as DNA double-strand breaks (DSBs), which can be generated for example by chemotherapeutical drugs or irradiation: Phospho-Ser 139 γH2A.X, Phospho-Ser 1981-ATM, Phospho-Ser 85 IKKγ, Mono-ubiquitination at Lys 285 of IKKγ and Phospho-Ser536-RelA (references for the modifications are found in Hinz et al., (2009) Mol Cell). The indicated protein modifications represent an exemplary, non-exhaustive and non-limiting list. These modifications can be assayed by established methods using commercially available antibodies, e.g. using Western blot analyses or other antibody-based techniques. Further methods to detect these modifications are mass-spectrometry techniques.

1.) Phosoho-Ser 139 vH2A.X:
Phosphorylation of H2A.X at residue Ser-139 by the PI3K-like kinases ATM, ATR and DNA-PK, is an early readout for the cellular response to the generation of DSBs by chemotherapeutical drugs or irradiation.

2.) Phosoho-Ser 1981-ATM:
This modification indicates activation of ATM by DSBs generated by chemotherapeutical drugs or irradiation.

3.) Phosoho-Ser 85 IKKv:
To the current knowledge, this modification is only detected in cells with DSBs and the presence of DSB-activated ATM. It promotes NF-κB activation by DSBs.

4.) Mono-ubiquitination at Lys 285 of IKKv:
The ubiquitination at this residues is higher in genotoxic stress (i.e. DSB)-induced NF-κB compared to cytokine-induced NF-κB.

5.) Phosoho-Ser536-RelA:
This modification indicates NF-κB activation through diverse activating pathways, not limited to the genotoxic stress-induced pathway.

Patients that are suitable for the application of the compounds of the present invention and its use as a medicament and/or subject suffering from cancer exhibiting genotoxic stress-induced IKK/NF-κB activation comprise subjects suffering from any cancer type which is being or has been treated with DNA-damage-inducing chemotherapy or irradiation.

The use of the compounds of the invention can in some embodiments be employed primarily as "add-on" drugs in genotoxic therapies (chemotherapies, irradiation) to enhance cancer/tumor cell killing by suppression of NF-κB-dependent protection against apoptosis. Thus, there would be a large spectrum of malignancies where treatment success may be improved.

It is anticipated that the PARP1-PIASy-ATM-IKKγ complex and ATM-TRAF6 axis will be activated by chemotherapy and/or irradiation in a number of different cancer types. The assays described above may be used to affirm activation of the genotoxic stress induced NF-κB pathway by the respective standard chemotherapy or irradiation protocol in a given disease. The assays can also be used for therapy resistant cancers to decide to apply compounds of the present invention. The assays can also be applied prior to any treatment with cancers expected to have high level unrepaired DNA damage (e.g. when mutations in DNA repair genes have been documented).

In a preferred embodiment the present invention relates to cancer as a disease to be treated. Cancer according to the present invention refers to all types of cancer or neoplasm or malignant tumors found in mammals, including leukemias, lymphomas, sarcomas, melanomas and carcinomas. Examples of cancers are cancer of the breast, pancreas, colon, lung, non-small cell lung, ovary, and prostate.

In the context of the present invention, leukemias include, but are not limited to acute non-lymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

According to the present invention, lymphomas include Hodgkin and non-Hodgkin lymphoma (B-cell and T-cell lymphoma) including, but not limited to Diffuse large B-cell lymphoma (DLBCL), primary mediastinal B-cell lymphoma, Follicular lymphoma, Chronic lymphocytic leukemia, small lymphocytic lymphoma, Mantle cell lymphoma, Marginal zone B-cell lymphomas, Extranodal marginal zone B-cell lymphomas, also known as mucosa-associated lymphoid tissue (MALT) lymphomas, Nodal marginal zone B-cell lymphoma and Splenic marginal zone B-cell lymphoma, Burkitt lymphoma, Lymphoplasmacytic lymphoma (Waldenstrom macroglobulinemia), Hairy cell leukemia Primary central nervous system (CNS) lymphoma, Precursor T-lymphoblastic lymphoma/leukemia, Peripheral T-cell lymphomas, Cutaneous T-cell lymphomas (mycosis fungoides, Sezary syndrome, and others), Adult T-cell leukemia/lymphoma including the smoldering, the chronic, the acute and the lymphoma subtype, Angioimmunoblastic T-cell lymphoma, Extranodal natural killer/T-cell lymphoma, nasal type, Enteropathy-associated intestinal T-cell lymphoma (EATL), Anaplastic large cell lymphoma (ALCL), and unspecified Peripheral T-cell lymphoma.

Sarcomas as defined in the context of the present invention include, but are not limited to a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Melanomas according to the present invention include, but are not limited to include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

Carcinomas as defined by the present invention include, but are not limited to acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma exulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers according to the present invention include, but are not limited to multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, esophageal cancer, genitourinary tract cancer, malignant hypercalcemia, cervical cancer, endometrial cancer, adrenal cortical cancer, and prostate cancer.

In the context of the present invention, the term "DNA damage" refers to alteration in the chemical structure of DNA, such as a break in a strand of DNA, a base missing from the backbone of DNA, or a chemically changed base. Damage to DNA that occurs naturally can result from metabolic or hydrolytic processes. Metabolism releases compounds that damage DNA including reactive oxygen species, reactive nitrogen species, reactive carbonyl species, lipid peroxidation products and alkylating agents, among others, while hydrolysis cleaves chemical bonds in DNA. While most DNA damages can undergo DNA repair, such repair is not 100% efficient. Un-repaired DNA damages accumulate in non-replicating cells, such as cells in the brains or muscles of adult mammals and can cause aging. In replicating cells, such as cells lining the colon, errors occur upon replication of past damages in the template strand of DNA or during repair of DNA damages. These errors can give rise to mutations or epigenetic alterations. Both of these types of alteration can be replicated and passed on to subsequent cell generations. These alterations can change gene function or regulation of gene expression and possibly contribute to progression to cancer. Failure to repair DNA lesions may result in blockages of transcription and replication, mutagenesis, and/or cellular cytotoxicity. In humans, DNA damage has been shown to be involved in a variety of genetically inherited disorders, in aging, and in carcinogenesis.

All eukaryotic cells have evolved a multifaceted response to counteract the potentially deleterious effects of DNA damage. Upon sensing DNA damage or stalls in replication, cell cycle checkpoints are activated to arrest cell cycle progression to allow time for repair before the damage is passed on to daughter cells. In addition to checkpoint activation, the DNA damage response leads to induction of transcriptional programs, enhancement of DNA repair pathways, and when the level of damage is severe, to initiation of apoptosis. All of these processes are carefully coordinated so that the genetic material is faithfully maintained, duplicated, and segregated within the cell.

The term "DNA repair" refers to a number of cellular processes or pathways to restore lost information after DNA damage, when used in the context of the present invention. These processes and pathways comprise, without limitation, cell cycle check points such as the G1 checkpoint, S-phase checkpoint, G2-M checkpoint, and DNA repair pathways such as direct reversal, base excision repair, nucleotide excision repair, DNA mismatch repair and double strand break repair. The rate of DNA repair is dependent on many factors, including the cell type, the age of the cell, and the extracellular environment.

A cell that has accumulated a large amount of DNA damage, or one that no longer effectively repairs damage incurred to its DNA, can undergo different cellular processes including an irreversible state of dormancy, known as senescence, apoptosis, which is a programmed cell death program, other cell death programs, such as necrosis, non-apoptotic programmed cell-death or necroptosis, unregulated cell division, which can lead to the formation of a tumor that is cancerous.

In the sense of the present invention, the term "DNA repair gene" refers to all genes, which are involved in the control or modulation of DNA repair mechanisms and pathways. These include, without limitation, for base excision repair (BER), UNG, SMUG1, MBD4, TDG, OGG1, MUTYH (MYH), NTHL1 (NTH1), MPG, NEIL1, NEIL2, NEIL3, APEX1 (APE1), APEX2, LIG3, XRCC1, PNKP, APLF (C2ORF13); for Poly(ADP-ribose) polymerase (PARP) enzymes that bind to DNA PARP1 (ADPRT), PARP2 (ADPRTL2), PARP3 (ADPRTL3); for direct reversal of damage MGMT, ALKBH2 (ABH2), ALKBH3 (DEPC1); for repair of DNA-topoisomerase crosslinks TDP1, TDP2 (TTRAP); for mismatch excision repair (MMR) MSH2, MSH3, MSH6, MLH1, PMS2, MSH4, MSH5, MLH3, PMS1, PMS2L3; for nucleotide excision repair (NER) XPC, RAD23B, CETN2, RAD23A, XPA, DDB1, DDB2 (XPE), RPA1, RPA2, RPA3, TFIIH, ERCC3 (XPB), ERCC2 (XPD), GTF2H1, GTF2H2, GTF2H3, GTF2H4, GTF2H5 (TTDA), CDK7, CCNH, MNAT1, ERCC5 (XPG), ERCC1, ERCC4 (XPF), LIG1; NER-related ERCC8 (CSA), ERCC6 (CSB), UVSSA (KIAA1530), XAB2 (HCNP), MMS19; for homologous recombination RAD51, RAD51B, RAD51D, DMC1, XRCC2, XRCC3, RAD52, RAD54L, RAD54B, BRCA1, SHFM1 (DSS1), RAD50, MRE11A, NBN (NBS1), RBBP8 (CtIP), MUS81, EME1 (MMS4L), EME2, GIYD1 (SLXIA), GIYD2 (SLXIB), GEN1; for fanconi anemia FANCA, FANCB, FANCC, BRCA2 (FANCD1), FANCD2, FANCE, FANCF, FANCG (XRCC9), FANCI (KIAA1794), BRIP1 (FANCJ), FANCL, FANCM, PALB2 (FANCN), RAD51C (FANCO), BTBD12 (SLX4) (FANCP), FAAP20 (C1orf86), FAAP24 (C19orf40); for non-homologous end-joining XRCC6 (Ku70), XRCC5 (Ku80), PRKDC, LIG4, XRCC4, DCL-REIC (Artemis), NHEJ1 (XLF, Cernunnos); for modulation of nucleotide pools NUDT1 (MTH1), DUT, RRM2B (p53R2); for DNA polymerases (catalytic subunits) POLB, POLG, POLD1, POLE, PCNA, REV3L (POLZ), MAD2L2 (REV7), REV1L (REV1), POLH, POLI (RAD30B), POLQ, POLK (DINB1), POLL, POLM, POLN (POL4P); for editing and processing nucleases FEN1 (DNase IV), FAN1 (MTMR15), TREX1 (DNase III), TREX2, EXO1 (HEX1), APTX (aprataxin), SPO11, ENDOV; for Ubiquitination and modification UBE2A (RAD6A), UBE2B (RAD6B), RAD18, SHPRH, HLTF (SMARCA3), RNF168, SPRTN (c1orf124), RNF8, RNF4, UBE2V2 (MMS2), UBE2N (UBC13); for Chromatin Structure and Modification H2AFX (H2AX), CHAF1A (CAF1), SETMAR (METNASE); for genes defective in diseases associated with sensitivity to DNA damaging agents BLM, WRN, RECQL4, ATM, TTDN1 (C7orf11); for other identified genes with known or suspected DNA repair function DCLREIA (SNM1), DCLREI B (SNM1B), RPA4, PRPF19 (PSO4), RECQL (RECQ1), RECQL5, HELQ (HEL308), RDM1 (RAD52B), OBFC2B (SSB1); other conserved DNA damage response genes ATR, ATRIP, MDC1, RAD1, RAD9A, HUS1, RAD17 (RAD24), CHEK1, CHEK2, TP53, TP53BP1 (53BP1), RIF1, TOPBP1, CLK2, PER1.

In one embodiment of the present invention the compound is more effective in inhibiting NF-κB-signaling induced by preferably genotoxic stress compared to inhibiting NF-κB-signaling induced by TNF-alpha (TNFα) and/or IL-1β.

According to the present invention, TNFα or tumor necrosis factor alpha is a cell signaling protein (cytokine) involved in systemic inflammation and is one of the cytokines that make up the acute phase reaction. TNFα regulates immune cells, is able to induce fever, apoptotic cell death, cachexia, inflammation and to inhibit tumorigenesis and viral replication and respond to sepsis via IL1 & IL6 producing cells. Dysregulation of TNFα production has been implicated in a variety of human diseases including Alzheimer's disease, cancer, major depression, Psoriasis and inflammatory bowel disease (IBD). TNFα can bind two receptors, TNFR1 (TNF receptor type 1; CD120a; p55/60) and TNFR2 (TNF receptor type 2; CD120b; p75/80). TNFR signaling induces activation of several intracellular signaling pathways, including activation of NF-κB.

In the sense of the present invention, IL-1β is also known as "leukocytic pyrogen", "leukocytic endogenous mediator", "mononuclear cell factor", "lymphocyte activating factor" among other names and is a cytokine protein that in humans is encoded by the MB gene. IL-1β is a member of the interleukin 1 family of cytokines. This cytokine is produced by activated macrophages as a proprotein, which is proteolytically processed to its active form by caspase 1 (CASP1/ICE). This cytokine is an important mediator of the inflammatory response, and is involved in a variety of cellular activities, including cell proliferation, differentiation, and apoptosis.

In the context of the present invention, the term "NF-κB signaling induced by TNFα and/or IL-1β" refers to the activation of the classical or canonical NF-κB signaling pathway, which gets activated upon stimulation with TNFα and/or IL-1β. In the canonical signaling pathway, NF-κB/Rel proteins are bound and inhibited by IκB proteins. Proinflammatory cytokines such as TNFα and IL-1β, LPS, growth factors, and antigen receptors induce signaling cascades that lead to IKK complex activation (IKKβ, IKKα, and NEMO), which phosphorylates IκB proteins. Phosphorylation of IκB leads to its ubiquitination and proteasomal degradation, freeing NF-κB/Rel complexes. Active NF-κB/Rel complexes are further activated by post-translational modifications (phosphorylation, acetylation, glycosylation, ubiquitination) and translocate to the nucleus where, either alone or in combination with other transcription factors including AP-1, Ets, and Stat, they induce target gene expression.

The present invention can also relate to the treatment of a disease, which is associated with genomic instability due to defective DNA-repair mechanisms.

The term "genomic instability", as used in the context of the present invention, refers to a high frequency of mutations within the genome of a cellular lineage. Such mutations can include changes in nucleic acid sequences, chromosomal rearrangements or aneuploidy. Genome instability does occur in bacteria. In multicellular organisms genome instability is central to carcinogenesis and occurs in many types of cancer. The skilled person can easily identify cancers that are associated with genomic instability by routine testing. Other diseases than cancer associated with genomic instability comprise neuronal diseases, including neurodegenerative diseases such as amyotrophic lateral sclerosis and the neuromuscular disease myotonic dystrophy.

Many neuronal and neurodegenerative disorders are associated with genomic instability due to inherited or acquired defects in of the DNA repair pathways or excessive genotoxic oxidative stress. This has been established for a number of such disease, including xeroderma pigmentosum, Cockayne's syndrome, trichothiodystrophy, Down's syndrome, triple-A syndrome, spinocerebellar ataxia with axonal neuropathy-1, Huntington's disease, Alzheimer's disease, Parkinson's disease, Down's syndrome and amyotrophic lateral sclerosis, Huntington's disease, various spinocerebellar ataxias, Friedreich's ataxia, myotonic dystrophy types 1 and 2, ataxia-telangiectasia, ataxia-telangiectasia-like disorder, Nijmegen breakage syndrome and Alzheimer's disease. Xeroderma pigmentosum, Cockayne's syndrome, trichothiodystrophy, Down's syndrome, and triple-A syndrome have a defect in the DNA nucleotide excision repair pathway, spinocerebellar ataxia with axonal neuropathy-1, Huntington's disease, Alzheimer's disease, Parkinson's disease, Down's syndrome and amyotrophic lateral sclerosis result or are associated with increased oxidative stress and the inability of the base excision repair pathway to handle the damage to DNA that this causes, Huntington's disease, various spinocerebellar ataxias, Friedreich's ataxia and myotonic dystrophy types 1 and 2 often have an unusual expansion of repeat sequences in DNA, likely attributable to genome instability, and ataxia-telangiectasia, ataxia-telangiectasia-like disorder, Nijmegen breakage syndrome and Alzheimer's disease are defective in genes involved in repairing DNA double-strand breaks.

In cancer, genome instability can occur prior to or as a consequence of transformation. Genome instability can refer to, without limitation, the accumulation of extra copies of DNA or chromosomes, chromosomal translocations, chromosomal inversions, chromosome deletions, single-strand breaks in DNA, double-strand breaks in DNA, the intercalation of foreign substances into the DNA double helix, or any abnormal changes in DNA tertiary structure that can cause either the loss of DNA, or the misexpression of genes. The unpredictable nature of these events is also a main contributor to the heterogeneity observed among tumour cells.

Further diseases associated with genomic instability include progeroid syndrome diseases (PS) and associated potentially NF-κB-dependent pathologies, including tumors. Examples of PS include Werner syndrome (WS), Bloom syndrome (BS), Rothmund-Thomson syndrome (RTS), Cockayne syndrome (CS), xeroderma pigmentosum (XP), trichothiodystrophy (TTD), combined xeroderma pigmentosum-Cockayne syndrome (XP-CS), restrictive dermopathy (RD), and Hutchinson-Gilford progeria syndrome (HGPS).

In the context of the present invention, the term "defective" refers to that something, for example a cellular system such as the DNA repair system or the DNA damage response system, which has a problem or fault that prevents it from working correctly.

In the context of the present invention the term "alteration" refers to any kind of change, modification or adjustment that is made so that the original state of something is changed or altered, when used in the context of the present invention. Genetic alterations therefore refer to changes that are occurring on genetic material, including changes that occur with respect to the nucleotide sequence of a nucleic acid molecule. Epigenetic alterations refer to changes of the epigenetic state of a nucleic acid molecule, for example a DNA molecule, which do not change the nucleotide sequence of the molecule. Epigenetic modifications can occur on the nucleic acid or on the chromatin, which includes histones and histone modifications. Epigenetic modifications or alterations include, without limitation, acetylation, methylation, ubiquitination, phosphorylation, sumoylation, ribosylation and citrullination.

The term "resistance" in the sense of the present invention refers to the reduction in effectiveness of a drug such as an antimicrobial, anthelmintic or an antineoplastic in treating a disease or condition. The term is used in the context of, for example, pathogens or cancer cells, which have "acquired" resistance to a drug or to another treatment or mechanism that is directed against the pathogen or the cancer cell. Antimicrobial resistance and antineoplastic resistance challenge when an organism or cancer cell is resistant to more than one drug, it is said to be multidrug-resistant.

According to the present invention, cancer therapeutic resistance refers to the development of resistance to treatments such as chemotherapy, radiotherapy, irradiation therapy, cell therapy and targeted therapies by cancer cells through different mechanisms. These mechanisms include specific genetic and epigenetic changes in the cancer cell and/or the microenvironment in which the cancer cell resides. Also, activation of different signaling pathways, including the NF-κB pathway, can contribute to the development of cancer therapeutic resistance. The term "NF-κB-mediated resistance to apoptosis" refers to cellular mechanisms, by which the genotoxic stress-activated NF-κB pathway inhibits the induction of apoptosis, when used in the context of the present invention. NF-κB activation in response to DNA damaging cancer therapy is a principal mechanism of inducible tumour cell resistance.

Cancers that are associated with NF-κB-mediated resistance to therapy-induced tumor cell apoptosis in the sense of the present invention include, but are not limited to BRCA1 or BRCA2 mutant ovarial carcinoma, breast carcinoma, cervical carcinoma, gastric carcinoma, pancreatic carcinoma or prostate carcinoma.

The compound according to the present invention as described herein may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly-subcutaneously, subconjunctival, intravesicularly, mucosally, intrapericardially, intraumbilically, intraocularly, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

In the context of the present invention, the term "cancer therapy" refers to any kind of treatment of cancer, including, without limitation, surgery, chemotherapy, radiotherapy, irradiation therapy, hormonal therapy, targeted therapy, cellular therapy, cancer immunotherapy, monoclonal antibody therapy.

Administration of the compound can be individual as mono-therapy or in combination with one or more other cancer therapies. In the context of the present invention the term "in combination" indicates that an individual that receives the compound according to the present invention also receives other cancer therapies, which does not necessarily happen simultaneously, combined in a single pharmacological composition or via the same route of administration. "In combination" therefore refers the treatment of an individual suffering from cancer with more than one cancer therapy. Combined administration encompasses simultaneous treatment, co-treatment or joint treatment, whereby treatment may occur within minutes of each other, in the same hour, on the same day, in the same week or in the same month as one another.

DNA damage-inducing cancer therapies in the sense of the present invention include, but are not limited to irradiation therapy and chemotherapy and work by overwhelming the capacity of the cell to repair DNA damage, resulting in cell death.

In this context, chemotherapy refers to a category of cancer treatment that uses one or more anticancer drugs (chemotherapeutic agents) as part of a standardized chemotherapy regimen. Chemotherapy may be given with a curative intent (which almost always involves combinations of drugs), or it may aim to prolong life or to reduce symptoms (palliative chemotherapy). Chemotherapy is one of the major categories of medical oncology (the medical discipline specifically devoted to pharmacotherapy for cancer). Chemotherapeutic agents are used to treat cancer and are administered in regimens of one or more cycles, combining two or more agents over a period of days to weeks. Such agents are toxic to cells with high proliferative rates—e.g., to the cancer itself, but also to the GI tract (causing nausea and vomiting), bone marrow (causing various cytopenias) and hair (resulting in baldness).

Chemotherapeutic agents comprise, without limitation, Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine.

Irradiation or radiation therapy or radiotherapy in the context of the present invention relates to a therapeutic approach using ionizing or ultraviolet-visible (UV/Vis) radiation, generally as part of cancer treatment to control or kill malignant cells such as cancer cells or tumor cells. Radiation therapy may be curative in a number of types of cancer, if they are localized to one area of the body. It may also be used as part of adjuvant therapy, to prevent tumor recurrence after surgery to remove a primary malignant tumor (for example, early stages of breast cancer). Radiation therapy is synergistic with chemotherapy, and can been used before, during, and after chemotherapy in susceptible cancers. Radiation therapy is commonly applied to the cancerous tumor because of its ability to control cell growth. Ionizing radiation works by damaging the DNA of cancerous tissue leading to cellular death. Radiation therapy can be used systemically or locally.

Radiation therapy works by damaging the DNA of cancerous cells. This DNA damage is caused by one of two types of energy, photon or charged particle. This damage is either direct or indirect ionization of the atoms which make up the DNA chain. Indirect ionization happens as a result of the ionization of water, leading to the formation of free radicals, including hydroxyl radicals, which then damage the DNA. In photon therapy, most of the radiation effect is mediated through free radicals. Cells have mechanisms for repairing single-strand DNA damage and double-stranded DNA damage. However, double-stranded DNA breaks are much more difficult to repair, and can lead to dramatic chromosomal abnormalities and genetic deletions. Targeting double-stranded breaks increases the probability that cells will undergo cell death.

The amount of radiation used in photon radiation therapy is measured in gray (Gy), and varies depending on the type and stage of cancer being treated. For curative cases, the typical dose for a solid epithelial tumor ranges from 60 to 80 Gy, while lymphomas are treated with 20 to 40 Gy. Preventive (adjuvant) doses are typically around 45-60 Gy in 1.8-2 Gy fractions (for breast, head, and neck cancers.)

Different types of radiation therapy are known such as external beam radiation therapy, including conventional external beam radiation therapy, stereotactic radiation (radiosurgery), virtual simulation, 3-dimensional conformal radiation therapy, and intensity-modulated radiation therapy, intensity-modulated radiation therapy (IMRT), volumetric modulated arc therapy (VMAT), Particle therapy, auger therapy, brachytherapy, intraoperative radiotherapy, radioisotope therapy and deep inspiration breath-hold.

External beam radiation therapy comprises X-ray, gamma-ray and charged particles and can be applied as a low-dose rate or high dose rate depending on the overall therapeutic approach.

In internal radiation therapy radioactive substance can be bound to one or more monoclonal antibodies. For example, radioactive iodine can be used for thyroid malignancies. Brachytherapy of High dose regime (HDR) or low dose regime (LDR) can be combined with IR in prostate cancer.

According to the present invention, DNA damage-inducing chemotherapies comprise the administration of chemotherapeutics agents including, but not limited to anthracyclines such as Daunorubicin, Doxorubicin, Epirubicin, Idarubicin, Valrubicin, Mitoxantrone; Inhibitors of topoisomerase I such as Irinotecan (CPT-11) and Topotecan; Inhibitors of topoisomerase II including Etoposide, Teniposide and Tafluposide; Platinum-based agents such as Carboplatin, Cisplatin and Oxaliplatin; and other chemotherapies such as Bleomycin.

The pharmaceutical compositions can be administered to subjects by a variety of mucosal administration modes, including by oral, rectal, intraocular, intranasal, intrapulmonary, or transdermal delivery, or by topical delivery to other surfaces. Optionally, the compositions can be administered by non-mucosal routes, including by intramuscular, intraocular, subcutaneous, intravenous, intra-arterial, intraarticular, intraperitoneal, intrathecal, intracerebroventricular, or parenteral routes.

The compositions of the disclosure can alternatively contain as pharmaceutically acceptable carrier substances that are required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

The instant disclosure also includes kits, packages and multi-container units containing the herein described pharmaceutical compositions, active ingredients, and/or means for administering the same for use in the prevention and treatment of diseases and other conditions in mammalian subjects.

FIGURES

The invention is further described by the following figures. These are not intended to limit the scope of the invention, but represent preferred embodiments of aspects of the invention provided for greater illustration of the invention described herein.

DETAILED DESCRIPTION OF THE FIGURES

Figure 1:
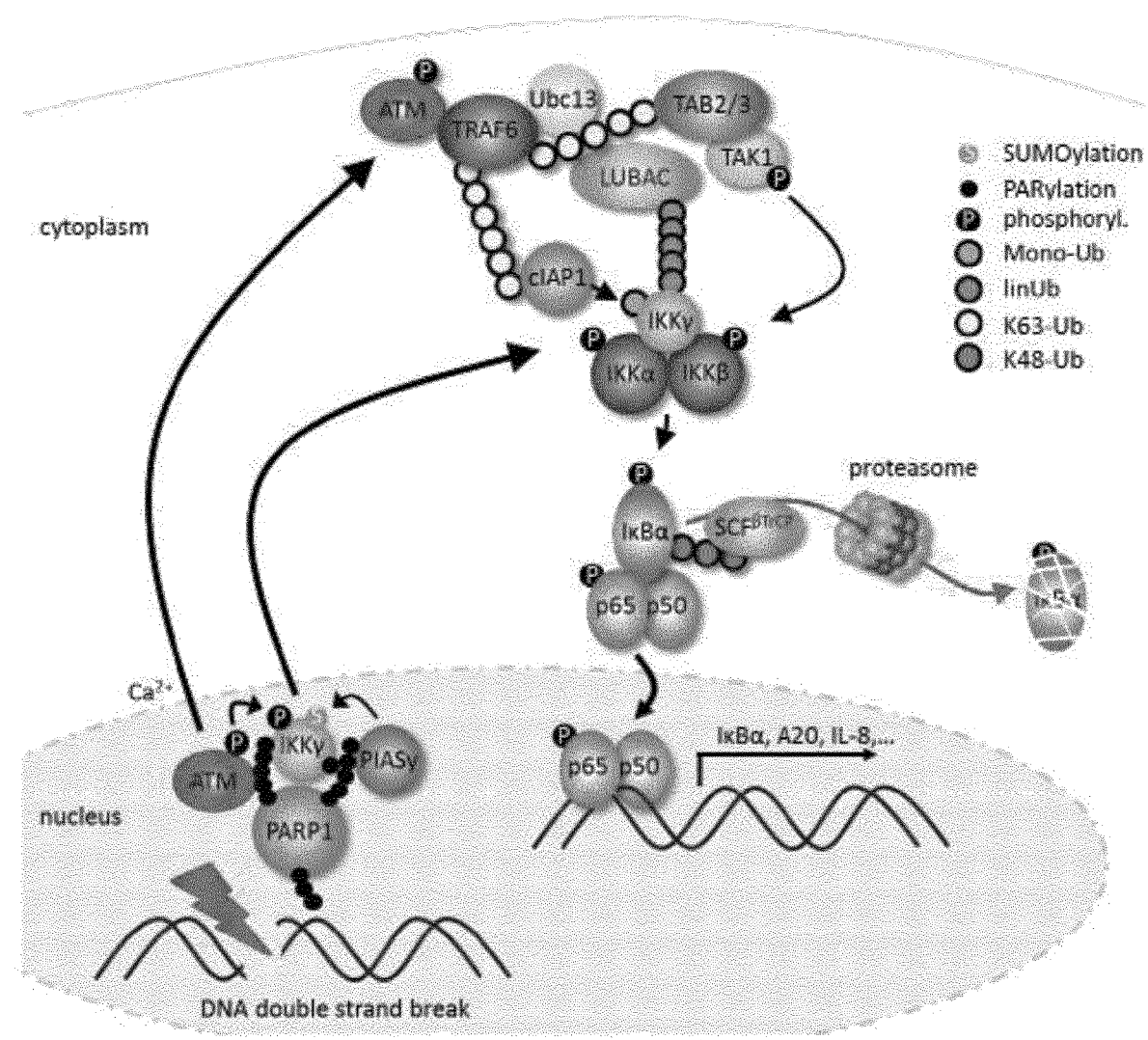
FIG. 1: Simplified model of the genotoxic stress-induced NF-κB signaling cascade.

FIG. 1: Upon DNA double strand breaks the sensor proteins ATM and PARP1 are activated. PARP1 undergoes poly(ADP)-ribose (PAR) chain auto-modification, which serve as a scaffold for the recruitment of the IKK complex subunit IKKγ, PIASy, and activated ATM. The formation of the this nuclear PARP1 signalosome leads to posttranslational modifications of IKKγ-SUMOylation by PIASy and phosphorylation by ATM. SUMOylated and phosphorylated IKKγ is transported into cytoplasm where it most likely is incorporated into IKK holocomplexes. Simultaneously, ATM is transported into cytoplasm. After binding to TRAF6 it activates its auto-polyubiquitination with Ubc13-assisted lysine 63-linked ubiquitin chains. These ubiquitin chains serve as a scaffold for the recruitment of important signaling components like TAB2-TAK1, cIAP1 and the IKK complex. Ubiquitin-mediated binding of TAK1 to the cytoplasmic signalosome leads to TAK1 auto-phosphorylation that subsequently leads to a priming IKK phosphorylation by TAK1 and an auto-phosphorylation of the IKK T-loop serines. Convergence of exported SUMOylated IKKγ and the cytoplasmic ATM-TRAF6-dependent axis is required for mono-ubiquitination of IKKγ at Lys285, which in turn is essential for full IKK activation (Hinz et al.; 2010, Stilmann et al.; 2009). As an additional step, LUBAC-dependent M1-linked ubiquitination of IKKγ was shown to be critical for the genotoxic NF-κB pathway. Activation of the IKK complex subsequently leads to the degradation of IκBα and the activation of the NF-κB heterodimer p65/p50 analogously to canonical NF-κB activation.

Figure 2:
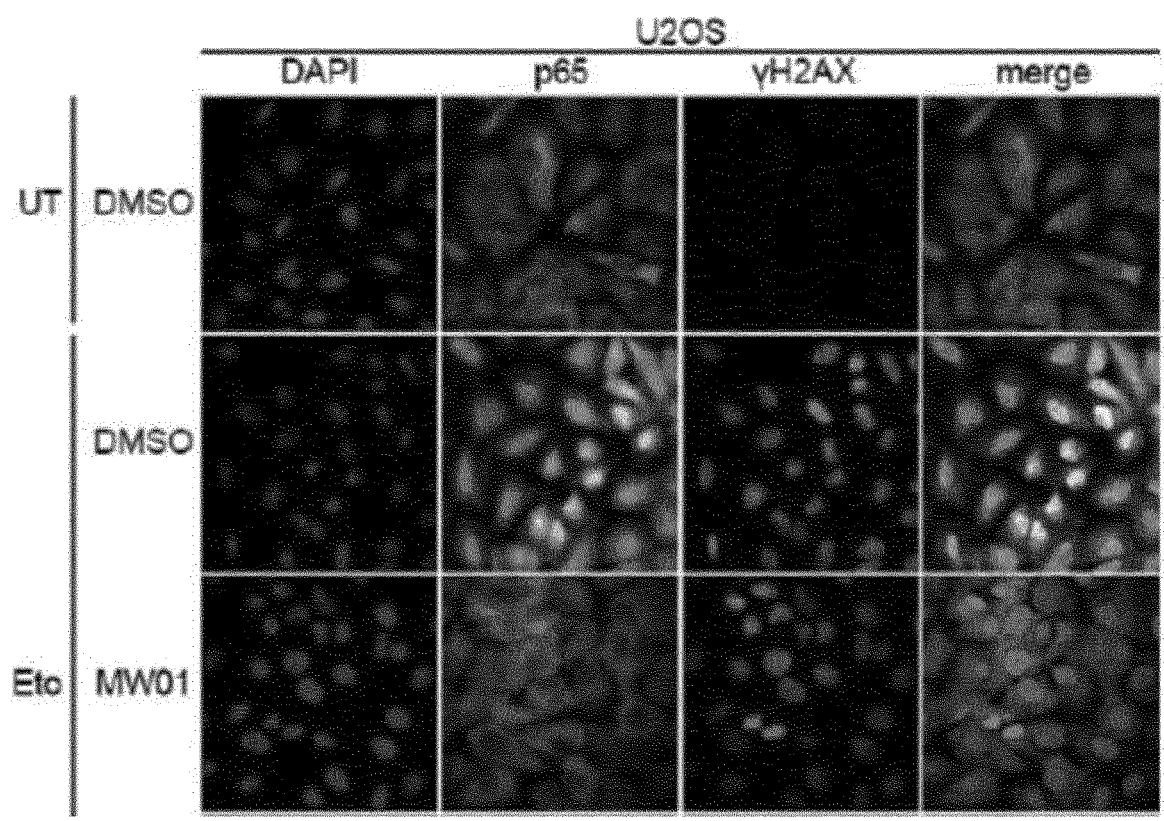
FIG. 2: MW01 is a specific inhibitor of DNA damage induced p65 nuclear translocation.

FIG. 2: U2OS cells were pre-treated and incubated with DMSO or MW01. DNA damage was induced by administration of etoposide. After 2 h cells were fixed, nuclei were stained with DAPI. p65 and phospho-H2AX, which is indicative for DNA DSB, were stained by immunofluorescence. Images were taken at a confocal Zeiss 710 LSM with a 40× oil objective.

Figure 3:
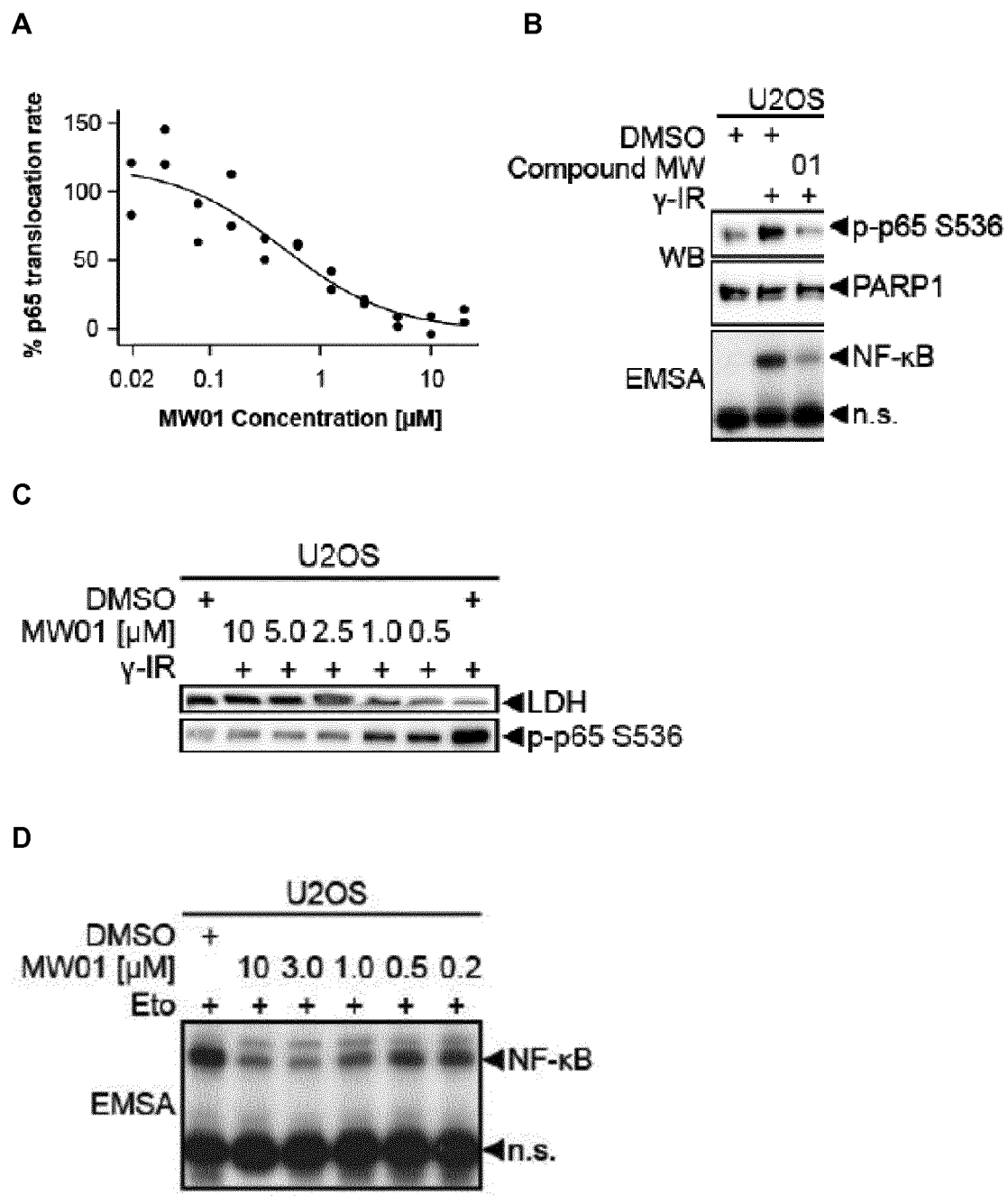
FIG. 3: Concentration dependent inhibition of DNA damage-induced NF-κB activation by MW01.

FIG. 3: (A) U2OS cells were pre-treated with increasing concentrations of MW01 in duplicates in a 384 well plate. Then, cells were treated with etoposide, fixed and subjected to IF of p65. Spatial measurement of p65 cytosolic and nuclear localisation was used for calculation of p65 translocation rates. (B) U2OS cells were pre-treated with DMSO, MW01 and irradiated with γ-IR. After 90 min cells were lysed and subjected to SDS-PAGE/WB and EMSA. (C) Cells were pre-treated with different concentrations of MW01 as indicated, treated with γ-IR (C) or etoposide (D) and subjected to WB or EMSA, respectively. LDH in (C) represents the loading control.

Figure 4:
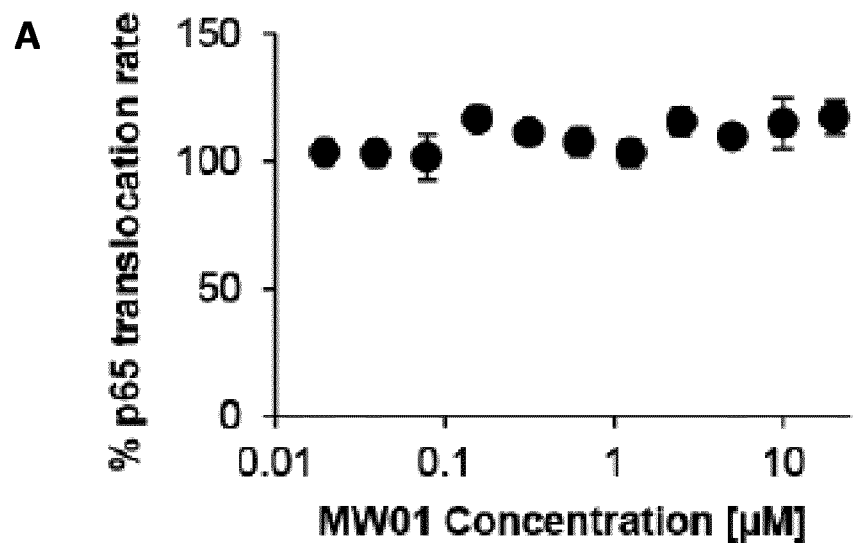
FIG. 4: MW01 does not inhibit NF-κB activation by TNFα stimulation.
Figure 4:
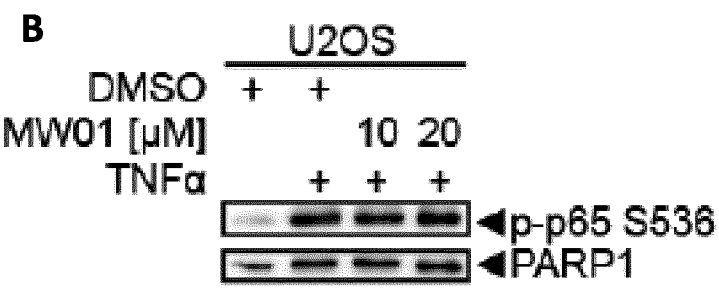
Figure 4:
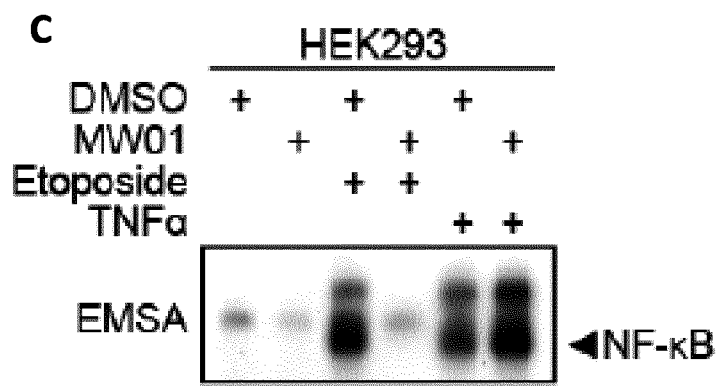

FIG. 4: (A) U2OS cells were pre-treated with increasing concentrations of MW01 in triplicates in a 384 well plate. Then, cells were treated with TNFα, fixed and subjected to IF staining of p65. Spatial measurement of p65 cytosolic and nuclear signals was used for the calculation of p65 translocation rates. (B) U2OS cells were pre-treated with MW01 at concentrations of 10 or 20 μM and stimulated with TNFα. Cell lysates were subjected to SDS-PAGE/WB. (C) HEK293 cells were pre-treated with DMSO or MW01 followed by administration of etoposide or TNFα. Cell lysates were used for EMSA.

Figure 5:
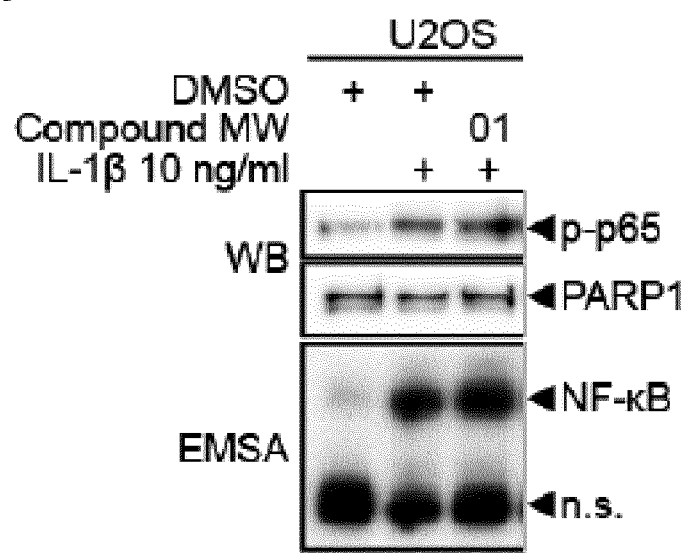
FIG. 5: MW01 does not inhibit NF-κB activation by IL-1β stimulation.
Figure 5:
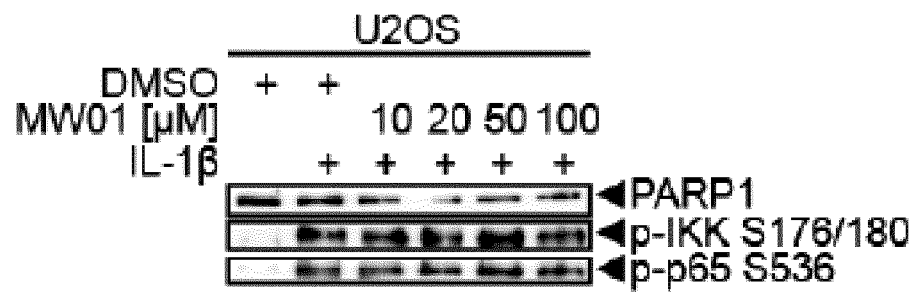

FIG. 5: (A) U2OS cell were pre-treated with MW01 followed by stimulation with IL-1p. Cell lysates were used for SDS-PAGE/WB and EMSA. (B) Cells pre-treated with increasing concentrations MW01 were stimulated with IL-1p. Cell lysates were used for SDS-PAGE/WB and stained with indicated antibodies.

Figure 6:
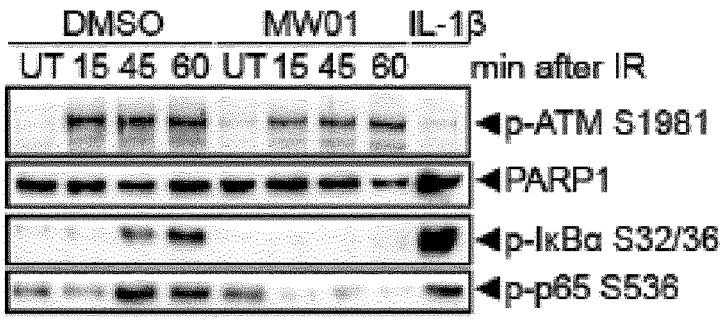
FIG. 6: Inhibition of genotoxic stress-induced NF-κB activation by MW01 takes place upstream of TAK1 activation.
Figure 6:
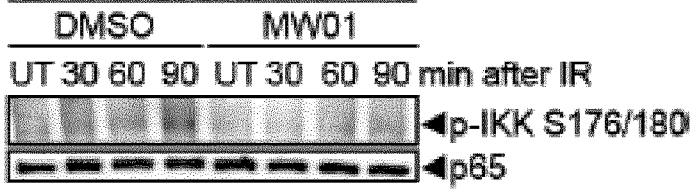
Figure 6:
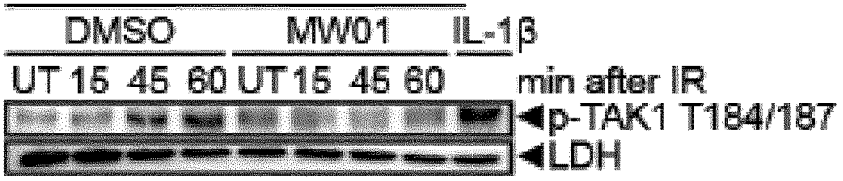
Figure 6:
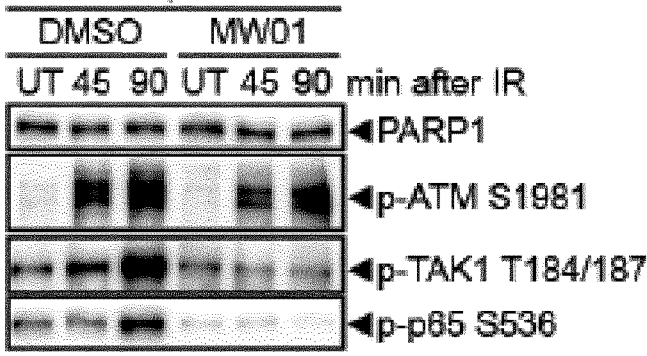

FIG. 6: (A) U2OS cells were pre-treated with DMSO or MW01 and irradiated. Stimulation of cell with IL-1β served as a positive control for IκBα and p65 phosphorylation. Cells were lysed at indicated time points and used for WB analyses. (B,C) Similar experimental setup as in (A). (D) Experiment as in (A-C), but with other time points analysed and performed with HepG2 cells. PARP1 and LDH serve as loading controls.

Figure 7:
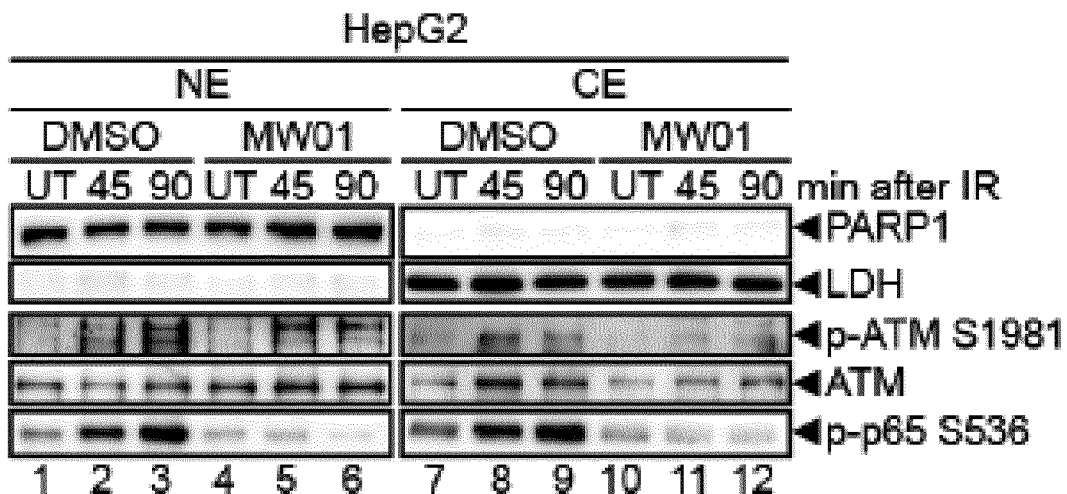
FIG. 7: MW01 inhibits genotoxic stress-induced NF-κB activation by blocking the cytoplasmic accumulation of ATM.
Figure 7:
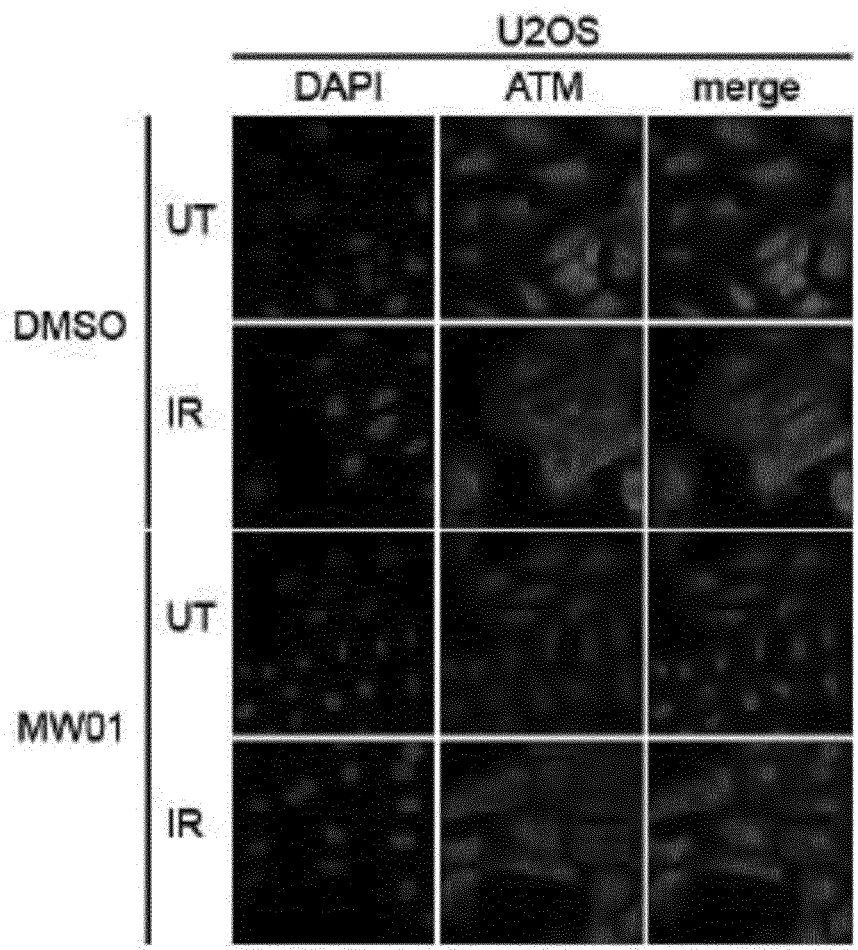

FIG. 7: Cytoplasmic accumulation of ATM. (A) Fractionation experiment with separated nuclear extracts (NE) and cytoplasmic extracts (CE). PARP1 and LDH staining served as loading and fractionation controls. Cells were pre-treated with DMSO or MW01 (5 μM) prior to irradiation and cell harvesting at indicated times. NE and CE were subjected to SDS-PAGE/WB procedure. (B) U2OS cells were seeded on cover slips 2 days before treatment. The cells were pre-treated with solvent DMSO alone or with MW01 prior to irradiation, cell fixation and subsequent immunofluorescence staining.

Figure 8:
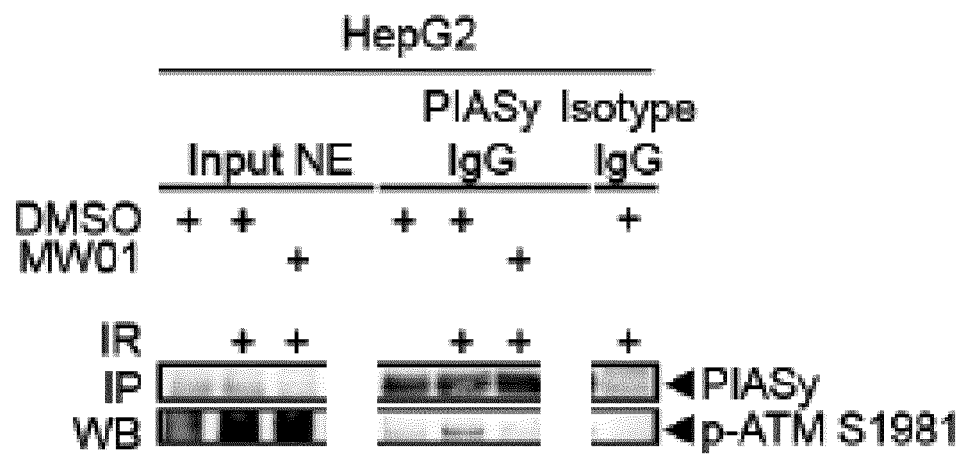
FIG. 8: MW01 inhibits the formation of the nuclear PARP1-signalosome.
Figure 8:
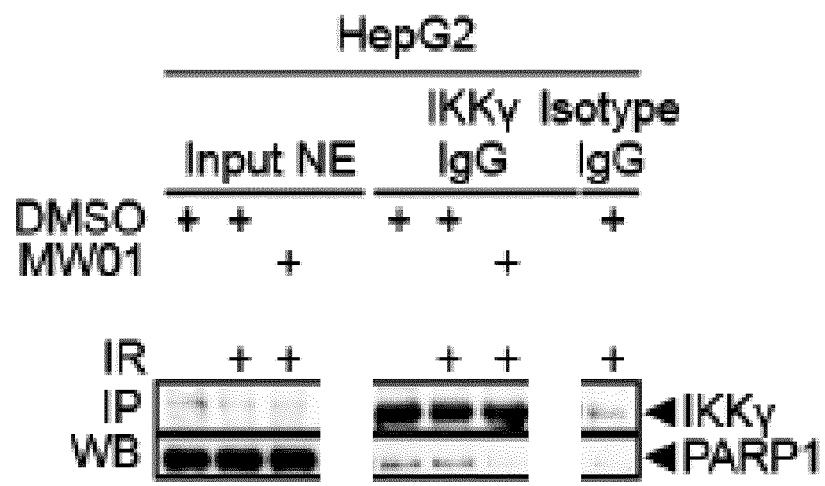
Figure 8:
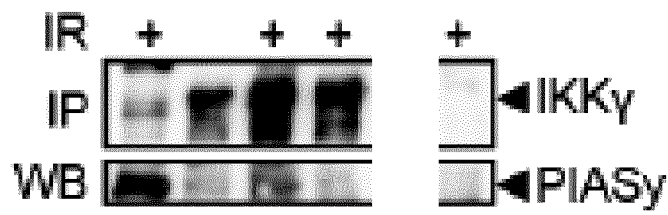
Figure 8:
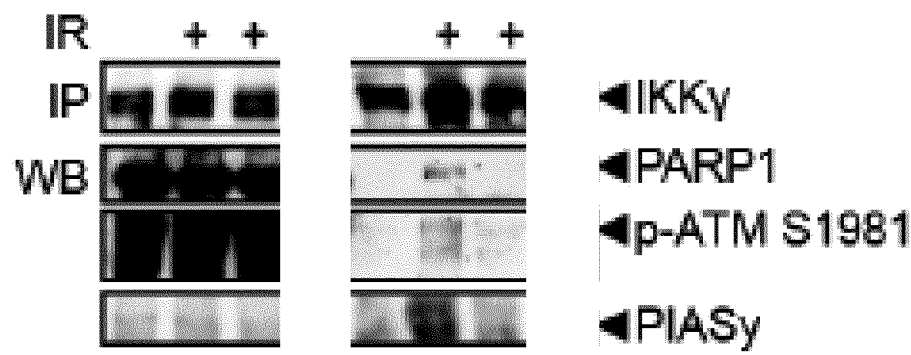

FIG. 8: (A) HepG2 cells were pre-treated with DMSO or MW01 and irradiated. Nuclear cell extracts (NE) were used for PIASy immunoprecipitation (IP). Western blot membranes were incubated with indicated antibodies. (B) Experiment as shown in (A), but with IKKγ IP. (C) Experiment as shown in (B), but done in HEK293 cells. (D) Experiment done as shown in (F), but repeated in MEF cells.

Figure 9:
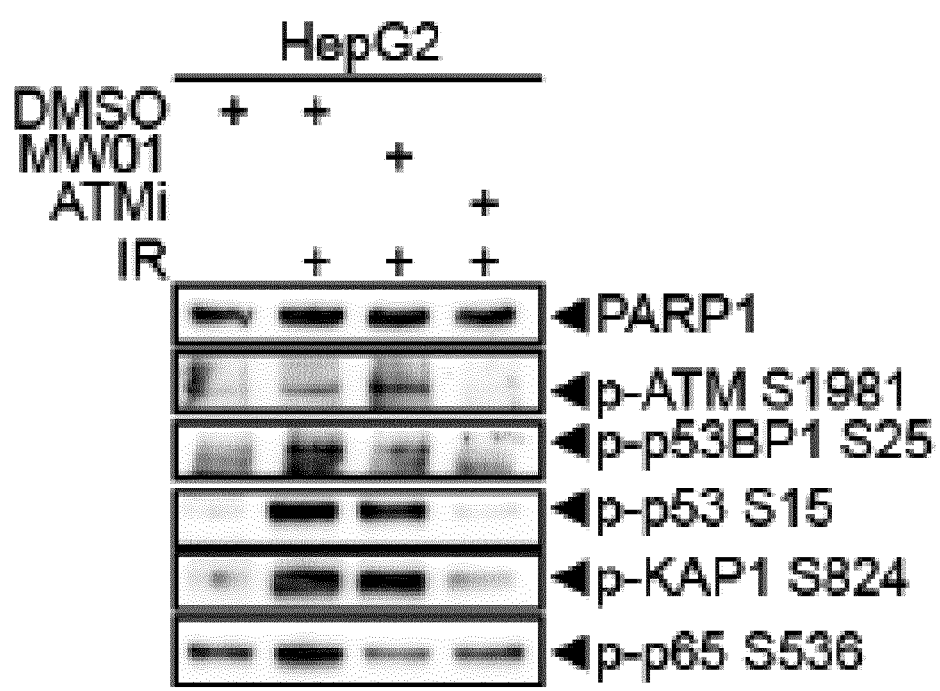
FIG. 9: MW01 does not inhibit enzymatic activity of ATM.

FIG. 9: HepG2 cells were pre-incubated with DMSO, MW01 (5 µM) or the ATM inhibitor Ku55933 (10 µM) and irradiated. After 60 min cells were harvested and processed. Immunochemical staining of Western blotting membranes was done using indicated antibodies.

Figure 10:
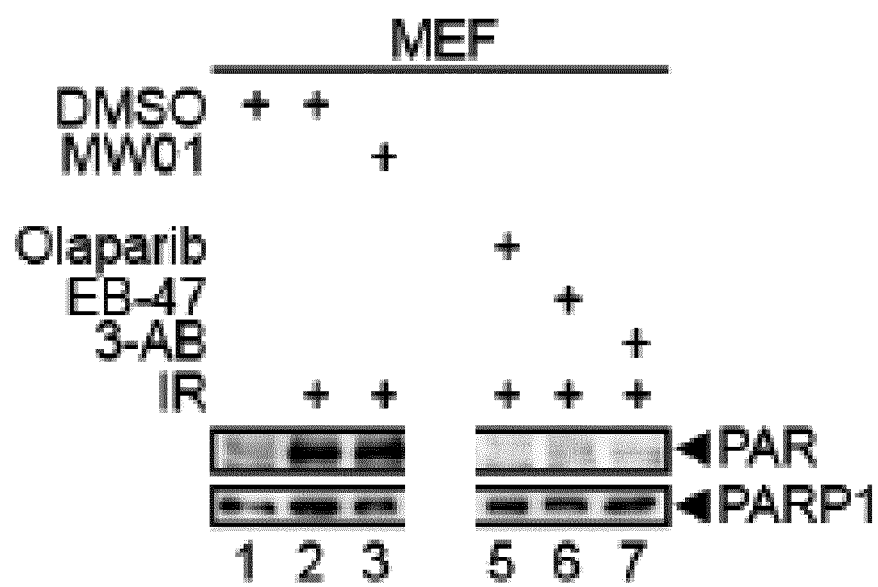
FIG. 10: MW01 do not inhibit the enzymatic activity of PARP1.
Figure 10:
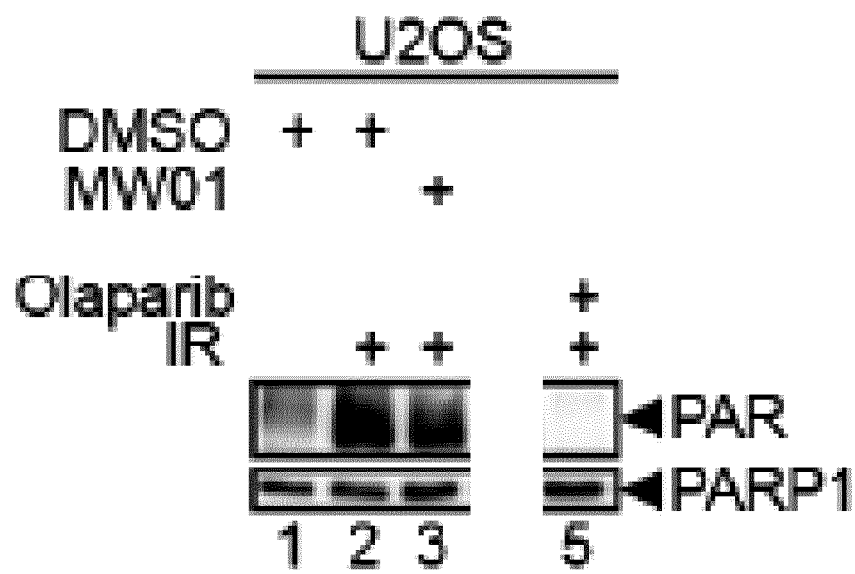

FIG. 10: (A) MEF cells were pre-treated with the indicated substances, irradiated and cell lysates were used for poly(ADP)-ribose probing using a specific antibody. (B) Experiment performed as described for (A), but using U2OS cells.

Figure 11:
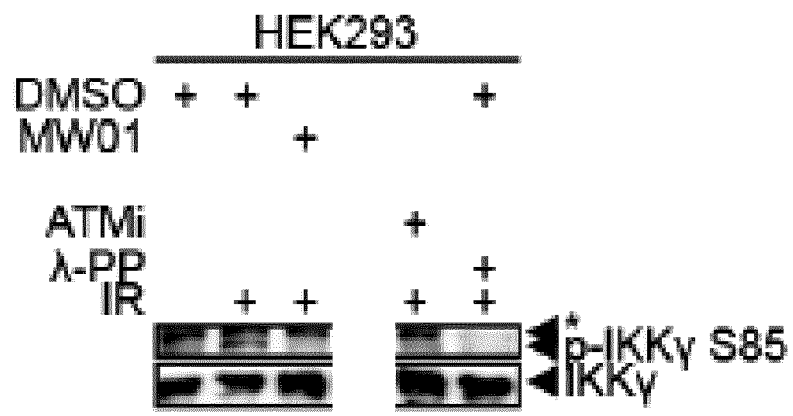
FIG. 11: MW01 inhibits the formation of essential IKKγ post-translational modifications following genotoxic stress.
Figure 11:
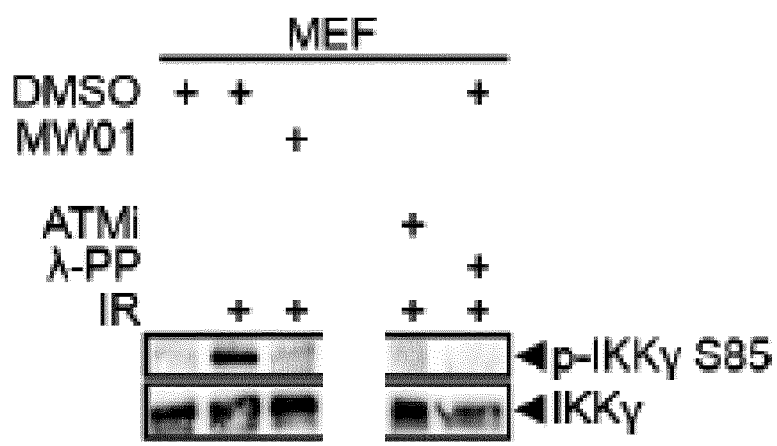
Figure 11:
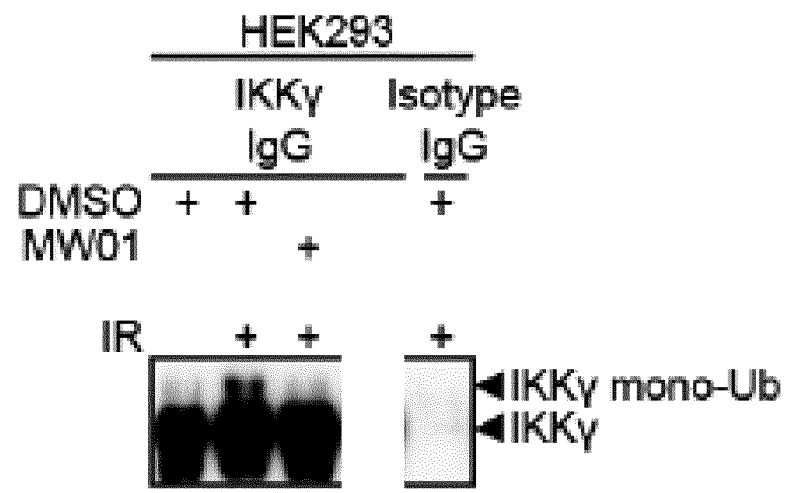

FIG. 11: (A) HEK293 cells were pre-incubated with DMSO, MW01 or ATM inhibitor KU55933 and irradiated. Lysates were subjected to SDS-PAGE/WB. The specific IKKγ S85 band (lower band) was identified by induction following irradiation and by sensitivity to ATMi and λ-phosphatase (λ-PP) treatment. The asterisk indicates a non-specific band that was neither inducible nor ATMi sensitive. (B) Experiment was done as shown in (A) using MEF cells. (C) HEK293 cells were pre-treated with DMSO or MW01, irradiated and lysed. Lysates were used to immunoprecipitate IKKγ using an IKKγ antibody.

Figure 12:
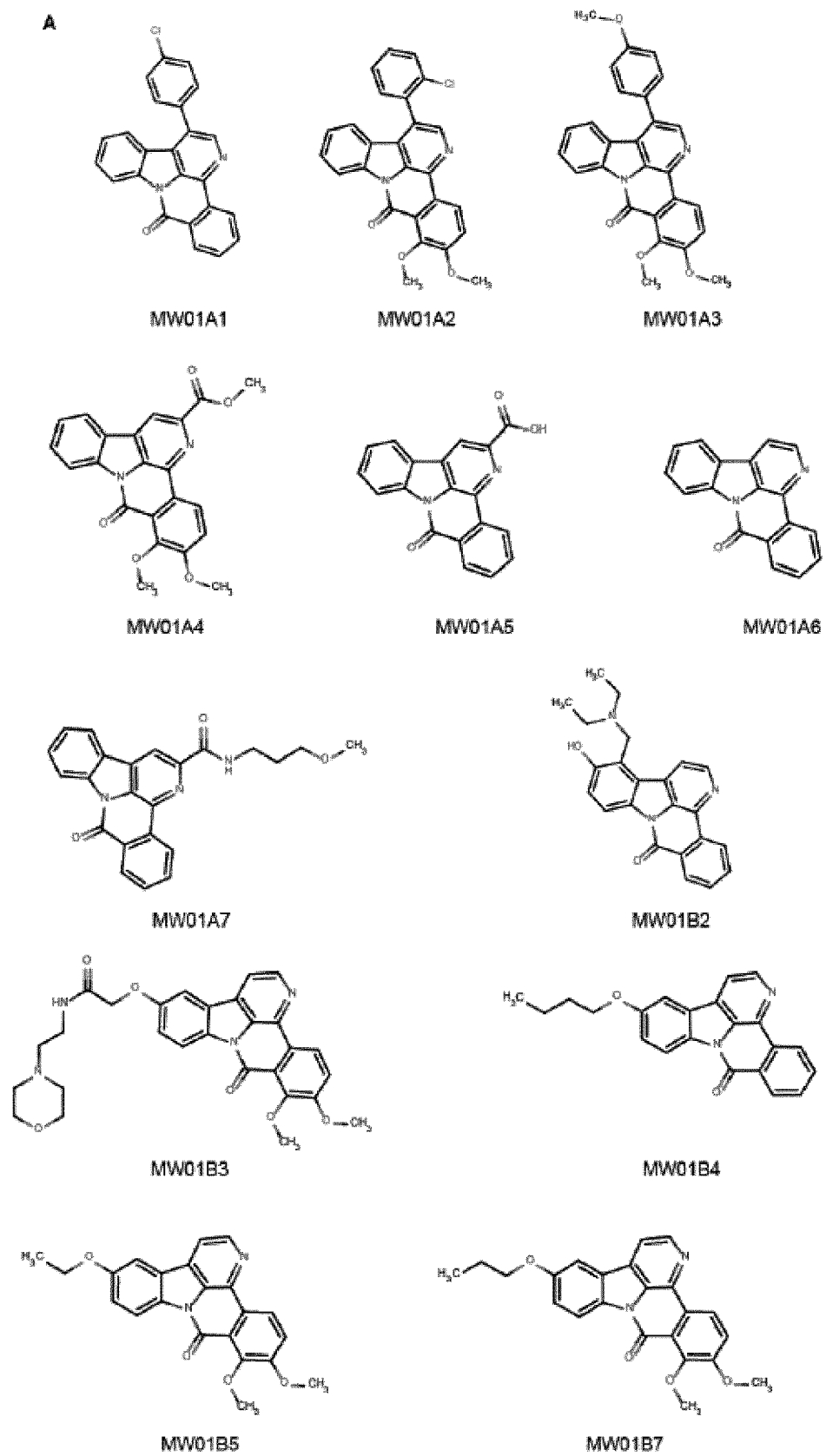
FIG. 12: Overview of the molecule structures of MW01 and derivatives thereof.
Figure 12:
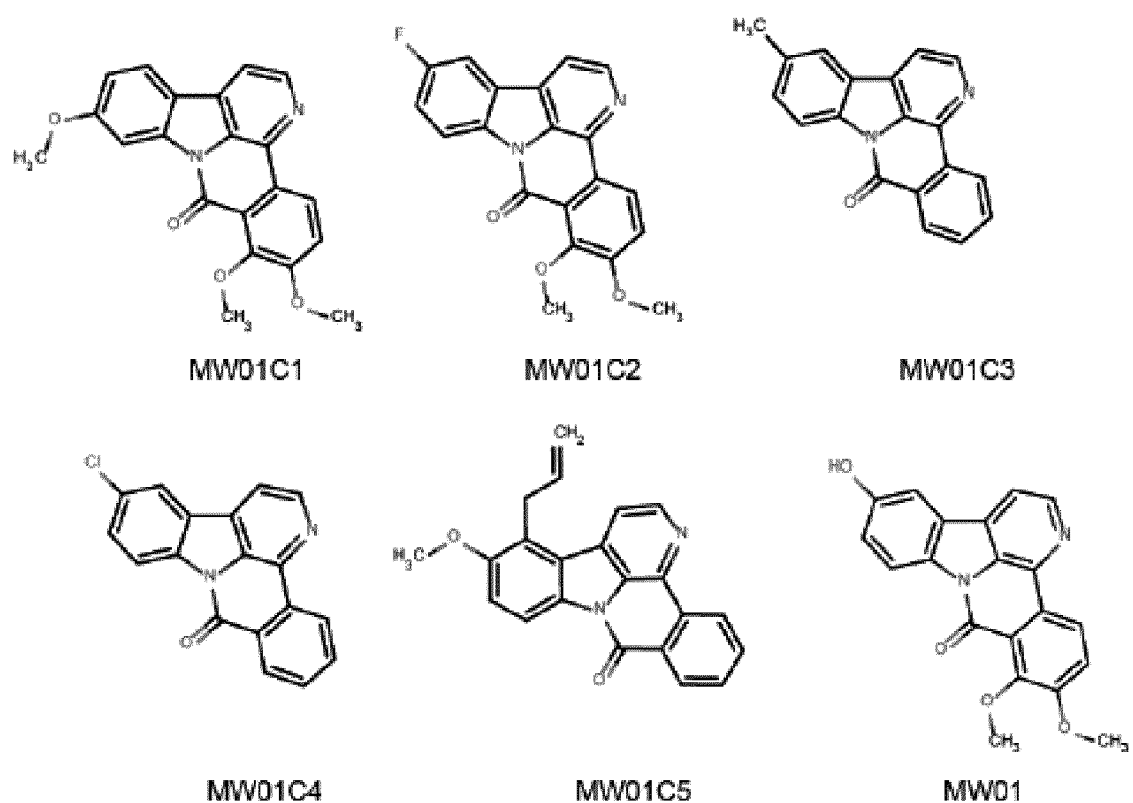
Figure 12:
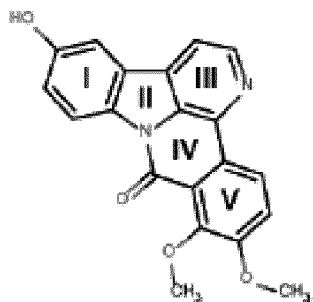
Figure 12:
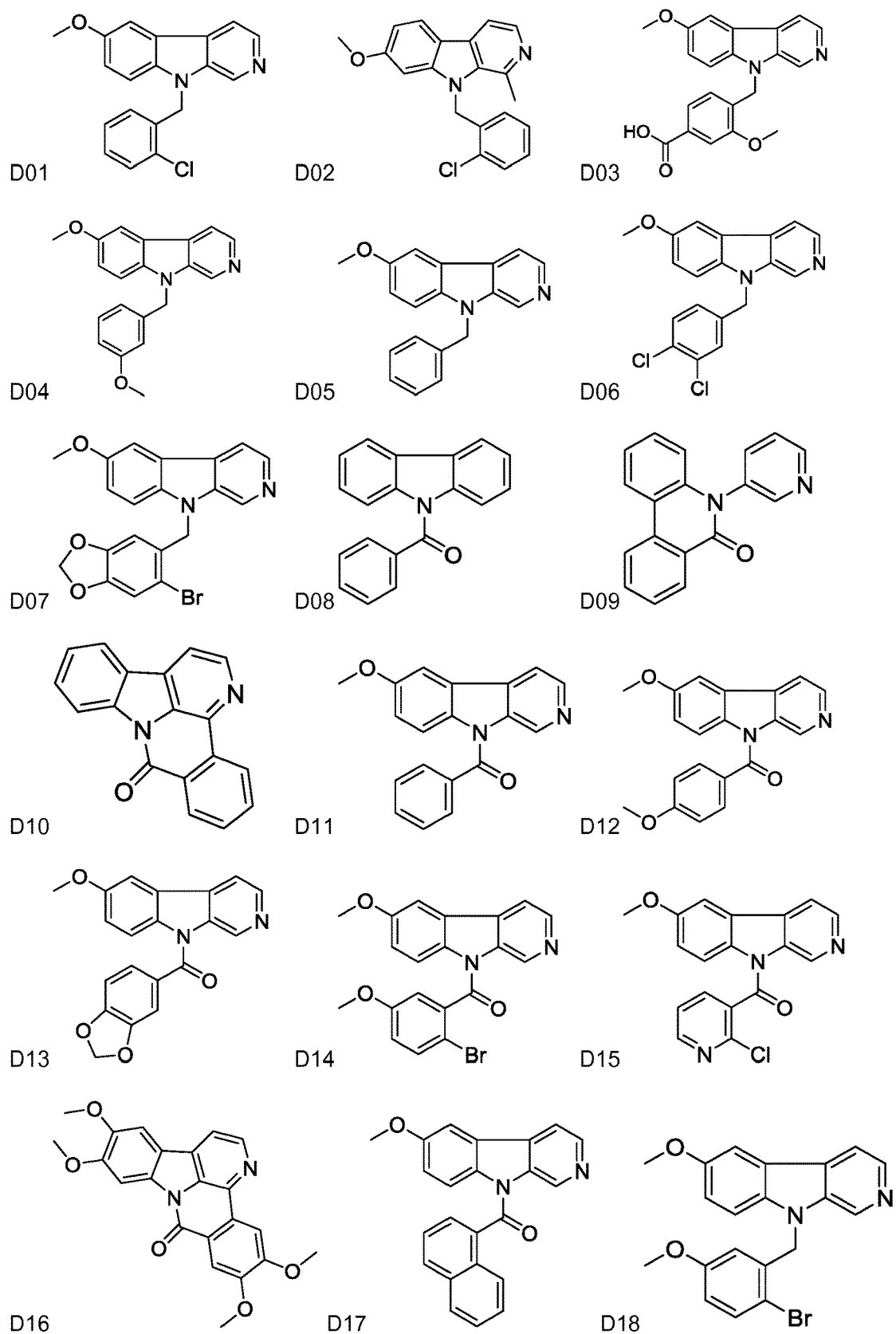
Figure 12:
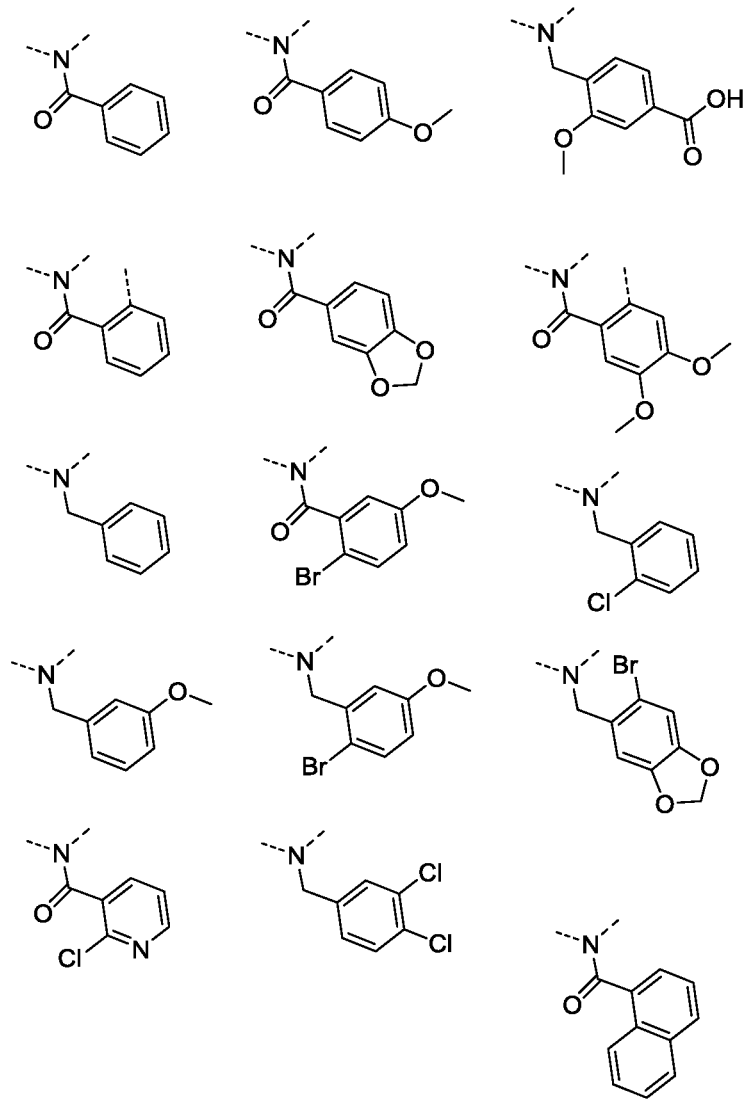
Figure 12:
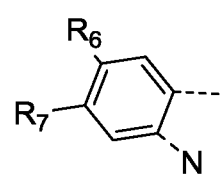

FIG. 12: (A) Molecule structures of MW01 and tested derivatives. (B) Systematic nomenclature of ring systems in the molecule structure of MW01 (Markgraf et al.; 2005). (C) Molecule structures of MW01 and tested derivatives D01-D18. (D) Variations of preferred ring C structures of Formulae I-VII, and preferred ring B structures of Formulae I-VII.

Figure 13:
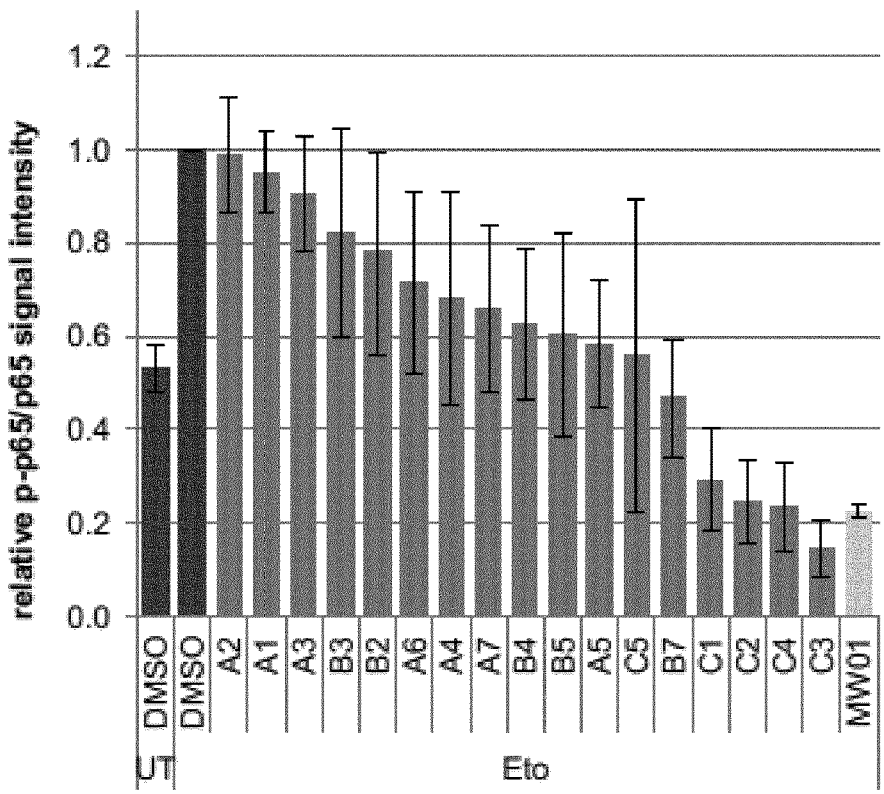
FIG. 13: Structure-activity-relationship analyses of MW01 in comparison to its derivatives.
Figure 13:
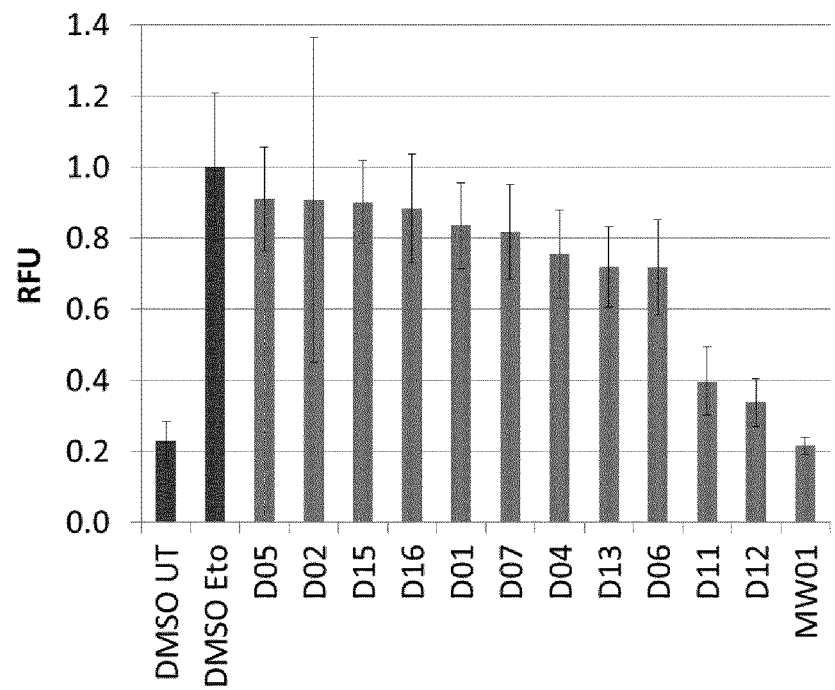

FIG. 13: (A) U2OS cells were pre-treated with DMSO, MW01 or its derivatives MW01A1-MW01C5 at concentrations of 10 µM for 2 h prior to etoposide treatment. After incubation with etoposide cells were harvested, lysed and subjected to SDS-PAGE/WB. Phospho-5536 p65 signal intensities as well as p65 signal intensities were detected using a CCD camera and band intensities were used for densitometrical analyses. DMSO and etoposide treated control was set to 1. Four independent experiments were performed and statistical outliers were identified and eliminated using Grubb's test. The deviation is displayed as the standard error of the mean (SEM). (B) NFkB/293/GFP-luc cells were pre-treated with DMSO, MW01 or its derivatives MW01D01-MW01D18 at concentrations of 10 µM for 1.5 h prior to etoposide treatment. After incubation for 4.5 hours NF-κB-dependent luciferase expression was measured by detection of chemoluminescence. DMSO and etoposide treated control was set to 1. Twelve independent experiments were performed.

Figure 14:
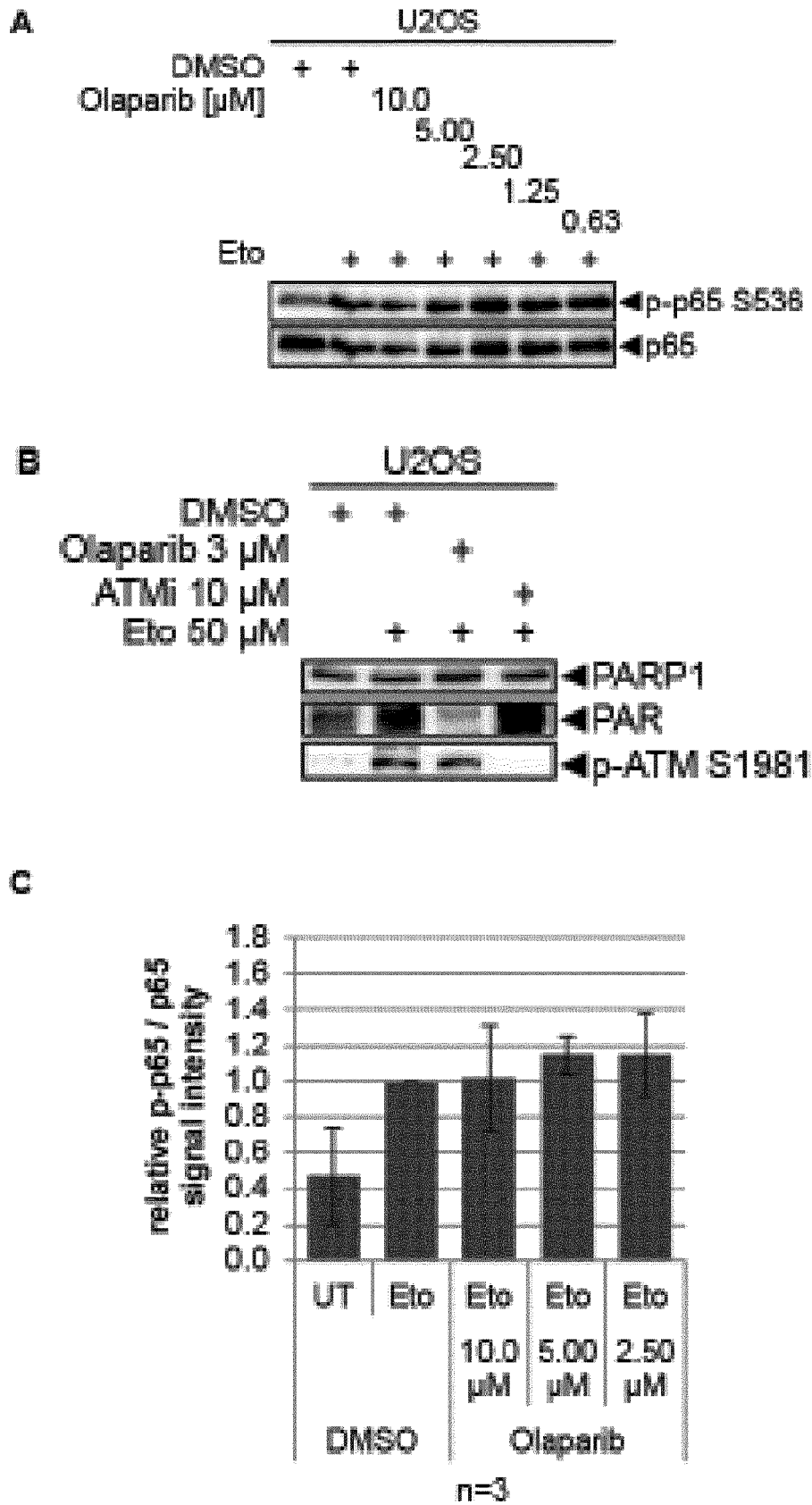
FIG. 14: Inhibition of genotoxic stress-induced NF-κB activation by PARP inhibitors is cell type dependent.
Figure 14:
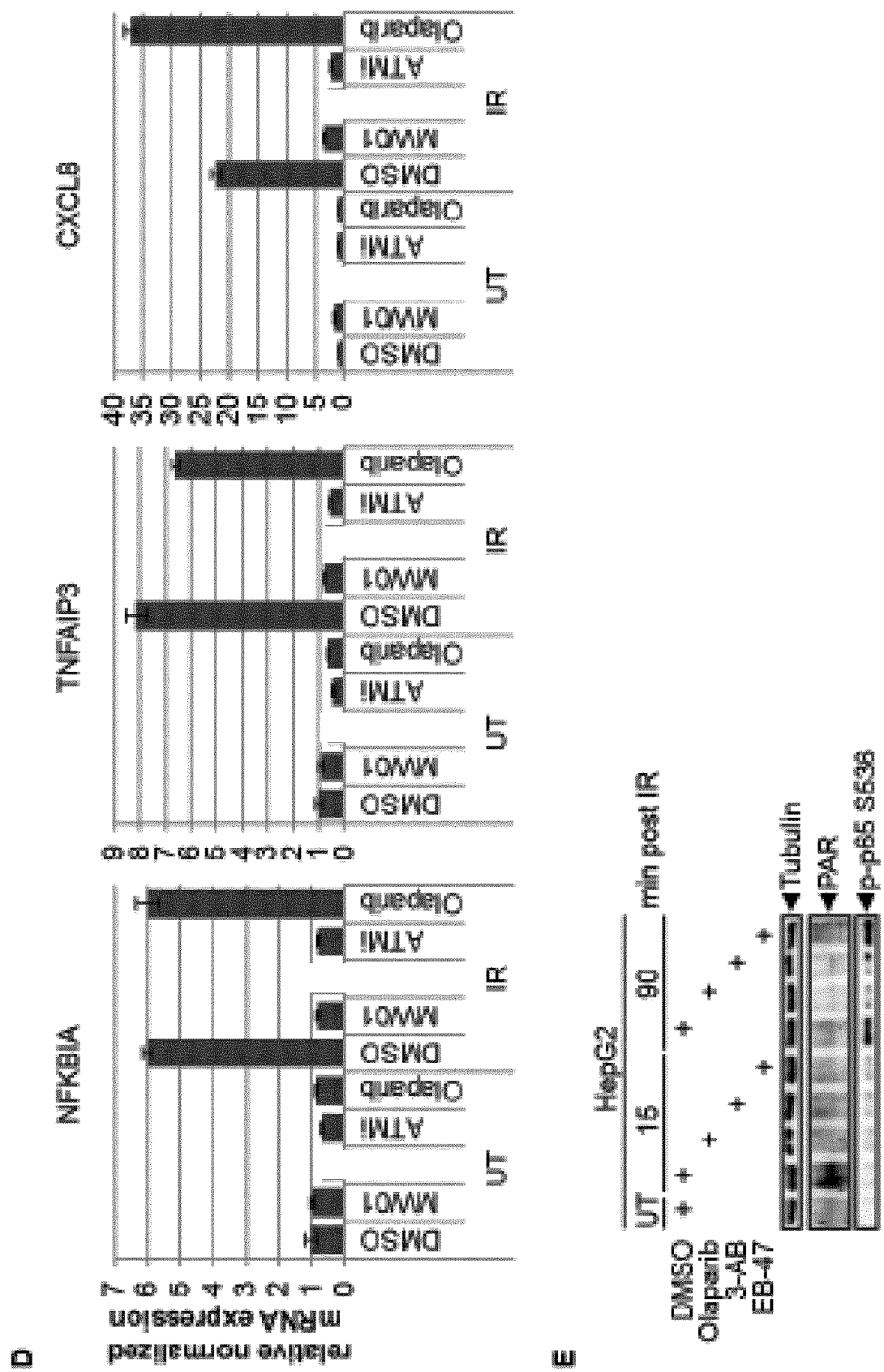

FIG. 14: (A) U2OS cells were pre-treated with different concentrations of olaparib prior to co-treatment with etoposide. Whole cell lysis was performed after 90 min and cleared lysates were used for WB with indicated antibodies. (B) U2OS cells were pre-treated with DMSO, olaparib or the ATM inhibitor Ku55933 and co-treated with etoposide. Cells were harvested after 45 min and subjected to SDS-PAGE/WB. Membranes were stained with the indicated antibodies. The experiment of (B) was performed simultaneously to the experiments of (A) and (E) to control functionality of olaparib in inhibiting PAR chain formation. (C) Densitometrical analyses of (A) and two further independent experiments done as shown in (A). (D) U2OS cells were pre-treated with the substances as indicated prior to irradiation. After 90 min mRNA was isolated, transcribed into cDNA and was used for expression analyses of the indicated genes using quantitative real-time PCR (qRT-PCR). (E) HepG2 cells were pre-treated with the PARP inhibitors olaparib, 3-AB and EB-47 prior to γ-irradiation. Cells were harvested after 15 and 90 min and subjected to SDS-PAGE/ WB. Membranes were stained with the indicated antibodies. Error bars equal SEM.

Figure 15:
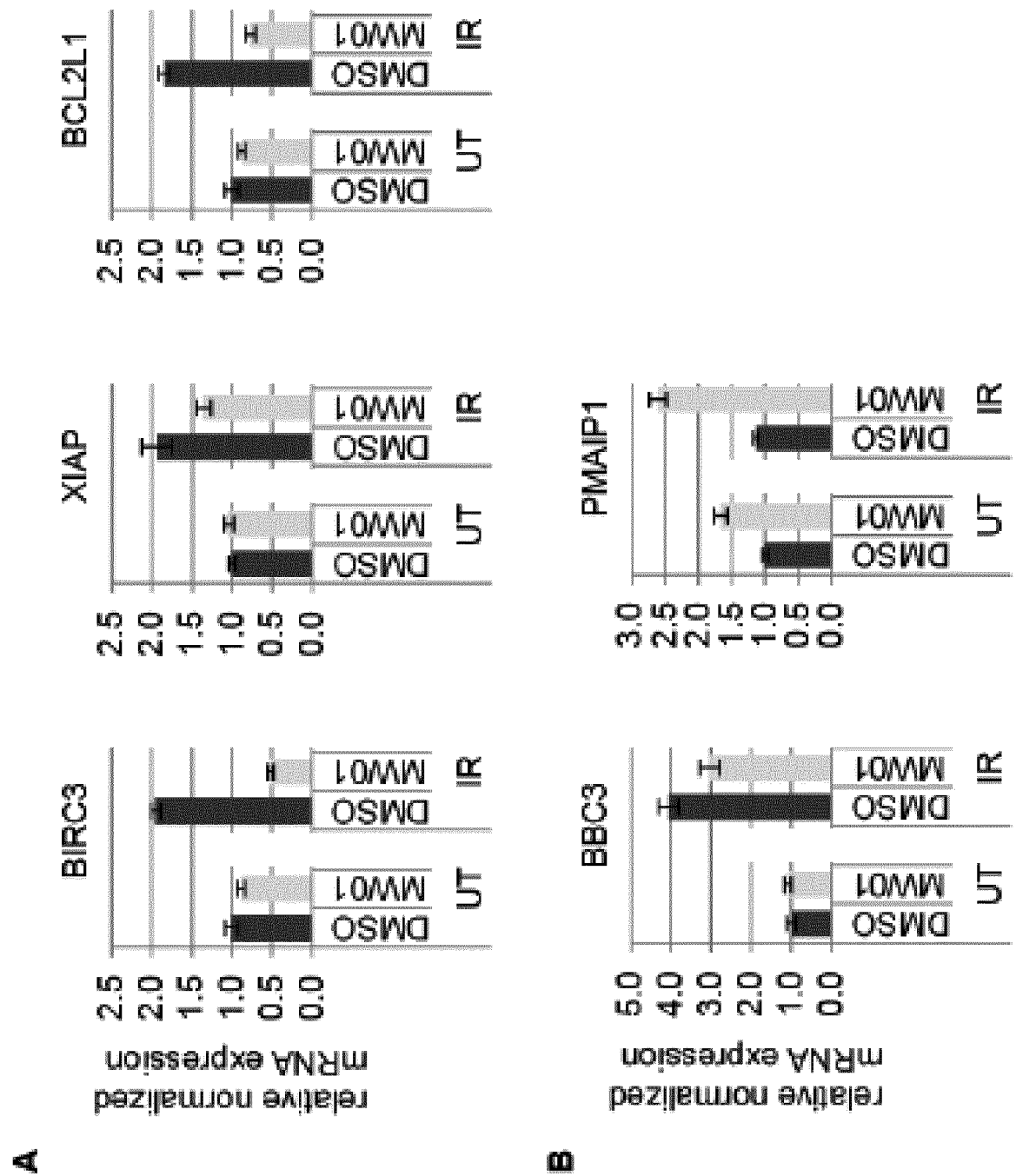
FIG. 15: Influence of MW01 on the mRNA expression of anti- and pro-apoptotic genes following DNA damage.

FIG. 15: (A), (B) U2OS cells were pre-treated with DMSO or MW01 and irradiated. After 8 h mRNA was isolated and reversely transcribed into cDNA. The obtained cDNA was used to perform qRT-PCR using gene specific exon-exon-spanning primers for mRNA of anti-apoptotic (A) and pro-apoptotic genes (B).

Figure 16:
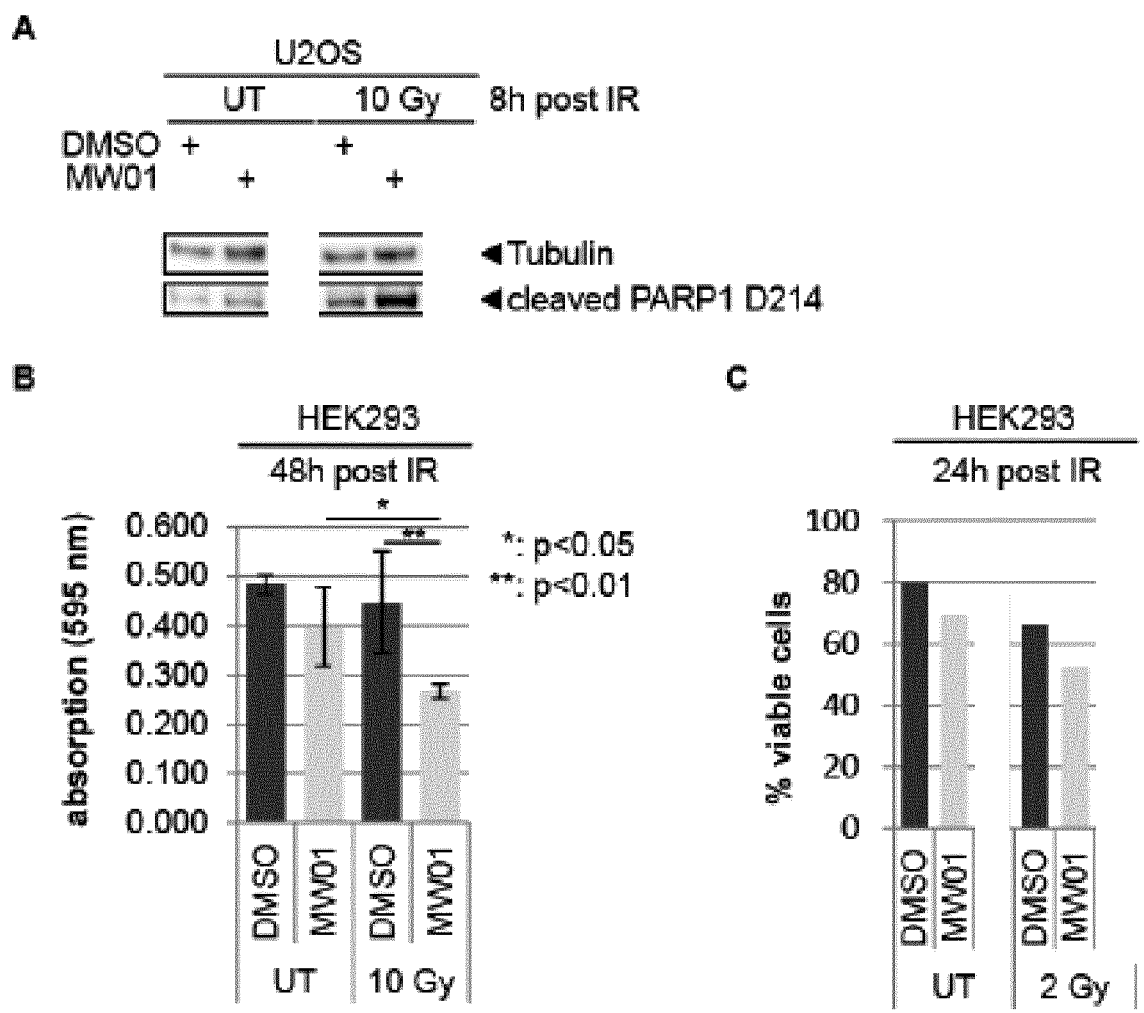
FIG. 16: MW01 increases apoptotic cell death after genotoxic stress.
Figure 16:
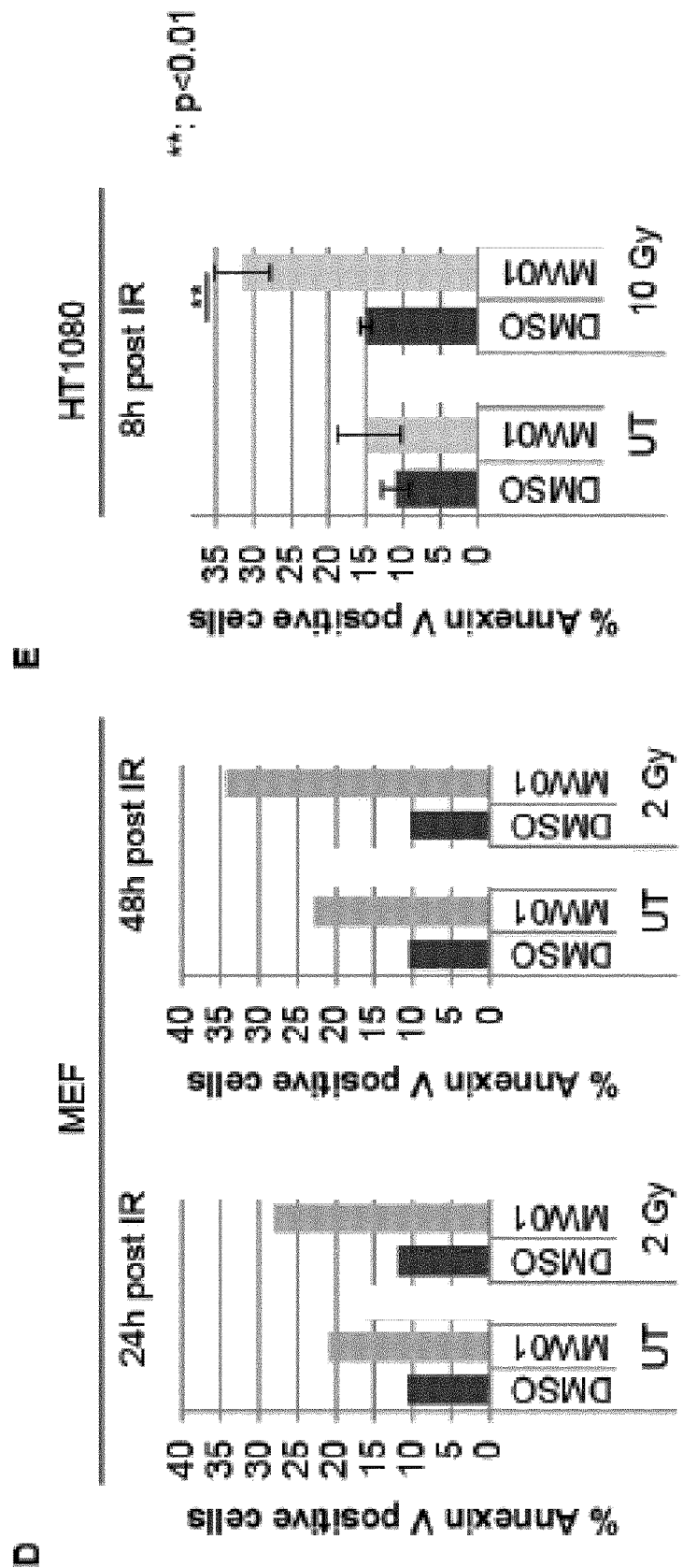

FIG. 16: (A) U2OS cells were pre-treated with DMSO or MW01 and irradiated. Cells were lysed 8 h post γ-IR and were used for western blotting and immunochemical staining. (B) HEK293 cells were pre-treated with DMSO or MW01 and irradiated. After 48 h cells were fixed and stained with crystal violet. Dissolved crystal violet was used for absorbance measurement in a visible light spectrophotometer at a wavelength of 595 nm. (C) HEK293 cells were pre-treated with DMSO or MW01 and irradiated. The percentage of viable cells within the population was calculated by exclusion of annexin V and propidium-iodide positive cells measured by flow cytometry. (D) MEF cells were pre-treated with DMSO or MW01 and irradiated. Cells were used for annexin V staining 24 h and 48 after γ-IR. Percentage of annexin V positive cell population was analysed using a flow cytometer. (E) Experiment done as shown in (D) but with HT1080 cells processed 8 h after irradiation. Statistical significance was calculated using students t-test.

Figure 17:
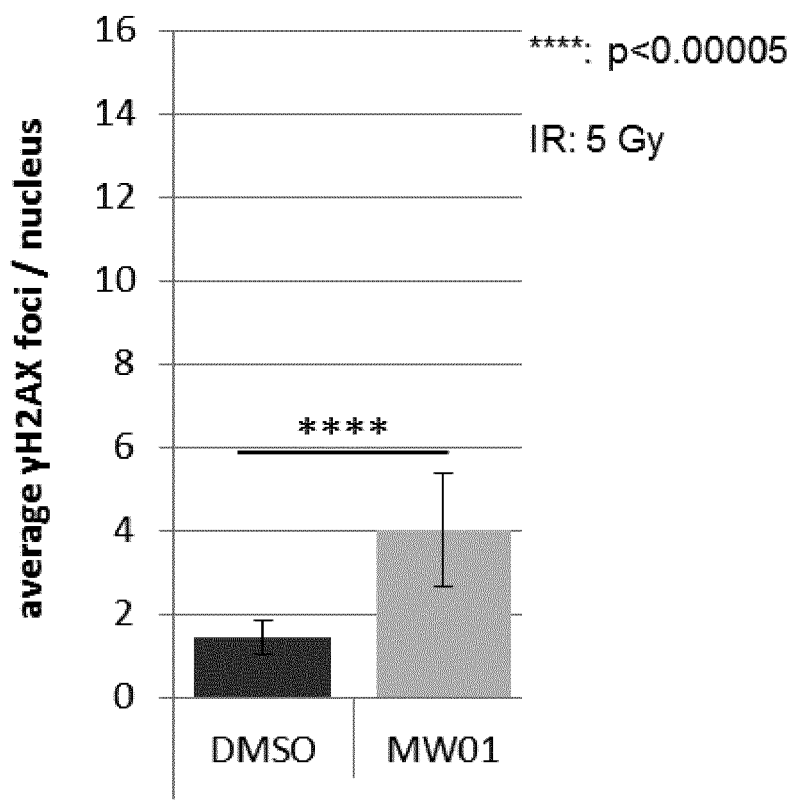
FIG. 17: MW01 significantly increases γH2AX foci per cell in untreated cells.

FIG. 17: U2OS cells grown on coverslips were incubated 30 min with DMSO or MW01 (5 µM). Then, cells were γ-irradiated (5 Gy) or mock irradiated (mock IR). After 5 hours, cells were fixed and subjected to immunofluorescence staining procedure. DNA damage-indicating γH2AX foci and nuclei n≥480 nuclei per condition) were counted for the calculation of average foci per nucleus. Significance was calculated using student's t-test.

EXAMPLES

The invention is further described by the following examples. These are not intended to limit the scope of the invention, but represent preferred embodiments of aspects of the invention provided for greater illustration of the invention described herein.

Methods Employed in the Examples
RNA Isolation

For RNA isolation cells were washed with ice-cold PBS. Isolation of RNA then was performed according to manufacturer's instructions (Qiagen, RNeasy RNA isolation KIT). Integrity of isolated RNA was ensured by measuring the ratio of 28s and 18s ribosomal RNA at a Bioanalyzer using a RNA testing chip (Agilent RNA 6000 Nano Kit) according to manufacturer's instructions.

Determination of Nucleic Acids Concentration

Using a UV light spectrophotometer DNA/RNA concentration was measured at OD260. Protein or chemical contaminations were checked by measurement of ratios of 0D260/280 and OD260/230. Further analyses were performed on samples with 0D260/280 ratios of about 2.

Reverse Transcriptase-PCR and Quantitative Real-Time PCR (c/RT-PCR)

In order to generate complementary DNA (cDNA) 500-1000 ng total RNA was transcribed using the iScript cDNA synthesis Kit (Promega) following manufacturer's instructions.

To quantitate specific mRNA (messenger RNA) species in samples RNA was isolated, RNA concentration was measured and mRNA was transcribed into cDNA. The amount of mRNA transcripts of certain genes within a sample was quantified by employing gene specific primers and using a C-1000 Thermal cycler (Biorad). The expression of genes of interest was normalised against two or three reference genes (HRPT1, RPL_13a and B2M) using the CFX manager software. The fold induction of mRNA was calculated over untreated sample levels by the ΔΔ-Ct method.

Cell Culture

All cell lines were cultured in media supplemented with 10% FCS and penicillin/streptomycin (100 U/ml and 100 µg/ml) in 95% relative humidity and 5% CO2 atmosphere. U2OS and HEK293 cells were cultured in DMEM, mouse embryonic fibroblast were cultured in DMEM Glutamax, and HepG2 cells were cultured in RPMI 1640 medium (all obtained from Gibco). For passaging, cells were washed with PBS, trypsinised with trypsin/EDTA solution at 37° C. until detachment from the plate and suspended in the corresponding medium. Splitting ratios were between 1:3 to 1:5 (U2OS, HepG2) and 1:10 to 1:15 (MEF and HEK293). For cryo-conservation in liquid nitrogen cells were trypsinised at 37° C., suspended in medium and pelleted by centrifugation at 320×g for 5 min. Afterwards, cells were resuspended in freezing medium (corresponding medium supplemented with 20% FCS, 10% DMSO and penicillin/streptomycin) and were frozen in freezing boxes containing isopropanol in a −80° C. freezer. Cells were transferred to liquid nitrogen at the following day. Thawing of cells was done in at 37° C. in a water bath. Partially-frozen cells were pipetted dropwise to 37° C. pre-warmed medium and centrifuged for 5 min at 300×g. Finally, cells were resuspended in fresh complete medium.

For the activation of the canonical NF-κB pathway cells were treated with recombinant human TNFα (10 ng/ml) or IL-1β (10 ng/ml) for 20-30 min at 37° C.

Genotoxic stress was applied by ionizing irradiation of cells with a Cs137 source (0629 Irradiator, STS Braunschweig), or by inhibition of the topoisomerase II enzyme by administration of etoposide at concentrations between 20-50 µM for 2 h.

Immunofluorescence Staining and Confocal Microscopy

For immunofluorescence staining 0.95×10$^5$ cells were seeded in 6 well plates onto autoclaved cover slips. Cellular confluency dictated to beginning of the experiment (2-3 days from seeding). After conduction of experiments cells were washed with PBS and fixed with 4% PFA/double-distilled H$_2$O (ddH2O) for 10 min at RT. Following two additional washing steps cells were incubated with a solution containing 0.12% glycine/0.2% saponin in PBS for 10 min and then blocked with a solution containing 10% FCS/0.2% saponin in PBS for 1 h. Primary antibody incubation was performed overnight at 4° C. (1:500 diluted in 0.2% saponin in PBS). The next day, cover slips were washed five times with a solution containing 0.2% saponin in PBS. Fluorophor-coupled secondary antibodies (1:1000 diluted in 0.2% saponin in PBS) were incubated for 1 h (hour) at RT. Nuclei were stained using 0.2 mg/ml DAPI in PBS for 5 or by directly mounting with DAPI/Mowiol. Finally, the cover slips were washed five times with 0.2% saponin in PBS and two times with ddH2O. Confocal microscopy was performed using a Zeiss 710 LSM with a 40× or a 63× oil objective.

Crystal Violet Staining

For crystal violet staining, cells were washed with ice-cold PBS and fixed with 4% PFA in PBS for 15 min under a fume hood. After washing with PBS, cells were stained with 0.1% crystal violet for 20 min at RT. Afterwards, cells were washed again three times with PBS and were air dried. Cells were incubated with 10% acetic acid for 20 min while shaking. Then, 0.25 ml of stain was diluted 1:4 in ddH2O and absorbance was measured at 595 nm using a spectrophotometer against 10% acetic acid as blank.

Flow Cytometry

Cells were washed with ice-cold PBS and detached from growing dishes using Trypsin/EDTA solution. Detached cells were centrifuged at 300×g for 5 min. Detection of early apoptotic cells was performed by staining with annexin V-FITC antibody according to manufacturer's instructions (eBioscience Annexin V-FITC Apoptosis detection Kit). Necroptotic and late apoptotic cells were stained by addition of propidium iodide (final concentration 1 µg/ml) prior to measurements.

Cell Harvesting

Tissue culture plates of interest were washed with ice-cold PBS. The cells were scraped in PBS using cell scrapers and the cell suspension was transferred to 1.5 ml reaction tubes. Cells were pelleted by centrifugation at 20,000×g for 15 s at 4° C. The supernatant was discarded and cells were snap frozen or lysed directly.

Whole Cell Lysis

Cell pellets were resuspended in 3 volumes of Baeuerle lysis buffer on ice and lysed for 20 min while shaking moderately at 4° C. Samples were centrifuged at 20,000×g for 10 min at 4° C. and the supernatant, representing the whole cell protein extract, was transferred into a new 1.5 ml reaction tube.

Subcellular Fractionation

For the preparation of nuclear and cytoplasmic fractions, cells were lysed with buffer A (supplemented with 1 mM DTT, 10 mM NaF, 20 mM β-glycerophosphate, 250 nM NaVO3, complete protease inhibitor cocktail (Roche) and 50 nM calyculin A. Lysates were adjusted to a final concentration of 0.2% NP-40, vortexed for 10 s and spun down. The supernatant, representing the cytoplasmic extract (CE), was transferred into a new 1.5 ml reaction tube. The pellet was washed with buffer A, was resuspended with buffer C and shaken for 20 min at 4° C. Following 10 min of centrifugation at 14,000 rpm, the supernatant, representing the nuclear extract (NE), was transferred into a new reaction cap.

Determination of Protein Concentration

To determine protein concentration of cell lysates, 1-2 µl of protein extracts were mixed with 1 ml Bradford reagent diluted 1:5 with ddH2O. Absorbance was measured in a spectrophotometer at a wavelength of 595 nm against a lysis buffer reference and was compared to a BSA standard curve.

Immunoprecipitation

Following cell lysis the protein concentration of samples was determined. For input controls, 40 µg lysate were mixed with 6×SDS-buffer and denatured by heating to 95° C. for 4 min. Approximately 1500 µg protein lysate was used for pulldown and samples volumes were equalled with lysis buffer. Lysates were precleared with 30 µl sepharose A or sepharose G beads (depending on the antibody type used for pulldown) for 30 min, and centrifuged for 5 min at 1,500×g. The supernatant was transferred to a new reaction tube.

Primary antibody (2-2.5 µg) was added to the cleared lysate for immunoprecipitation overnight while rotating at 4° C. The next day 30 µl sepharose beads per sample were used for immobilisation of antibodies. Following 4 washes with IP wash buffer precipitated proteins were eluted by mixing with 3×SDS-buffer and heating to 95° C. for 4 min.

Sodium Dodecyl Sulphate Polyacrylamide Gel Electrophoresis (SDS-PAGE)

For preparation of cell lysates for SDS-PAGE 20-40 µg of protein lysates were mixed with 6× reaction buffer and heated to 95° C. for 4 min. After boiling samples were loaded into a polyacrylamide gel. Gels were casted consisting of a separating gel and a stacking gel. The concentration of acrylamide within the separating gels was depending on the experiment and the desired separation between certain molecular weights, but generally ranged between 8% and 12%.

| Stacking gel | |
|---|---|
| Tris-HCl, pH 6.8 | 125 mM |
| Acrylamide | 5% |
| SDS | 0.1% |
| APS (ammonium persulphate) | 0.1% |
| TEMED | 0.1% |
| Separation gel | |
| Tris-HCl, pH 8.8 | 375 mM |
| Acrylamide | 8-12% |
| SDS | 0.1% |
| APS | 0.075% |
| TEMED | 0.05% |

After sample loading a voltage of 80 V was applied to allow protein concentration at the border line of stacking and separating gel. Afterwards, voltage was increased to 140 V and proteins were separated for circa 2 h.

Western Blotting

Proteins separated by SDS-PAGE (6.3.5) were immobilised by Western blotting (WB) to methanol-activated PVDF membrane using transfer buffer and a semi-dry blotting apparatus. Proteins were transferred to membranes by applying a constant current of 80 mA per 6×9 cm membrane for 90 min. For the transfer of small proteins (<30 kDa) the blotting time was reduced to 30 min.

Immunochemical Detection of Proteins on Membranes

After transfer of proteins on PVDF membranes unspecific binding of antibodies was blocked by incubation of membranes in 5% skim milk powder in TBST buffer (or 3% BSA in TBST for phosphorylation-specific antibodies) for 1 h at RT. Membranes were incubated overnight at 4° C. with a solution of primary antibody in 5% skim milk powder in TBST or 3% BSA in TBST (phosphorylation-specific antibodies) diluted 1:1000. The next day membranes were washed three times with TBST for 5 min. Then, membranes were incubated for 1 h with a HRP-coupled secondary antibody (1:10000) directed against the FC-part of the used corresponding primary antibody. After three times of washing with TBST and once with PBS for 5 min, chemiluminescent photon emission was detected using a CCD camera system (Fusion Solo). Enhanced chemiluminescence (ECL) solution (Millipore) was used as HRP substrate.

Membranes were stripped to allow subsequent probing with multiple antibodies using Restore PLUS WB Stripping buffer (Thermo Scientific) for 35 min at RT. After extensive washing with TBST, membranes were blocked again with 5% skim milk powder in TBST for 1 h and were incubated with the next primary antibody overnight.

H2K/NF-κB Oligonucleotide Preparation

Oligonucleotides were ordered as high-performance liquid chromatography (HPLC) purified BamHI ends. For annealing 5 µg of each strand were incubated for 10 mins at 90° C. in 50 µl annealing buffer resulting in a final concentration of 200 ng/µl. Hybridized oligonucleotides were allowed to cool down over night in the thermal block and stored at −20° C. afterwards. Annealing of oligonucleotides was analysed in a 12% polyacrylamide gel by comparing 1 µg of hybridized oligonucleotides with 1 µg single strand oligonucleotides.

Radioactive Labelling and Purification of NF-κB Oligonucleotides

For radioactive labelling of the H2K/NF-κB probe, the reaction recipe was followed and the mixture was incubated for 15 minutes (min) at 25° C. The purification of radioactive labelled NF-κB probe was done using the QIAquick Nucleotide Removal Kit (Qiagen) according to the manufacturer's instructions. Radioactive labelling was measured using a scintillation counter. Radioactive probe was stored at −20° C.

Labelling Recipe:
H2O 10.2 µl
DNA-Oligonucleotide (200 ng) 1.0 µl
10× Klenow buffer 2.5 µl
dCTP, dGTP, dTTP (2 mM each) 1.8 µl
α[32P] dATP 7.5 µl (3 MBq)
DNA Pol I (Klenow fragment, 5 U/µl) 0.2 µl (1 U)
Electro Mobility Shift Assay (EMSA)

Nuclear or whole cell lysates were incubated with a $^{32}$P-labeled NF-κB DNA-consensus
sequence. The shift mixture was prepared following the shift mixture recipe:
Shift mixture for EMSA (H2K/NF-κB)
total lysate 3-5 µg
2× shift buffer 10.0 µl
BSA (10 ng/µl) 1.0 µl
DTT (100 mM) 0.4 µl
Poly dI-dC (2 µg/µl) 1.0 µl
$^{32}$P-labeled oligonucleotide 45,000 cpm
ddH2O ad 20 µl
The shift mixture was incubated for 30 min at 37° C. before the samples were loaded onto an
EMSA gel:
EMSA gel recipe (native polyacrylamide gel)
ddH2O 44 ml
10×TBE 6 ml
Acrylamide (30%) 10 ml
APS (10%) 450 µl
TEMED 45 µl
For electrophoresis, a current of 26 mA was applied for 2 h. After drying the gel onto a Whatman paper, signals were visualised on an autoradiography film (GE Healthcare) after overnight incubation at −80° C. in a radiography cassette. All work using radioactive substances were done at a monitored work space suitable for radioactive work.

Results of the Examples

Identification of MW01 by High Content Screening

In order to identify specific inhibitors of the DNA damage-induced NF-κB pathway, a differential screening assay was designed. The primary screening for inhibitors of genotoxic stress-induced NF-κB signaling utilised a library of compounds from ChemBioNet and donated compounds of academic chemists. DNA damage was applied by application of etoposide. All compounds which inhibited p65 nuclear translocation were taken for subsequent counter screening. For the counter screening administration of TNFα was used to induce canonical NF-κB signaling. All substances inhibiting TNFα-induced canonical NF-κB activation were discarded from the list of potential DNA damage-pathway specific substances.

Based on its $IC_{50}$ value of 0.46 µM, its percentage in activity change of 120% (as recorded in $IC_{50}$ determination assay) and the calculated Hill coefficient of –0.9, compound MW01 was chosen for further analyses. MW01 was identified as a shown to specifically selective inhibition of genotoxic stress induced IKK/NF-κB activation, as it inhibited NF-κB activation in response to etoposide stimulation, but not after TNFα stimulation.

Validation of Compound MW01 as a DNA Damage-Specific NF-κB Inhibitor

MW01 Inhibits NF-κB Activation Upon Genotoxic Stress

The small molecule MW01 was identified as the most promising genotoxic stress-specific NF-κB inhibitor by differential discrimination but needed further validation with material from another provider. Therefore, a fresh stock of lead compound MW01 was obtained from vendors, solved in DMSO and tested for reproducible inhibition of etoposide-induced p65 nuclear translocation using IF staining of p65 (FIG. 2). Additionally, γH2AX foci as a sensitive marker for DNA DSB were visualised. As performed in the differential screening, pre-treatment of cells with MW01 inhibited p65 translocation upon DNA DSB-induction by the administration of etoposide.

The measured $IC_{50}$ curves of MW01 indicated that MW01 inhibited the nuclear translocation of p65 upon etoposide stimulation in a concentration dependent manner (FIG. 3A) and a concentration of 5 µM was sufficient for maximal inhibition of p65 nuclear translocation.

In addition to etoposide treatment, γ-irradiation of cells was used as an alternative way to induce DNA damage in further experiments. The pre-treatment of cells with MW01 inhibited the γ-IR-induced NF-κB DNA binding activity and p65 phosphorylation at S536 (FIG. 3B), thus showing etoposide-independent inhibition of NF-κB. As observed for etoposide treatment, the pre-treatment with MW01 also led to a concentration dependent inhibition of p65 S536 phosphorylation following γ-IR (FIG. 3C). In addition to p65 nuclear translocation and p65 S536 phosphorylation, etoposide-induced NF-κB DNA binding activity was also inhibited by MW01 pre-treatment in a concentration dependent manner (FIG. 3D).

Taken together, the concentration-dependent inhibition of p65 S536 phosphorylation by MW01 (FIG. 3C) is in perfect agreement with the corresponding results on the observed inhibition of p65 nuclear translocation (FIG. 3A).

Hence, the analysis of p65 nuclear translocation, p65 S536 phosphorylation and of NF-κB DNA binding activity, validates MW01 as genuine inhibitor of genotoxic stress-induced NF-κB activation.

MW01 does not Inhibit Canonical NF-κB Activation

Canonical NF-κB signaling is initiated by the binding of extracellular ligands to their cell membrane bound receptors, which initiate an intracellular signaling cascade ultimately activating the IKK complex and consequently NF-κB. MW01 was tested in experiments using TNFα to stimulate NF-κB activity in order to confirm specificity for the genotoxic stress-induced NF-κB activation.

MW01 did not interfere with p65 nuclear translocation rates at different concentrations (FIG. 4A). In addition, pre-treatment of cells with MW01 at concentrations of 10 µM and 20 µM had no effect on p65 S536 phosphorylation (FIG. 4B). Furthermore, pre-treatment of cells with MW01 did not interfere with induced NF-κB DNA binding activity upon TNFα stimulation (FIG. 4C).

This experiment was performed in HEK293 cells and substantiated the cell line independent inhibitory effect of MW01.

Genotoxic stress-induced and IL-1β stimulated NF-κB activation share the ubiquitin E3 ligase TRAF6 as an important signaling module. Upon activation, TRAF6 is auto-modified with K63-linked ubiquitin chains, which serve as a scaffold for the recruitment of TAK1 via its adaptor protein TAB2 (Hinz et al.; 2010).

Therefore, MW01 was analysed to investigate, whether they would interfere with IL-1β-induced NF-κB activation.

Pre-treatment with both compounds neither inhibited p65 S536 phosphorylation nor NF-κB DNA binding activity following IL-1β stimulation (FIG. 5A). Furthermore, MW01 was tested for their impact on IKK activation and p65 S536 phosphorylation at high concentrations up to 100 µM, but had no effect on the phosphorylation state of IKK or p65 (FIG. 5B).

In summary, MW01 did not inhibit canonical NF-κB signaling induced by either TNFα or IL-1β stimulation and thus showed specificity for the DNA damage-induced NF-κB pathway.

MW01 Inhibits the Nuclear-to-Cytoplasmic Signal Transduction that is Required for DNA Damage-Induced NF-κB Activation Inhibition of Genotoxic Stress-Induced NF-κB Activation by MW01 Takes Place Upstream of TAK1 Activation TNFα and IL-1β-induced NF-κB activation is dependent on signaling cascades involving TAK1 and IKK activation by phosphorylation upstream of IκBα and p65 phosphorylation. Signaling dynamics of MW01 pre-treated cells were analysed to rule out the possibility that the compounds inhibit NF-κB activation downstream of TAK1 in a genotoxic stress-dependent manner (FIG. 6).

Cells were pre-treated with MW01, γ-irradiated and harvested at indicated time points in a time course experiment (FIG. 6A). Pre-treatment of cells with MW01 led to the complete inhibition of IκBα phosphorylation at 45 min and 60 min after γ-IR.

Similarly, p65 S536 phosphorylation at 45 min and 60 min after γ-IR was inhibited by MW01. Given that IκBα phosphorylation is a consequence of IKK activation, the phosphorylation state of IKK was analysed in the next step (FIG. 6B). The pre-treatment of cells with MW01 also abolished IKK phosphorylation 90 min after irradiation.

The kinase TAK1 is located upstream of IKK in the pathway and is similarly activated by phosphorylation. MW01 pre-treatment strongly inhibited TAK1 phosphorylation at 45 and 60 min following irradiation (FIG. 6C). This result was also true in HepG2 cells. TAK1 and p65 phosphorylation were abolished by pre-treatment with MW01, although ATM was phosphorylated as a consequence of γ-IR (FIG. 6D). Of note, the repeated inhibition TAK1 and p65 phosphorylation in HepG2 cells indicated general, cell line independent inhibitory function of MW01 on genotoxic stress-activated NF-κB signaling.

Taken together, these results strongly suggest that the inhibited step within the genotoxic stress-initiated NF-κB signaling cascade upstream of TAK1 activation.

MW01 Inhibits Genotoxic Stress-Induced NF-κB Activation by Blocking the Cytoplasmic Accumulation of ATM The DNA DSB-activated kinase ATM is mainly localised in the nucleus, but translocates into cytoplasm upon DNA damage. Hinz et al. (2010) showed that the accumulation of activated ATM within the cytoplasm and membrane fractions leads to the activation and subsequent autoubiquitination of TRAF6 with K63-linked ubiquitin chains. The polyubiquitin chains serve as a scaffold for the recruitment of signaling components, including TAK1 and the IKK complex (Hinz et al.; 2010). Thus, this nuclear-to-cytoplasmic signaling cascade leads to the activation of the IKK complex by a mechanism that requires the cytoplasmic translocation of ATM.

To analyse the impact of MW01 on the DNA damage-induced ATM accumulation in the cytoplasm following γ-IR, fractionation experiments were performed. Pre-treatment of cells with MW01 did not affect detection of phosphorylated ATM in nuclear extracts at 45 min and 90 min after irradiation (FIG. 7 A) (compare lanes 2-3 with lanes 5-6). However, detection of activated ATM species in the cytoplasmic extracts was abolished in MW01 pre-treated samples (compare lanes 8-9 with lanes 11-12). The analysis of total ATM amounts revealed that pre-treatment of cells with MW01 inhibited the accumulation of ATM in the cytoplasm at 45 min after irradiation (FIG. 7 A) (compare lane 8 with lane 11). Same results were obtained when U2OS instead of HepG2 cells were tested (data not shown). Furthermore, the effect of MW01 on ATM relocalisation upon DNA DSB was analysed by IF (FIG. 7 B). Irradiation led to strong ATM translocation into the cytoplasm and to the cellular periphery. In contrast, in MW01 treated samples ATM was predominantly localized within the nucleus. The results of the IF imaging strongly support those observed in the fractionation experiments.

The results of the fractionation experiments indicated that the targeted signaling step by MW01 is at the level of ATM cytoplasmic translocation and possibly upstream. Therefore, ATM-mediated TRAF6-autoubiquitination was not further analysed. Hence, considering the results obtained for IL-1 n-stimulated NF-κB activation (FIG. 5 B), it is plausible that TRAF6 activation is not targeted directly, but abolished by both compounds as a result of the inhibited cytoplasmic accumulation of ATM MW01 Inhibits DNA Damage-Induced NF-κB Activation Downstream of PARP1 and ATM Activation The Formation of the Nuclear PARP1-Signalosome is Inhibited by MW01

The formation of a nuclear IKKγ-PIASy-PARP1-ATM signalosome is important to trigger the genotoxic stress-induced NF-κB signaling cascade. The formation of this signalosome requires PARP1, whose enzymatic activity is activated by DNA DSB to attach poly-(ADP)-ribose (PAR) chains onto its substrates and onto itself. These polymers serve as a scaffold for the recruitment of the remaining components of the signalosome (Stilmann et al.; 2009). The influence of MW01 on signalosome formation was analysed by interaction studies using co-immunoprecipitations (Co-IP). The immunoprecipitation of PIASy led to the γ-irradiation-induced Co-IP of phosphorylated ATM-51981 species, which was lost after pre-treatment with MW01 (FIG. 8 A). Next, the interaction between PARP1 and IKKγ was analysed by immunoprecipitation of IKKγ. PARP1 was co-immunoprecipitated with IKKγ from not-irradiated and γ-irradiated cell lysates. Importantly, PARP1 was not co-immunoprecipitated with IKKγ after pre-treatment with MW01 (FIG. 8 B). That MW01 abrogated Co-IP of PARP-1 with IKKγ was also observed in HEK293 cells (data not shown), indicating cell type independent mode of action.

Next, HEK293 cells were used to examine the effect of MW01 treatment on the IKKγ-PIASy-interaction. The PIASy co-immunoprecipitation with IKKγ was inducible and dependent on γ-irradiation, but the interaction was abolished when cells were treated with MW01 (FIG. 8 C). In addition, murine MEF were used for further species and cell type independent generalisation of these findings (FIG. 8 D). As seen in HepG2 or HEK293 cells, MW01 pre-treatment led to the abrogation of the interaction of IKKγ with PARP1, p-ATM S1981 or PIASy, whereas the interactions were shown for DMSO pre-treated samples. The species independent inhibition of the signalosome formation by MW01 indicates that the mode of action is based on a general and conserved mechanism.

MW01 does not Inhibit the Enzymatic Activity of ATM

Activation of the cellular DDR to DNA DSB is strongly dependent on the activity of the serine-kinase ATM. Activated ATM can phosphorylate a plethora of substrates within the mammalian cell and regulates cell cycle arrest, DNA repair or apoptosis (Shiloh and Ziv; 2013). Similarly, it is an essential component of the genotoxic stress-mediated NF-κB signaling pathway (Hinz et al.; 2010).

Therefore, the enzymatic activity of ATM was analysed in cells pre-treated with MW01 after γ-irradiation. MW01 was tested in comparison to the ATM inhibitor KU55933 in order to show that the phosphorylation of the different substrates indeed is ATM dependent. The treatment of cells with KU55933 inhibited the ATM auto-phosphorylation and the phosphorylation of the ATM substrates p53BP1, p53 and KAP1. Despite pre-treatment of cells with MW01 had mild effects on the phosphorylation state of p53bp1, no effects on the phosphorylation state of ATM and the other substrates p53 and KAP1 were observed compared to the solvent and the ATMi control. In addition, MW01 pre-treatment did not lead to impaired phosphorylation of the ATM substrate histone H2AX after etoposide treatment as already shown in FIG. 2. Importantly, MW01 treatment drastically reduced p65 S536 phosphorylation level (FIG. 9).

Taken together, the analyses of ATM auto-phosphorylation and substrate phosphorylation show that the enzymatic activity of ATM is not affected by pre-treatment of cells with MW01.

MW01 does not Inhibit the Enzymatic Activity of PARP1.

Stilmann and colleagues described that the enzymatic activity of PARP1 was essential for PARP1 signalosome formation and recruitment of other signaling components to initiate the DNA damage-induced NF-κB signaling cascade (Stilmann et al.; 2009). Therefore, the influence of MW01 on PARP1 enzymatic function was analysed. Upon γ-irradiation, a strong band was detected using a PAR chain specific antibody in DMSO and MW01 pre-treated samples in MEF and U2OS cells (FIG. 10 A-B). In contrast, pre-treatment of cells with the PARP inhibitors EB-47, 3-AB (FIG. 10 A) or the clinically approved drug Olaparib (Mullard; 2014) led to the inhibition of PAR chain formation (FIG. 10 A+B). Thus, it was shown that MW01 did not interfere with activation of PARP1 enzymatic activity in human and murine cells.

MW01 Inhibits the Formation of Essential Post-Translational Modifications of IKKγ Following Genotoxic Stress The formation of the PARP1 signalosome upon irradiation is a prerequisite for DNA damage-induced NF-κB signaling, because IKKγ needs to be subjected to at least 3 different PTMs. Following DNA DSB, IKKγ is SUMOylated by PIASy within the PARP1 signalosome (Stilmann et al.; 2009). Then, ATM phosphorylates IKKγ at Serine 85 (Z. H. Wu et al.; 2006). As a consequence of the activated signaling cascade IKKγ is mono-ubiquitinated by cIAP1 (Hinz et al.; 2010).

In order to analyse the influence of MW01 on the ATM-dependent IKKγ phosphorylation at S85, cells were pre-treated with the compounds prior to irradiation. MW01 pre-treatment as well as the inhibition of ATM abolished the phosphorylation of IKKγ at S85 in human (FIG. 11 A) and in murine cells (FIG. 11 B).

MW01 pre-treatment abolished IKKγ S85 phosphorylation as well as the inhibition of ATM. Treatment of lysates with λ-protein phosphatase prior to subjection to SDS-PAGE was used as an additional control to show that the detected bands indeed were phosphorylation dependent.

Next, the IKKγ mono-ubiquitination, which is a prerequisite for IKK complex activation (Hinz et al.; 2010), was analysed by immunoprecipitation of IKKγ. The characteristic band of the IKKγ mono-ubiquitinated species (Hinz et al.; 2010) was only detected in the DMSO pre-treated and irradiated sample. Pre-treatment of cells with MW01 led to the abolishment of the IKKγ mono-ubiquitination (FIG. 11 C).

In conclusion, the pre-treatment of cells with MW01 inhibited the formation of essential IKKγ post-translational modifications that are required for DNA damage-induced NF-κB activation.

Structure-Activity-Relationship Analyses of MW01

Different derivatives of MW01 were obtained (FIG. 12 A) and tested for their ability to inhibit genotoxic stress-induced phosphorylation of p65 at S536. Densitometry of western blot bands was used to quantify signal intensities of the p65 S536 phosphorylation and total p65 amount. The signal intensities of the p65 S536 phosphorylation were normalised to the signal intensities of total p65 and the quotients were normalised to DMSO/etoposide and compared with MW01/etoposide co-treated samples (FIG. 13). The MW01 derivatives MW01C2, MW01C3, and MW01C4 showed lowest p-p65/p65 ratios as a consequence of strongly inhibited NF-κB activation following etoposide co-treatment. Compared to MW01, these compounds are derivatives in which the hydroxyl group was exchanged with a small substitute either fluoride, chloride or a methyl group, respectively. Furthermore, MW01C3 and MW01C4 differed in the substitution of the aromatic ring system V (FIG. 12 B) regarding the two methoxy groups that are missing. The methoxy groups did not seem to be essential for the inhibitory function of the derivatives, but potentially may have an impact on their solubility.

In comparison to the exchange of the hydroxyl group, also the presence of a methoxy group at the vicinal carbon atom in ring system I in MW01C1 resulted in a highly potent derivative.

Hence, by analysing structure-activity-relationships the hydroxyl group of MW01 was identified as the position suitable for structural or covalent modifications that could maintain the inhibitory function. Furthermore, the hydroxyl group is suitable for different reactions such as nucleophilic substitution.

In Contrast to MW01, PARP1 Inhibitors Block NF-κB Activation after Genotoxic Stress in a Cell Type Dependent Manner.

Damage to DNA is a major threat to survival of cells and induces the DNA damage response that regulates cell fate. It has been shown in literature that the DNA damage-sensing protein PARP1 has multiple functions in the DDR. It is important for the accomplishment of single strand break repair, regulation of transcription and participation in NF-κB mediated pro-survival signaling (Gibson and Kraus; 2012). Stilmann et al. (2009) described by loss-of-function studies that the genotoxic stress-activated NF-κB pathway is dependent on PARP1-dependent PAR chain formation as a scaffold for signalosome component recruitment. Consequently, the application of PARP1 inhibitors inhibited the signaling cascade. In that study the authors used the pharmacological PARP1 inhibitors 3-AB and EB-47. The treatment of HepG2 cells with 3-AB inhibited PAR chain formation and NF-κB DNA binding activity after γ-irradiation. In addition, the study showed that MEF cells treated with 3-AB or EB-47 have abrogated PAR chain formation and NF-κB binding activity after etoposide administration (Stilmann et al.; 2009).

In order to compare MW01 with PARP inhibitors, it was tested, whether inhibition of PARP1 by the clinically approved drug olaparib would inhibit signalosome formation and consequently inhibit the phosphorylation of p65. U2OS cells were pre-treated with increasing concentrations of olaparib ranging from 0.63 µM to 10.0 µM. Then, cells were co-treated with etoposide, harvested 90 min after etoposide application, and were analysed for their phosphorylation state of p65 at S536. No significant decrease in p65 S536 phosphorylation could be detected in comparison to the DMSO/etoposide co-treated controls (FIG. 14 A). Olaparib-mediated inhibition of PAR chain formation was ensured by a control experiment (FIG. 14 B). Therein, cells were pre-treated with DMSO, 3 µM olaparib or 10 µM of the ATM inhibitor Ku55933. Cells were harvested 45 min after application of etoposide and tested for PAR chain formation. The type of experiment as shown in FIG. 14 A was repeated in two independent biological replicates. The signal intensities of S536 phosphorylated p65 and total p65 of all three experiments were quantified by densitometry. The results are displayed as the signal intensity ratio in FIG. 14 C. Comparison of the olaparib/etoposide co-treated samples to the DMSO/etoposide co-treated samples showed that olaparib treatment, despite the inhibition of PAR chain formation, did not influence p65 S536 phosphorylation in U2OS cells.

In order to investigate the influence of PARP1 inhibition by olaparib on general NF-κB activation, qRT-PCR analyses of NF-κB target genes were done.

The relative normalised mRNA levels of NFKBIA (encodes IκBα), TNFAIP3 (encodes A20) and CXCL8 (encodes IL-8) were strongly increased in the irradiated DMSO samples compared to all samples, which were not irradiated. Pre-treatment of cells with olaparib did not change the target gene expression after irradiation compared to the DMSO control sample. In contrast, pre-treatment of cells with either MW01 or the ATM inhibitor KU55933 led to the complete inhibition of NFKBIA, TNFAIP3, and CXCL8 mRNA induction upon irradiation (FIG. 14 D).

Next, it was investigated, if p65 was phosphorylated despite the inhibition of PARP1 by olaparib in HepG2 cells (FIG. 14 E). Expectedly, the pre-treatment of HepG2 cells with the PARP inhibitors olaparib, 3-AB and EB-47 abolished the PAR chain formation 15 min after irradiation, which was detected in the DMSO/IR treated sample as shown in FIG. 14 D. Inhibition of PAR chain formation led to decreased phosphorylation of p65 at S536 in the olaparib and in the 3-AB treated sample 90 min after irradiation. Interestingly, p-p65 S536 phosphorylation was detected in the EB-47 treated sample despite the inhibition of PAR chain formation.

The results shown in FIG. 14 indicate a cell type specific impact of olaparib- and EB-47-mediated PARP1 inhibition on the phosphorylation of p65 at S536. In line with this, inhibition of PARP1-dependent PAR chain formation by 3-AB did not abolish NF-κB DNA binding activity in HEK293 (data not shown, personal communication with Dr. Michael Stilmann).

Collectively, in contrast to MW01, inhibition of PARP1-dependent PAR chain formation by PARP inhibitors (3-AB, EB-47, and olaparib) inhibit p65 activation after genotoxic stress in a cell type dependent manner.

Radio-Sensitisation of Cells by MW01 Mediated Inhibition of DNA Damage-Induced NF-κB Cellular apoptosis is a fine tuned mechanism depending on the processing of anti- and pro-apoptotic signals and the anti-apoptotic functions of NF-κB have already been described in literature (Kucharczak et al.; 2003). In order to show that the inhibition of NF-κB by MW01 led to the upregulation of apoptotic signaling, induction of expression of anti-apoptotic gene products was analysed by quantitative real-time PCR. The pre-treatment of U2OS cells with MW01 did not significantly change the mRNA expression of the genes BIRC3 (encodes cIAP2), XIAP or BCL2L1 (encodes BCL-$X_L$) in comparison to the DMSO control. The γ-IR of cells led to a nearly two-fold induction of BIRC3 mRNA in the irradiated control, but BIRC3 mRNA was down-regulated in MW01 pre-treated cells. Like BIRC3 mRNA, the mRNA of XIAP and BCL2L1 was induced by irradiation. The pre-treatment of cells with MW01 moderately inhibited the expression of XIAP and fully inhibited the expression of BCL2L1. The strongest effect on anti-apoptotic gene regulation was detected on TNFAIP3 (encodes A20), as shown in above FIG. 14D. Pre-treatment of cells with MW01 led to abolished mRNA expression of TNFAIP3 after γ-IR in comparison to the irradiated controls.

Next, the mRNA expression of the pro-apoptotic genes BBC3 (encodes PUMA) and PMAIP1 (encodes NOXA) was analysed. BBC3 mRNA expression was not influenced by pre-treatment of cells with MW01. After irradiation of cells the BBC3 mRNA expression was induced 4-fold in the positive control. The pre-treatment with MW01 only led to a slightly reduced expression, which was still 3-fold induced (FIG. 15 B).

The mRNA expression of PMAIP1 was already increased by pre-treatment with MW01. In the MW01 pre-treated sample PMAIP1 mRNA expression was further elevated after irradiation, but was not changed in the irradiated samples (FIG. 15 B).

In order to analyse the influence of MW01 on apoptotic cell death after genotoxic stress in more detail, apoptotic marker were examined. One of these markers is the caspase-3-dependent cleavage of PARP1. The pre-incubation of U2OS cells with MW01 led to a slight increase of PARP1 cleavage in resting cells. After irradiation of cells a marginal increase of PARP1 cleavage was detected in the irradiated control sample. In contrast, MW01 pre-incubation strongly increased the cleavage of PARP1 (FIG. 16 A).

Using crystal violet staining it was analysed, if the pre-treatment with the compounds of cells prior to γ-irradiation exerted an influence on the cell number. The pre-treatment of cells with MW01 already reduced the cell number in comparison to the DMSO treated samples. After irradiation of cells the pre-treatment with MW01 had a significant effect on further reduction in cell number compared to the DMSO/IR control (FIG. 16 B).

To test whether the reduction in cell number was caused by reduced proliferation, the percentage of viable cells after compound treatment and irradiation was measured by exclusion of annexin V and/or propidium-iodide staining positive cells. Similar to the result of the crystal violet staining MW01 pre-treatment exerted an effect on non-irradiated cells. The percentage of viable cells was slightly reduced compared to the DMSO control. However, after irradiation around 14% less viable cells were measured in the DMSO sample and 17% less viable cells were measured in the MW01 sample (FIG. 16 C).

The sensitising effect of MW01 on cells was tested in MEF cells with a low irradiation dose of 2 Gy, an amount cells are able to repair. Cells were pre-treated with MW01, irradiated and cells were analysed by annexin V staining 24 or 48 h after irradiation. After 24 h, the treatment of cells with MW01 led to an increase of annexin V positive cells of about 10%. This is in line with the results displayed in FIG. 15, indicating increased apoptotic signaling in cells treated with MW01 even without IR. Annexin V staining of cells was further increased after 2 Gy of γ-irradiation in MW01 treated samples (circa 34%), but was only marginally increased in the DMSO control. Comparing the annexin V positive cells of MW01 treated and MW01/γ-IR co-treated samples, a sensitising effect for low γ-irradiation dose-induced apoptosis of about 12% was found (FIG. 16 D).

In addition, the sensitising effect of NF-κB inhibition was tested in HT1080 cells. After pre-treatment with DMSO or MW01, cells were irradiated with a dose of 10 Gy and analysed by annexin V staining. The co-treatment of cells with MW01 led to a significant increase in annexin V staining compared to the irradiated control. The population of early apoptotic cells was roughly doubled (FIG. 16 E).

Considering the results of this section, co-treatment of cells with MW01 in combination with the induction of DNA DSBs led to an increase in the percentage of apoptotic cells compared to single treatments.

MW01 Inhibits DNA Repair Mechanisms that are NF-κB Independent

U2OS cells were grown on coverslips and incubated 30 min with DMSO or MW01 (5 μM). Then, cells were γ-irradiated (5 Gy) or mock irradiated (mock IR). After 5 hours, cells were fixed and subjected to immunofluorescence staining procedure. DNA damage-indicating γH2AX foci and nuclei (n≥480 nuclei per condition) were counted for the calculation of average foci per nucleus. Significance was calculated using student's t-test.

Treatment of cells with MW01 led to a significant increase in γH2AX foci per cell in untreated (non-irradiated) cells, indicating that MW01 inhibited, in addition to the genotoxic stress-induced IKK/NF-κB signaling pathway, other DNA repair mechanisms occurring in steady state.

Examples of Chemical Compounds of the Invention:

When in the final step of the synthesis of a compound an acid such as trifluoroacetic acid or acetic acid was used, for example when trifluoroacetic acid was employed to an acid-labile protecting group (e.g. a t-Bu group) or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Likewise starting materials or intermediates bearing a basic center like for example a basic nitrogen were either obtained and used as free base or in salt form like, for example, a trifluoroacetic acid salt, a hydro bromic acid salt, sulfuric acid salt, or a hydrochloric acid salt.

Abbreviations Used

Acetonitrile ACN
Aqueous Aq.
tert-Butyl t-Bu dibenzylidenacetone dba
Dichloromethane DCM
4-Dimethyaminopyridine DMAP
N,N-Dimethylformamide DMF
Dimethylsulfoxide DMSO
Ethanol EtOH
Ethyl acetate EtOAc
Formic Acid FA
High performance liquid chromatography HPLC
Methanol MeOH
N-Methyl-2-pyrrolidone NMP
Room temperature 20° C. to 25° C. RT
Saturated sat.
Triethanolamine TEA
Tetrahydrofuran THF
Trifluoroacetic acid TFA LCMS (method 1): Instrument: Agilent Technologies 6220 Accurate Mass TOF LC/MS linked to Agilent Technologies HPLC 1200 Series; Column: Thermo Accuore RP-MS; Particle Size: 2.6 µM Dimension: 30×2.1 mm; Eluent A: $H_2O$ with 0.1% FA Eluent B: ACN with 0.1% FA; Gradient: 0.00 min 95% A, 0.2 min 95% A, 1.1 min 1% A, 2.5 min Stop time, 1.3 min Post time; Flow rate: 0.8 ml/min; UV-detection: 220 nm, 254 nm, 300 nm.

LCMS (method 2): Instrument: Agilent Technologies 6120 Quadrupole LC/MS linked to Agilent Technologies HPLC 1290 Infinity; Column: Thermo Accuore RP-MS; Particle Size: 2.6 µM Dimension: 30×2.1 mm; Eluent A: $H_2O$ with 0.1% FA Eluent B: ACN with 0.1% FA; Gradient: 0.00 min 95% A, 0.2 min 95% A, 1.1 min 1% A, 2.5 min Stop time, 1.3 min Post time; Flow rate: 0.8 ml/min; UV-detection: 220 nm, 254 nm, 300 nm.

Preparative HPLC (method 1): Instrument: Waters preparative HPLC-System composed of: binary gradient module 2545, UV detector 2489, waters prep inject, and waters fraction collector III; Column: Macherey-Nagel VP 250/21 Nucleodor 100-7 C18ec; Eluent A: $H_2O$ with 0.1% TFA Eluent B: ACN with 0.1% TFA; Gradient: 0.00 min 85% A, 2.00 min 85% A, 22.00 min 15% A, 25.00 min 15% A, 26.00 min 0% A, 28.00 min 0% A, 29.00 min, 85% A 30.00 min 85% A, 30.10 min stop; Flow rate: 30 ml/min; UV-detection: 254 nm.

Preparative HPLC (method 2): Instrument: Waters preparative HPLC-System composed of: binary gradient module 2545, UV detector 2489, waters prep inject, and waters fraction collector III; Column: Macherey-Nagel VP 250/21 Nucleodor 100-7 C18ec; Eluent A: $H_2O$ with 0.1% TFA Eluent B: ACN with 0.1% TFA; Gradient: 0.00 min 70% A, 2.00 min 70% A, 22.00 min 10% A, 25.00 min 10% A, 26.00 min 0% A, 28.00 min 0% A, 29.00 min, 70% A 30.00 min 70% A, 30.10 min stop; Flow rate: 30 ml/min; UV-detection: 254 nm.

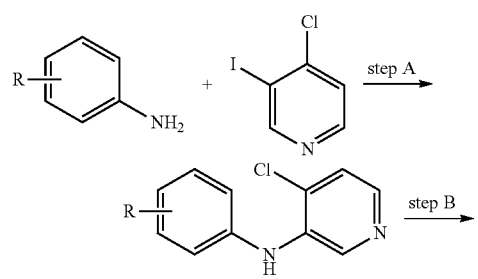

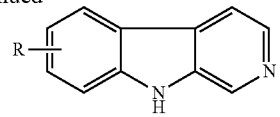

The synthesis of β-carbolines (e.g. 6-methoxy-9H-pyrido[3,4-b]indole) were performed as described by Laha et al. (Laha, J. K., et al. J. Org. Chem. (2011) 76, 6421-6425).

General Reaction to the 9-benzyl-9H-pyrido[3,4-b]indole Derivatives

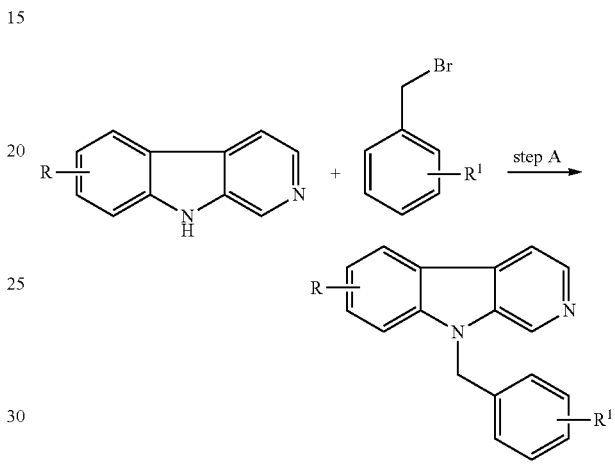

Example 1: 9-(2-Chlorobenzyl)-6-methoxy-9H-pyrido[3,4-b]indole

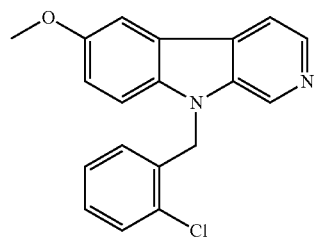 [SMILES: COc1ccc2c(c1)c1ccncc1n2Cc1ccccc1Cl]

To a solution of 27.6 mg 6-methoxy-9H-pyrido[3,4-b]indole (0.14 mmol, 1.0 eq.) in 1 ml DMF, 8.91 mg of sodium hydride (0.22 mmol, 1.6 eq.) were added under nitrogen. The mixture was stirred for 20 minutes at RT and a solution of 34.3 mg (0.17 mmol, 1.2 eq.) 2-chlorobenzyl bromide, and 1.7 mg DMAP (0.01 mmol, 0.1 eq.) in 1 ml DMF was added dropwise. After complete addition the reaction mixture was stirred for 3 h at 70° C. Upon completion of the reaction the mixture was diluted with water and sat. solution of $NaHCO_3$ was added. The water phase was extracted with DCM three times. The combined organic phases were dried over magnesium sulfate and the solvent was evaporated under reduced pressure. The crude product was purified by silica gel chromatography using a gradient of DCM/MeOH as eluent. The fractions containing the product were evaporated under reduced pressure to yield the title compound as a solid.

Yield: 25.9 mg MS (ES+) [M+H]: m/e=323

Example 2: 9-(2-Chlorobenzyl)-7-methoxy-1-methyl-9H-pyrido[3,4-b]indole

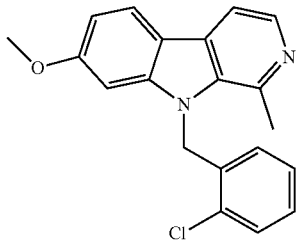 [SMILES: COc1ccc2c3ccnc(C)c3n(Cc3ccccc3Cl)c2c1]

The title compound was prepared by adapting the procedure described in example 1 with the difference that harmine was used instead of 6-methoxy-9H-pyrido[3,4-b]indole.

Yield: 19.3 mg MS(ES+) [M+H]: m/e=337

Example 3: 3-Methoxy-4-((6-methoxy-9H-pyrido[3,4-b]indol-9-yl)methyl)benzoic Acid

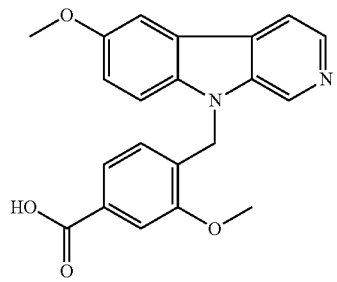

The title compound was prepared by adapting the procedure described in example 1 with the difference that Methyl 4-(bromomethyl)-3-methoxybenzoate was used instead of 2-chlorobenzyl bromide.

Yield: 12.2 mg MS(ES+) [M+H]: m/e=363

Example 4: 9-Benzyl-6-methoxy-9H-pyrido[3,4-b]indole

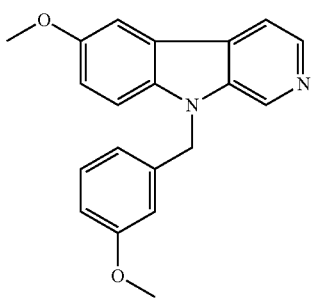 [SMILES: COc1cccc(Cn2c3ccc(OC)cc3c3ccncc32)c1]

The title compound was prepared by adapting the procedure described in example 1 with the difference that 3-methoxybenzyl bromide was used instead of 2-chlorobenzyl bromide.

Yield: 22.4 mg MS(ES+) [M+H]: m/e=319

Example 5: 9-Benzyl-6-methoxy-9H-pyrido[3,4-b]indole

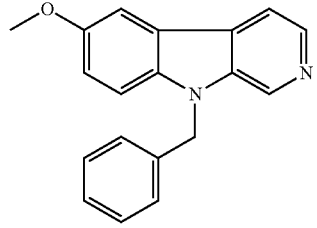 [SMILES: COc1ccc2c(c1)c1ccncc1n2Cc1ccccc1]

The title compound was prepared by adapting the procedure described in example 1 with the difference that benzyl bromide was used instead of 2-chlorobenzyl bromide.

Yield: 16.7 mg MS(ES+) [M+H]: m/e=289

Example 6: 9-(3,4-Dichlorobenzyl)-6-methoxy-9H-pyrido[3,4-b]indole

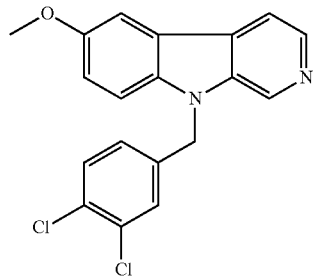

The title compound was prepared by adapting the procedure described in example 1 with the difference that 3,4-dichlorobenzyl bromide was used instead of 2-chlorobenzyl bromide.

Yield: 19 mg MS(ES+) [M+H]: m/e=357/359 dichloro pattern

Example 7: 9-((6-Bromobenzo[d][1,3]dioxol-5-yl)methyl)-6-methoxy-9H-pyrido[3,4-b]indole

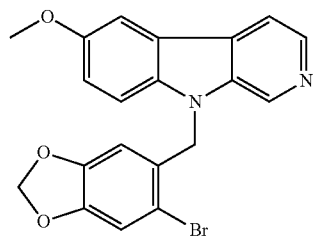 [SMILES: COc1ccc2c(c1)c1ccncc1n2Cc1cc2c(cc1Br)OCO2]

The title compound was prepared by adapting the procedure described in example 1 with the difference that 5-bromo-6-bromomethyl-1,3-benzodioxole was used instead of 2-chlorobenzyl bromide.

Yield: 11.4 mg MS(ES+) [M+H]: m/e=411/413 bromo pattern

Example 8: 9-(2-Bromo-5-methoxybenzyl)-6-methoxy-9H-pyrido[3,4-b]indole

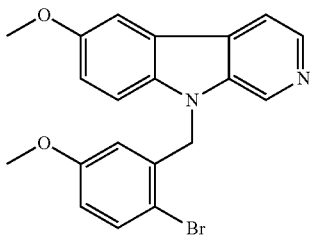 [SMILES: COc1ccc(Br)c(Cn2c3ccc(OC)cc3c3ccncc32)c1]

The title compound was prepared by adapting the procedure described in example 1 with the difference that 2-Bromo-5-methoxybenzyl bromide was used instead of 2-chlorobenzyl bromide.

Yield: 3.5 mg MS(ES+) [M+H]: m/e=397/399 bromo pattern

General Reaction to the 9-(2-aroyl)-carbazole Derivatives

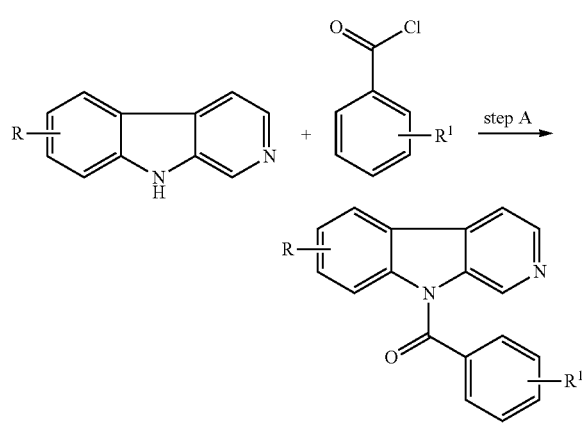

Example 9: 9-(2-benzoyl)-carbazole. (D08) (CAS: 19264-68-7)

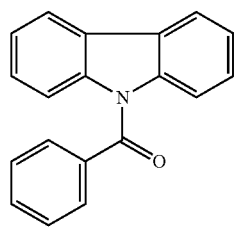 [SMILES: O=C(c1ccccc1)n1c2ccccc2c2ccccc21]

The title compound was prepared by adding to a cooled (0° C.) solution of 100 mg carbazole (0.60 mmol, 1.0 eq.) in 5 ml toluene/DMF (1:1), 23.9 mg sodium hydride (0.60 mmol, 1.0 eq.) under nitrogen. After stirring at 0° C. for 30 minutes a solution of 69.4 µl benzoyl chloride (0.60 mmol, 1.0 eq.) in 200 µl toluene was added dropwise. The reaction mixture was stirred for 17 hours at RT and the precipitated solid was filtered and washed with EtOAC. The filtrate was evaporated under reduced pressure. The crude product was purified by silica gel chromatography using a gradient of cyclohexane/EtOAc as eluent. The fractions containing the product were evaporated under reduced pressure to yield the title compound as a solid.

Yield: 107 mg MS(ES+) [M+H]: m/e=272

Example 10: (6-Methoxy-9H-pyrido[3,4-b]indol-9-yl)(phenyl)methanone

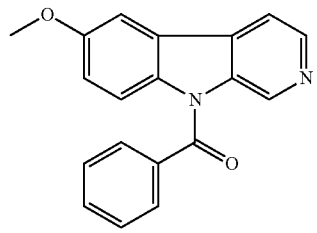 [SMILES: COc1ccc2c(c1)c1ccncc1n2C(=O)c1ccccc1]

The title compound was prepared by adding 10 mg 6-methoxy-9H-pyrido[3,4-b]indole (0.05 mmol, 1.0 eq.) in 5 ml toluene/DMF (1:1), 2.02 mg sodium hydride (0.05 mmol, 1.0 eq.) to a cooled (0° C.) solution under nitrogen. After stirring at 0° C. for 30 minutes a solution of 5.9 µl benzoyl chloride (0.05 mmol, 1.0 eq.) in 17 µl toluene was added dropwise. The reaction mixture was stirred for 2 hours at RT and then the solvent was evaporated under reduced pressure. The crude product was purified by silica gel chromatography using a gradient of DCM/MeOH as eluent. The fractions containing the product were evaporated under reduced pressure to yield the title compound. This product was then again purified via preparative HPLC method 1. The fractions containing the product were evaporated and lyophilized to yield a solid. The product was obtained as its trifluoroacetate salt.

Yield: 8.1 mg MS(ES+) [M+H]: m/e=303

Example 11: (6-Methoxy-9H-pyrido[3,4-b]indol-9-yl)(4-methoxyphenyl)methanone

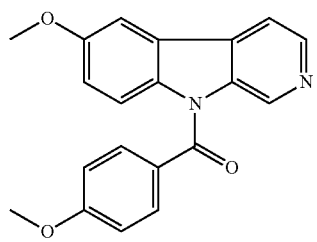 [SMILES: COc1ccc(C(=O)n2c3ccc(OC)cc3c3ccncc32)cc1]

The title compound was prepared by adding to a suspension of 20 mg 6-methoxy-9H-pyrido[3,4-b]indole (0.10 mmol; 1.00 eq.) in 2.0 ml ACN, sequentially 41 µl 4-methoxybenzoyl chloride (0.30 mmol; 3.00 eq.), 37.0 mg DMAP (0.30 mmol; 3.00 eq.), and 42 µl TEA (0.30 mmol; 3.00 eq.). The mixture was stirred for 1 hour at RT. Then, the reaction mixture was diluted with 1 ml water, filtered and purified by preparative HPLC method 1. The fractions containing the product were evaporated and lyophilized to yield a solid. The product was obtained as its trifluoroacetate salt.

Yield: 19.2 mg MS(ES+) [M+H]: m/e=333

Example 12: Benzo[d][1,3]dioxol-5-yl(6-methoxy-9H-pyrido[3,4-b]indol-9-yl)methanone

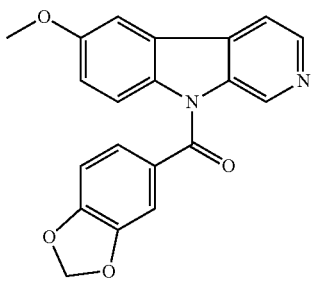 [SMILES: COc1ccc2c(c1)c1ccncc1n2C(=O)c1ccc2c(c1)OCO2]

The title compound was prepared by adapting the procedure described in example 11 with the difference that piperonyloyl chloride was used instead of 4-methoxybenzoyl chloride.

Yield: 41.5 mg MS(ES+) [M+H]: m/e=347

Example 13: (2-Bromo-5-methoxyphenyl)(6-methoxy-9H-pyrido[3,4-b]indol-9-yl)methanone

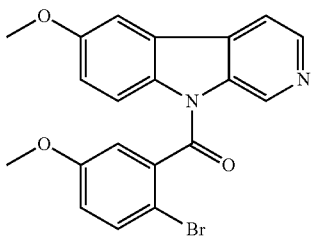 [SMILES: COc1ccc(Br)c(C(=O)n2c3ccc(OC)cc3c3ccncc32)c1]

The title compound was prepared by adapting the procedure described in example 11 with the difference that 2-bromo-5-methoxy benzoyl chloride was used instead of 4-methoxybenzoyl chloride.

Yield: 25.2 mg MS(ES+) [M+H]: m/e=411/413 (bromo pattern)

Example 14: (2-Chloropyridin-3-yl)(6-methoxy-9H-pyrido[3,4-b]indol-9-yl)methanone

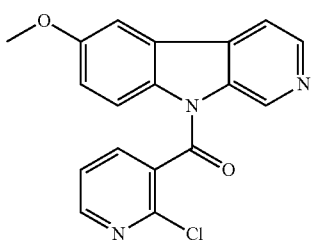 [SMILES: COc1ccc2c(c1)c1ccncc1n2C(=O)c1cccnc1Cl]

The title compound was prepared by adapting the procedure described in example 11 with the difference that 2-chloronicotinoyl chloride was used instead of 4-methoxybenzoyl chloride.

Yield: 5.4 mg MS(ES+) [M+H]: m/e=338

Example 15: (6-Methoxy-9H-pyrido[3,4-b]indol-9-yl)(naphthalen-1-yl)methanone

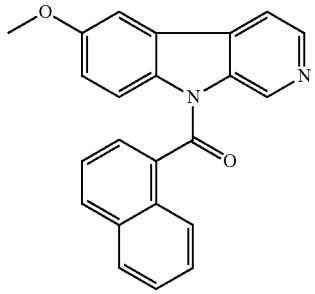 [SMILES: COc1ccc2c(c1)c1ccncc1n2C(=O)c1cccc2ccccc12]

The title compound was prepared by adapting the procedure described in example 11 with the difference that 1-naphtoyl chloride was used instead of 4-methoxybenzoyl chloride.

Yield: 17.3 mg MS(ES+) [M+H]: m/e=353

Example 16: 8H-Benzo[c]indolo[3,2,1-ij][1,5]naphthyridin-8-one (CAS 38478-71-6)

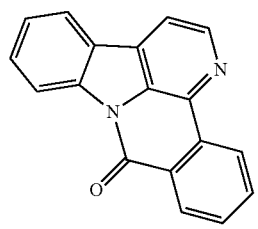 [SMILES: O=c1c2ccccc2c2nccc3c4ccccc4n1c32]

The title compound was prepared by dissolving 86 mg 9H-pyrido[3,4-b]indol-1-yl trifluoromethanesulfonate (0.272 mmol, 1-00 eq.), 68.5 mg 2-methoxycarbonylphenyl boronic acid (0.381 mmol, 1.40 eq.), 12.5 mg $Pd_2(dba)_3$ (0.014 mmol; 0.05 eq.), 7.1 mg triphenylphosphine (0.027 mmol; 0.10 eq.) in 2.7 ml toluene and 1.8 ml EtOH. The solution was purged with nitrogen for 5 minutes. To the reaction mixture was added 0.9 ml sat. Aq. $Na_2CO_3$ solution and the mixture was purged for 5 minutes with nitrogen. Then, the solution was stirred at 80° C. for 90 minutes.

The solution was diluted with EtOAc and washed two times with water, dried over magnesium sulfate and the solvent was evaporated under reduced pressure. The crude product was purified by silica gel chromatography using a gradient of DCM/MeOH as eluent. The fractions containing the product were evaporated under reduced pressure to yield the title compound as a solid.

Yield: 30 mg MS(ES+) [M+H]: m/e=271

Example 17: 5,6,11,12-Tetramethoxy-8H-benzo[c]indolo[3,2,1-ij][1,5]naphthyridin-8-one

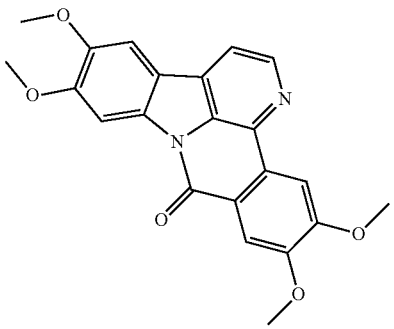

The title compound was prepared by dissolving 80 mg 6,7-dimethoxy-9H-pyrido[3,4-b]indol-1-yl trifluoromethanesulfonate (0.202 mmol; 1.00 eq.), 67.9 mg 4,5-dimethoxy-2-(methoxycarbonyl)benzeneboronic acid (0.283 mmol; 1.40 eq.), 9.2 mg $Pd_2(dba)_3$ (0.010 mmol; 0.05 eq.), 5.3 mg triphenylphosphine (0.020 mmol; 0.10 eq.) in 2.3 ml toluene and 1.8 ml EtOH. The solution was purged with nitrogen for 5 minutes. To the reaction mixture was added 0.6 ml saturated aqueous sodium carbonate solution and the mixture was purged again for 5 minutes with nitrogen. Then, the solution was stirred at 80° C. for 17 hours. The solution was diluted with ethyl acetate and washed two times by water, dried over magnesium sulfate and the solvent was evaporated under reduced pressure. The crude product was purified by silica gel chromatography using a gradient of DCM/MeOH as eluent. The fractions containing the product were evaporated under reduced pressure to yield the title compound. This product was then further purified via preparative HPLC method 2. The fractions containing the product were evaporated and lyophilized to yield a white solid. The product was obtained as its trifluoroacetate salt.

Yield: 0.4 mg MS(ES+) [M+H]: m/e=391

General Reaction to the methylpyrazolo[3,4-b]indole Derivatives

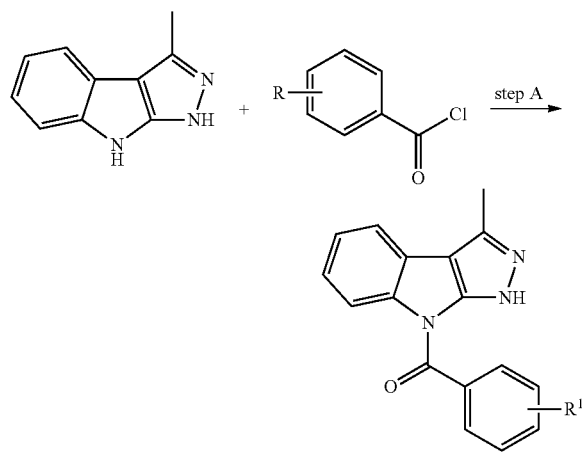

3-Methylpyrazolo[3,4-b]indoles were synthesized according to a literature procedure (Monge, A., et al. *Eur. J. Med. Chem.* (1991) 26, 179-188).

Example 18: (3-Bromophenyl)(3-methylpyrazolo[3,4-b]indol-8(1H)-yl)methanone

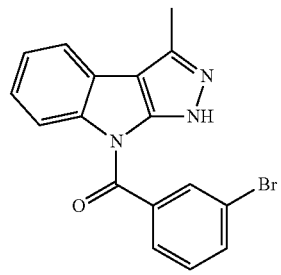 [SMILES: Cc1n[nH]c2c1c1ccccc1n2C(=O)c1cccc(Br)c1]

The title compound was prepared by adding to a suspension of 25 mg 3-methylpyrazolo[3,4-b]indole (0.146 mmol; 1.00 eq.) in 2.9 ml ACN, sequentially 57.7 µl 3-bromobenzoyl chloride (0.438 mmol; 3.00 eq.), 53.5 mg 4-diemthylaminopyridine (DMAP) (0.438 mmol; 3.00 eq.), and 60.7 µl TEA (0.438 mmol; 3.00 eq.). The mixture was stirred for at least 3 hours at RT. After complete reaction the reaction mixture was diluted with 1 ml water, filtered and purified by preparative HPLC method 1. The fractions containing the product were evaporated and lyophilized to yield a solid. The product was obtained as its trifluoroacetate salt.

Yield: 2.5 mg MS(ES+) [M+H]: m/e=354/356 bromo pattern

Example 19: (4-Methoxyphenyl)(3-methylpyrazolo[3,4-b]indol-8(1H)-yl)methanone The title compound was prepared by adapting the procedure described in example 18 with the difference that 4-methoxybenzoyl chloride was used instead of 3-bromobenzoyl chloride and that the scale of the reaction was performed for 100 mg 3-methylpyrazolo[3,4-b]indole (0.584 mmol; 1.00 eq.).

Yield: 94.6 mg MS(ES+) [M+H]: m/e=323

Example 20: (3-Methylpyrazolo[3,4-b]indol-8(1H)-yl)(phenyl)methanone

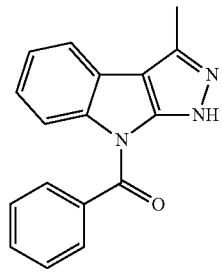 [SMILES: Cc1n[nH]c2c1c1ccccc1n2C(=O)c1ccccc1]

The title compound was prepared by adapting the procedure described in example 18 with the difference that benzoyl chloride was used instead of 3-bromobenzoyl chloride.

Yield: 5.5 mg MS(ES+) [M+H]: m/e=276

Example 21: (3-Methylpyrazolo[3,4-b]indole-1,8-diyl)bis(phenylmethanone)

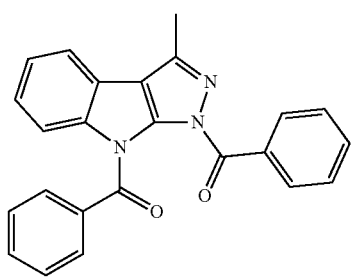 [SMILES: Cc1nn(C(=O)c2ccccc2)c2c1c1ccccc1n2C(=O)c1ccccc1]

The title compound was obtained as a side product from the synthesis of example 20.

Yield: 7.8 mg MS(ES+) [M+H]: m/e=380

Example 22: (2-Chloropyridin-3-yl)(3-methylpyrazolo[3,4-b]indol-8(1H)-yl)methanone

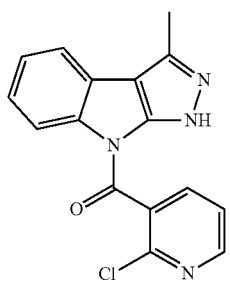 [SMILES: Cc1n[nH]c2c1c1ccccc1n2C(=O)c1cccnc1Cl]

The title compound was prepared by adapting the procedure described in example 18 with the difference that 2-chloronicotinoyl chloride was used instead of 3-bromobenzoyl chloride.

Yield: 12.1 mg MS(ES+) [M+H]: m/e=311/313 chloro pattern

Example 23: (2-Bromo-6-chlorophenyl)(3-methylpyrazolo[3,4-b]indol-8(1H)-yl)methanone

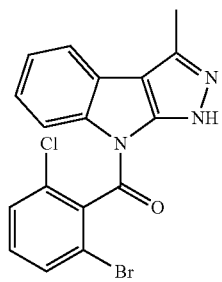 [SMILES: Cc1n[nH]c2c1c1ccccc1n2C(=O)c1c(Cl)cccc1Br]

The title compound was prepared by adapting the procedure described in example 18 with the difference that 2-bromo-6-chlorobenzoyl chloride was used instead of 3-bromobenzoyl chloride.

Yield: 8.7 mg MS(ES+) [M+H]: m/e=388/390 isotope pattern

Example 24: 5-(Pyridin-3-yl)phenanthridin-6(5H)-one

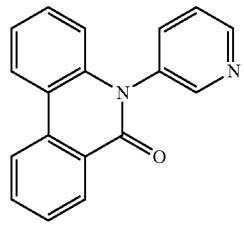

The title compound was prepared by adding 150 mg 6(5H)-Phenanthridinone (0.77 mmol; 1.00 eq.), 111 µl 3-Bromopyridin (1.15 mmol; 1.50 eq.), 106 mg potassium carbonate (0.77 mmol; 1.00 eq.), 2.7 mg copper(I)iodide (0.04 mmol; 0.05 eq.) to a flask. To the solids 900 µl NMP (7.7 mmol; 10.0 eq.) were added. The mixture was heated to 180° C. and the reaction stopped at a conversion ratio, starting material to product 1:1. Then, the reaction mixture was diluted with diethyl ether and extracted with water. The water phase was washed with diethyl ether three times. The combined organic phases were washed with water one time, dried over magnesium sulfate, and the solvent was evaporated under reduced pressure. While evaporating the solvents under reduced pressure starting material precipitated as a white solid and was filtered off. The filtrate was evaporated to dryness. The crude product was purified by silica gel chromatography using a gradient of cyclohexane/EtOAc as eluent. The fractions containing the product were evaporated under reduced pressure to yield the title compound.

Yield: 62 mg MS(ES+) [M+H]: m/e=273

General Reaction to the β-carbolinone Derivatives

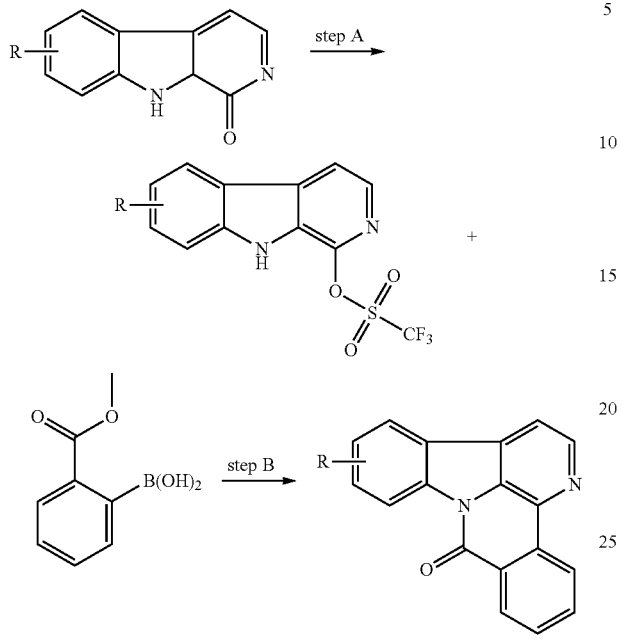

The β-carbolinone derivate (e.g. 6-methoxy-2,9-dihydro-1H-pyrido[3,4-b]indol-1-one) were synthesized as described in literature (La Regina, G., et al. Synthesis (2014), 46, 2093-2097)

Example 25: 12-methoxy-8H-benzo[c]indolo[3,2,1-ij][1,5]naphthyridin-8-one

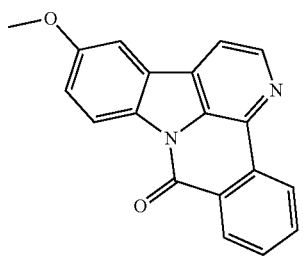 [SMILES: COc1ccc2c(c1)c1ccnc3c4ccccc4c(=O)n2c13]

The title compound was prepared by dissolving 78.9 mg 6-methoxy-2,9-dihydro-1H-pyrido[3,4-b]indol-1-one (0.368 mmol, 1.0 eq.) in 3.8 ml pyridine. The solution was cooled down to 4° C. and purged with nitrogen. To this solution 439 µl triflic anhydride (0.737 mmol, 2.0 eq.) was added dropwise (≈30 min). The mixture was stirred for 45 minutes at RT.

After complete reaction the mixture was purred into water and the water phase was extracted with EtOAc three times. The combined organic phases were dried over magnesium sulfate and the solvent was evaporated under reduced pressure. The crude product (6-methoxy-9H-pyrido[3,4-b]indol-1-yl trifluoromethanesulfonate) was used in the next step without further purification.

73 mg 6-methoxy-9H-pyrido[3,4-b]indol-1-yl trifluoromethanesulfonate (0.179 mmol, 1.0 eq.), 45 mg (2-(methoxycarbonyl)phenyl)boronic acid (0.251 mmol, 1.4 eq.), 8.2 mg Tris(dibenzylideneacetone) dipalladium(0) (0.009 mmol, 0.05 eq.) and 4.7 mg triphenylphosphine (0.018 mmol, 0.1 eq.) were dissolved in 1.8 ml toluene and 1.2 ml ethanol. The solution was purged with nitrogen and 0.6 ml of a saturated aqueous sodium carbonate solution was added. The mixture was stirred for 90 minutes at 80° C. After complete reaction the mixture was diluted with EtOAc and the organic phase was washed two times with water, dried over magnesium sulfate and the solvent was evaporated under reduced pressure. The crude product was purified using silica gel chromatography with DCM/MeOH as solvent and was afterwards further purified by HPLC with ACN/water.

Yield: 18 mg MS (ES+) [M+H]: m/e=301

Example 26: 11-methoxy-8H-benzo[c]indolo[3,2,1-ij][1,5]naphthyridin-8-one

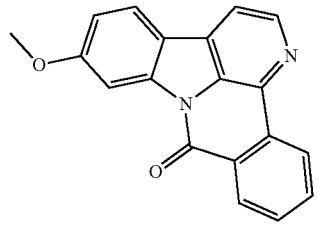 [SMILES: COc1ccc2c3ccnc4c5ccccc5c(=O)n(c2c1)c34]

The title compound was prepared by adapting the procedure described in example 25 with the difference that 7-methoxy-2,9-dihydro-1H-pyrido[3,4-b]indol-1-one was used instead of 6-methoxy-2,9-dihydro-1H-pyrido[3,4-b]indol-1-one.

Yield: 5 mg MS (ES+) [M+H]: m/e=301

Example 27: 11,12-dimethoxy-8H-benzo[c]indolo[3,2,1-ij][1,5]naphthyridin-8-one

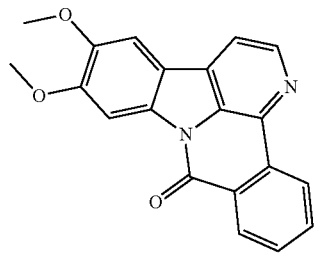 [SMILES: COc1cc2c3ccnc4c5ccccc5c(=O)n(c2cc1OC)c34]

The title compound was prepared by adapting the procedure described in example 25 with the difference that 6,7-dimethoxy-2,9-dihydro-1H-pyrido[3,4-b]indol-1-one was used instead of 6-methoxy-2,9-dihydro-1H-pyrido[3,4-b]indol-1-one.

Yield: 5 mg MS (ES+) [M+H]: m/e=331

General Reaction to the 6-methoxy-2,9-dihydro-1H-pyrido[3,4-b]indol-1-one Derivatives

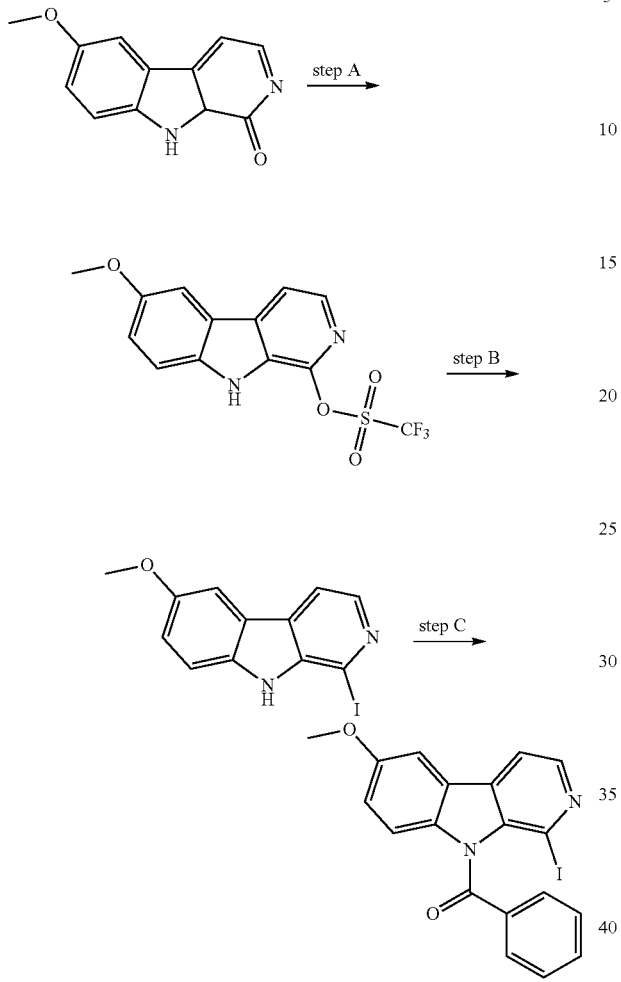

6-methoxy-2,9-dihydro-1H-pyrido[3,4-b]indol-1-one was synthesized as described in literature (La Regina, G., et al. Synthesis (2014), 46, 2093-2097).

Example 28: (1-iodo-6-methoxy-9H-pyrido[3,4-b]indol-9-yl)(phenyl)methanone

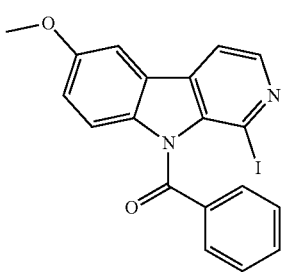 [SMILES: COc1ccc2c(c1)c1ccnc(I)c1n2C(=O)c1ccccc1]

The title compound was prepared by dissolving 78.9 mg 6-methoxy-2,9-dihydro-1H-pyrido[3,4-b]indol-1-one (0.368 mmol, 1.0 eq.) in 3.8 ml pyridine. The solution was cooled down to 4° C. and purged with nitrogen. To this solution 439 µl triflic anhydride (0.737 mmol, 2.0 eq.) was added dropwise 30 min). The mixture was stirred for 45 minutes at RT.

After complete reaction the mixture was purred into water and the water phase was extracted with EtOAc three times. The combined organic phases were dried over magnesium sulfate and the solvent was evaporated under reduced pressure. The crude product (6-methoxy-9H-pyrido[3,4-b]indol-1-yl trifluoromethanesulfonate) was used in the next step without further purification.

100 mg 6-methoxy-9H-pyrido[3,4-b]indol-1-yl trifluoromethanesulfonate (0.289 mmol, 1.0 eq.) and 216 mg sodium iodide (1.44 mmol, 5.0 eq.) were dissolved under nitrogen in 0.7 ml acetonitrile. The solution was cooled down to 0° C. and 50 µl triflic acid (0.578 mmol, 2.0 eq.) were added dropwise 15 min). After complete addition the mixture was stirred at room temperature for 3 h. After complete reaction the mixture was diluted with EtOAc and water and was cooled down to 0° C. The aqueous phase was brought to pH 10 with NaOH (c=10 mol/l, <1 ml), then the phases were separated. The organic phase was washed with sodium thiosulfate solution (w=5%), NaOH solution (c=1 mol/l) and with brine. The organic phase was dried over magnesium sulfate and the solvent was evaporated under reduced pressure. The crude product was purified using silica gel chromatography with cyclohexane/EtOAc/MeOH as solvent to achieve 1-iodo-6-methoxy-9H-pyrido[3,4-b] indole. To a suspension of 20 mg 1-iodo-6-methoxy-9H-pyrido[3,4-b]indole (0.062 mmol, 1.0 eq.) in 1.2 ml ACN, sequentially 21 µl benzoyl chloride (0.19 mmol; 3.0 eq.), 22.6 mg DMAP (0.19 mmol; 3.0 eq.), and 26 µl TEA (0.19 mmol; 3.0 eq.) were added. The mixture was stirred for 72 hours at RT. Afterwards the reaction mixture was diluted with 1 ml water, filtered and purified by preparative HPLC method 1.

Yield: 15 mg MS (ES+) [M+H]: m/e=428

General Reaction to the 6-methoxy-2,9-dihydro-1H-pyrido[3,4-b]indol-1-one Derivatives

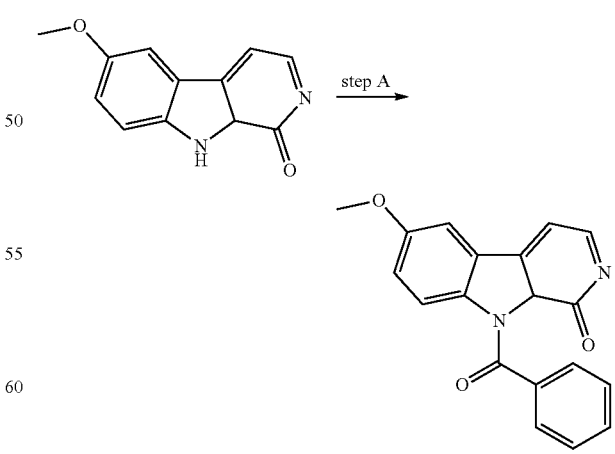

6-methoxy-2,9-dihydro-1H-pyrido[3,4-b]indol-1-one was synthesized as described in literature (La Regina, G., et al. Synthesis (2014), 46, 2093-2097).

Example 29: 9-benzoyl-6-methoxy-2,9-dihydro-1H-pyrido[3,4-b]indol-1-one

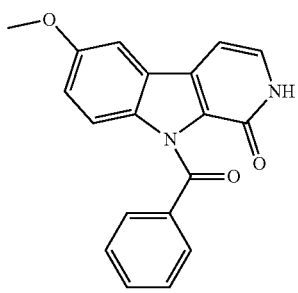 [SMILES: COc1ccc2c(c1)c1cc[nH]c(=O)c1n2C(=O)c1ccccc1]

The title compound was prepared by adding to a suspension of 20 mg methoxy-2,9-dihydro-1H-pyrido[3,4-b]indol-1-one (0.093 mmol, 1.0 eq.) in 1.2 ml ACN, sequentially 33 µl benzoyl chloride (0.28 mmol; 3.0 eq.), 34.2 mg DMAP (0.28 mmol; 3.0 eq.), and 34 µl TEA (0.28 mmol; 3.0 eq.) were added. The mixture was stirred for 72 hours at RT. Afterwards the reaction mixture was diluted with 1 ml water and the precipitated product was filtered off. The filtrate contained product and was dried via lyophilization and purified by preparative HPLC method 1.

Yield: 9 mg MS (ES+) [M+H]: m/e=319

General Reaction to (1-methylpyrazolo[3,4-b]indol-8(1H)-yl)(phenyl)methanone Derivatives

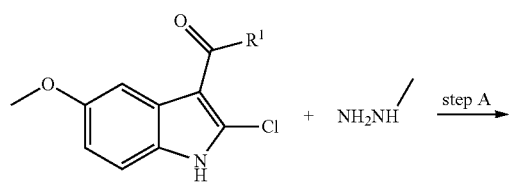

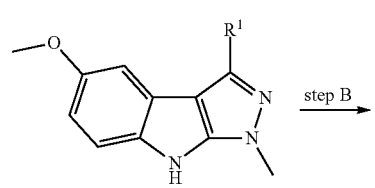

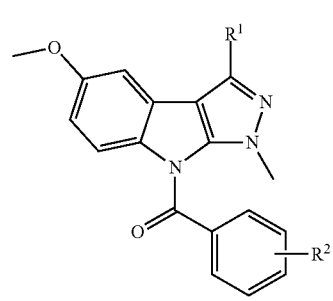

Example 30: (2-bromophenyl)(5-methoxy-1,3-dimethylpyrazolo[3,4-b]indol-8(1H)-yl)methanone

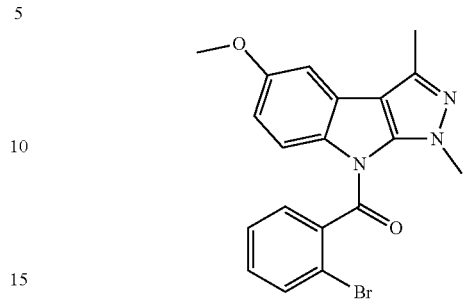

The title compound was prepared by dissolving 100 mg 1-(2-chloro-5-methoxy-1H-indol-3-yl)ethanone (0.45 mmol, 1.0 eq.) and 71 µl monomethyl hydrazine in 1.3 ml ethanol. The solution was kept at reflux for 12 h. After complete reaction the mixture was cooled down and the precipitated product was collected by filtration. The solid compound was washed with ethanol to achieve pure 5-methoxy-1,3-dimethyl-1,8-dihydropyrazolo[3,4-b]indole. To a suspension of 20 mg 5-methoxy-1,3-dimethyl-1,8-dihydropyrazolo[3,4-b]indole (0.093 mmol, 1.0 eq.) in 1.9 ml ACN, sequentially 36 µl 2-bromobenzoyl chloride (0.28 mmol, 3.0 eq.), 34 mg DMAP (0.28 mmol, 3.0 eq.), and 39 µl TEA (0.28 mmol; 3.0 eq.) were added. The mixture was stirred for 6 hours at RT. Afterwards the reaction mixture was diluted with water and the precipitated product was collected by filtration.

Yield: 17 mg MS (ES+) [M+H]: m/e=398/400 isotope pattern

Example 31: (5-methoxy-1-methylpyrazolo[3,4-b]indol-8(1H)-yl)(phenyl)methanone

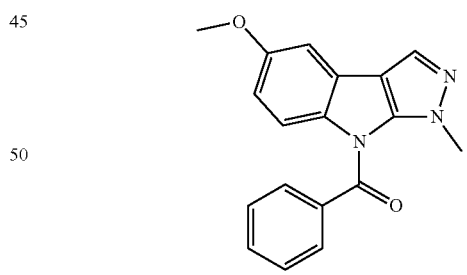

The title compound was prepared by adapting the procedure described in example 30 with the difference that 2-chloro-5-methoxy-indole-3-carbaldehyde was used instead of 1-(2-chloro-5-methoxy-1H-indol-3-yl)ethanone and benzoyl chloride was used instead of 2-bromobenzoyl chloride.

Yield: 15 mg MS (ES+) [M+H]: m/e=306

General Reaction to pyrazolo[3,4-b]indole-1,8-diyl-bis(phenylmethanone) Derivatives

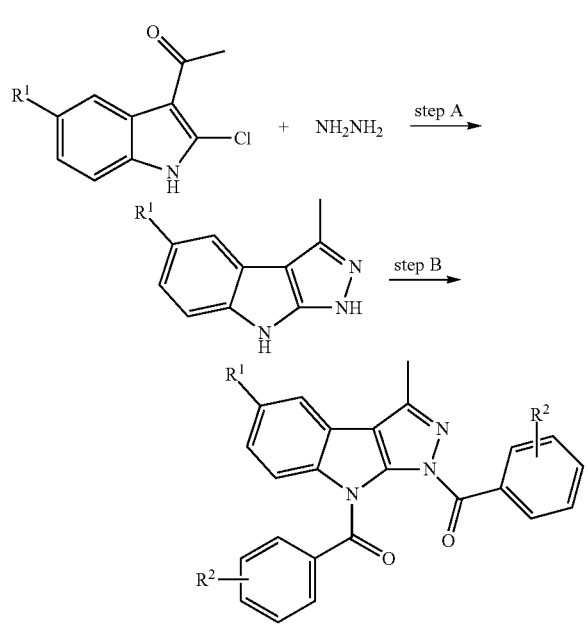

Example 32: (5-methoxy-3-methylpyrazolo[3,4-b]indole-1,8-diyl)bis((2-bromophenyl)methanone)

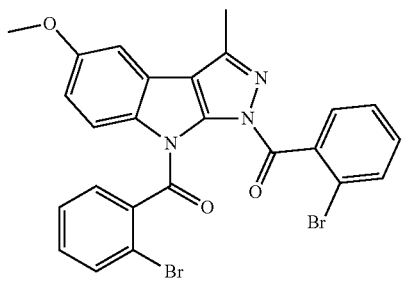 [SMILES: COc1ccc2c(c1)c1c(C)nn(C(=O)c3ccccc3Br)c1n2C(=O)c1ccccc1Br]

The title compound was prepared by dissolving 200 mg 1-(2-chloro-5-methoxy-1H-indol-3-yl)ethanone (0.90 mmol, 1.0 eq.) and 131 µl hydrazine hydrate in 2.7 ml ethanol. The solution was kept at reflux for 8 h. After complete reaction the mixture was cooled down and the precipitated product was collected by filtration. The solid compound was washed with ethanol to achieve pure 5-methoxy-3-methyl-1,8-dihydropyrazolo[3,4-b]indole. To a suspension of 20 mg 5-methoxy-3-methyl-1,8-dihydropyrazolo[3,4-b]indole (0.099 mmol, 1.0 eq.) in 2 ml ACN, sequentially 35 µl 2-bromobenzoyl chloride (0.30 mmol, 3.0 eq.), 36 mg DMAP (0.30 mmol, 3.0 eq.), and 41 µl TEA (0.30 mmol; 3.0 eq.) were added. The mixture was stirred for 6 hours at RT. Afterwards the reaction mixture was diluted with water and the precipitated product was collected by filtration and washed with ACN.

Yield: 30 mg MS (ES+) [M+H]: m/e=566/568/570 isotope pattern

Example 33: (5-methoxy-3-methylpyrazolo[3,4-b]indole-1,8-diyl)bis(phenylmethanone)

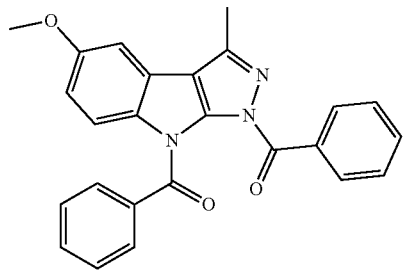 [SMILES: COc1ccc2c(c1)c1c(C)nn(C(=O)c3ccccc3)c1n2C(=O)c1ccccc1]

The title compound was prepared by adapting the procedure described in example 32 with the difference that benzoyl chloride was used instead of 2-bromobenzoyl chloride.

Yield: 13 mg MS (ES+) [M+H]: m/e=410

Example 34: (5-bromo-3-methylpyrazolo[3,4-b]indole-1,8-diyl)bis(phenylmethanone)

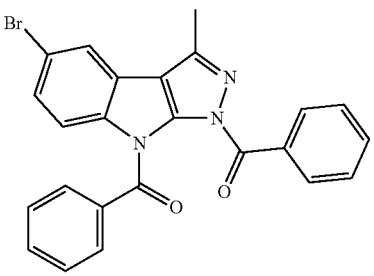 [SMILES: Cc1nn(C(=O)c2ccccc2)c2c1c1cc(Br)ccc1n2C(=O)c1ccccc1]

The title compound was prepared by adapting the procedure described in example 32 with the difference that 1-(5-bromo-2-chloro-1H-indol-3-yl)ethan-1-one was used instead of 1-(2-chloro-5-methoxy-1H-indol-3-yl)ethanone and benzoyl chloride was used instead of 2-bromobenzoyl chloride.

Yield: 5 mg MS (ES+) [M+H]: m/e=458 isotope pattern

Example 35: (5-bromo-3-methylpyrazolo[3,4-b]indole-1,8-diyl)bis((2-bromophenyl)methanone)

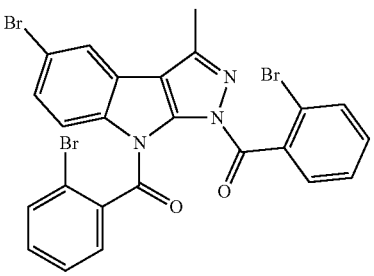 [SMILES: Cc1nn(C(=O)c2ccccc2Br)c2c1c1cc(Br)ccc1n2C(=O)c1ccccc1Br]

The title compound was prepared by adapting the procedure described in example 32 with the difference that 1-(5-bromo-2-chloro-1H-indol-3-yl)ethan-1-one was used instead of 1-(2-chloro-5-methoxy-1H-indol-3-yl).

Yield: 14 mg MS (ES+) [M+H]: m/e=616 isotope pattern

Example 36: (5-bromo-3-methylpyrazolo[3,4-b]indole-1,8-diyl)bis((4-methoxyphenyl)methanone)

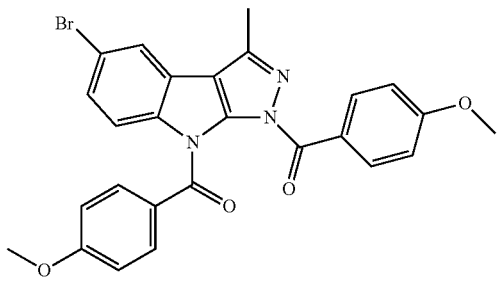

The title compound was prepared by adapting the procedure described in example 32 with the difference that 1-(5-bromo-2-chloro-1H-indol-3-yl)ethan-1-one was used instead of 1-(2-chloro-5-methoxy-1H-indol-3-yl) and 4-methoxybenzoyl chloride was used instead of 2-bromobenzoyl chloride.

Yield: 18 mg MS (ES+) [M+H]: m/e=518/520 isotope pattern

General Reaction to
5-benzyl-5H-pyrimido[5,4-b]indole Derivatives
(Example 37)

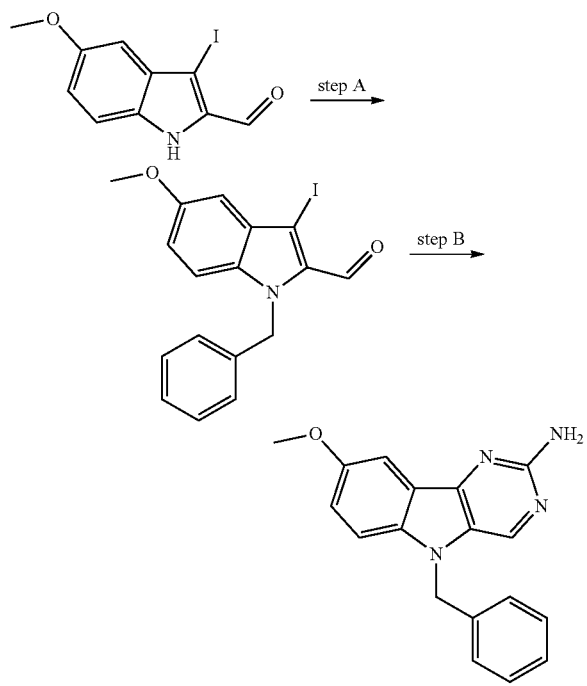

Example 37: 5-benzyl-8-methoxy-5H-pyrimido[5,4-b]indol-2-amine

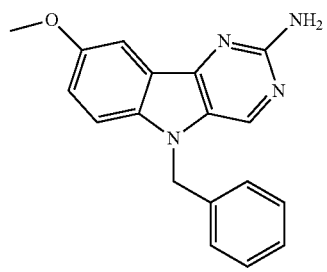 [SMILES: COc1ccc2c(c1)c1nc(N)ncc1n2Cc1ccccc1]

The title compound was prepared by adding a solution of 600 mg 5-methoxy-3-iodo-1H-indole-2-carbaldehyde (2.00 mmol, 1.0 eq.) in 4 ml dry DMF dropwise to a solution of 62.2 mg sodium hydride (60% in paraffin oil) (2.59 mmol, 1.3 eq.) in 4 ml dry DMF at 0° C. The mixture was stirred for 20 minutes at 0° C. and a solution of 946 μl benzyl bromide (7.97 mmol, 4.0 eq.) was added. The suspension was stirred for 1 h at room temperature and another 38.3 mg sodium hydride (60% in paraffin oil) (1.59 mmol, 0.8 eq.) and 473 μl benzyl bromide (3.99 mmol, 2.0 eq.). The mixture was further stirred at room temperature for 12 h. After complete reaction the mixture was quenched with iced water and extracted with EtOAc. The organic phase was washed with water and brine, dried over sodium sulfate, and the solvent was evaporated under reduced pressure. The crude product was purified by silica gel chromatography, with cyclohexane/EtOAc as solvent to achieve clean 1-benzyl-3-iodo-5-methoxy-1H-indole-2-carbaldehyde. Step B: A suspension of 300 mg 1-benzyl-3-iodo-5-methoxy-1H-indole-2-carbaldehyde (0.77 mmol, 1.0 eq.), 147 mg guanidine (1.53 mmol, 2.0 eq.), 500 mg cesium carbonate (1.53 mmol, 2.0 eq.), 14.6 mg copper(I) iodide (0.08 mmol, 0.1 eq.), and 1,10-phenanthroline in 2.5 ml dry DMSO was stirred for 48 h at 90° C. under nitrogen. After complete reaction water and EtOAc were added and the mixture was filtrated by a celite filter. The aqueous phase was extracted with EtOAc two times. The combined organic phases were washed with brine, dried over sodium sulfate, and the solvent was evaporated under reduced pressure. The crude product was purified by silica gel chromatography, with cyclohexane/EtOAc as solvent. The product was purified once more via preparative HPLC Method 3.

Yield: 36 mg MS (ES+) [M+H]: m/e=305

General Reaction to
5-benzyl-5H-pyrimido[5,4-b]indole Derivatives
(Example 38)

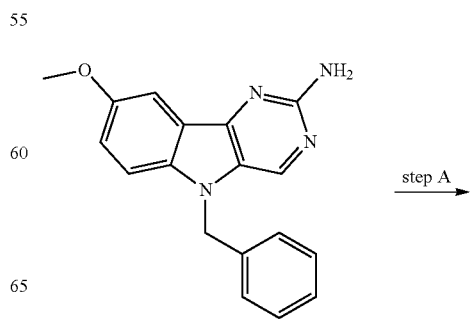

Example 38: 5-benzyl-2-chloro-8-methoxy-5H-pyrimido[5,4-b]indole

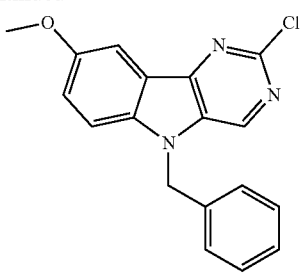

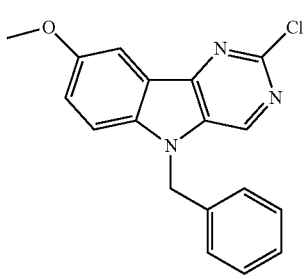 [SMILES: COc1ccc2c(c1)c1nc(Cl)ncc1n2Cc1ccccc1]

The title compound was prepared by dissolving 15 mg 5-benzyl-8-methoxy-5H-pyrimido[5,4-b]indol-2-amine (example 43) (0.05 mmol, 1.0 eq.) in 0.5 ml 1,2-dichloroethane. The solution was cooled down to −10° C. and a solution of 25 mg antimony trichloride (0.11 mmol, 2.2 eq.) in 0.1 ml 1,2-dichloroethane was added. Afterwards 27.7 µl tert-butylnitrite (0.23 mmol, 4.7 eq.) were added dropwise. The reaction mixture was stirred for 2 h at −10° C., next iced water was added. After complete reaction the mixture was extracted with EtOAc three times. The combined organic phases were washed with water once, dried over magnesium sulfate and the solvent was evaporated under reduced pressure. The product was purified o via preparative HPLC Method 1.

Yield: 16 mg MS (ES+) [M+H]: m/e=324

General Reaction to
5-benzyl-5H-pyrimido[5,4-b]indole Derivatives
(Example 39)

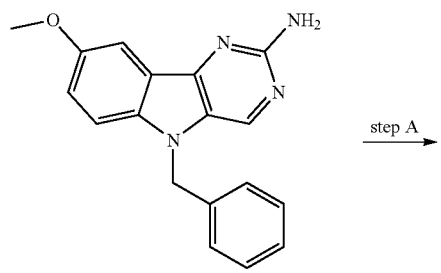

Example 39: 5-benzyl-8-methoxy-5H-pyrimido[5,4-b]indol-2-ol

The title compound was prepared by dissolving 15 mg 5-benzyl-8-methoxy-5H-pyrimido[5,4-b]indol-2-amine (example 43) (0.05 mmol, 1.0 eq.) in 0.2 ml acetic acid. The solution was cooled down to 10° C. and a solution of 10 mg sodium nitrite (0.15 mmol, 3.0 eq.) in 68 µl water was added. The reaction mixture was stirred for 30 min, next 1.5 ml water was added and the solution was stirred at 90° C. for 4 h.

After complete reaction the solvent was removed under vacuum and the residue was taken up with water and extracted with EtOAc three times. The combined organic phases were dried over sodium sulfate and the solvent was evaporated under reduced pressure.

Yield: 12 mg MS (ES+) [M+H]: m/e=306

General Reaction to
5-benzyl-5H-pyrimido[5,4-b]indole Derivatives
(Example 40)

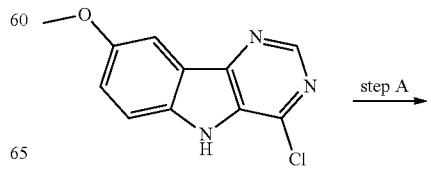

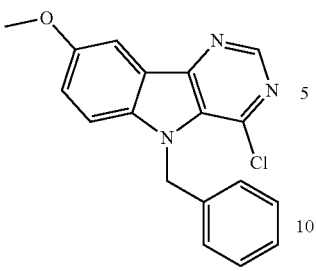

4-chloro-8-methoxy-5H-pyrimido[5,4-b]indole was obtained commercially

Example 40: 5-benzyl-4-chloro-8-methoxy-5H-pyrimido[5,4-b]indole

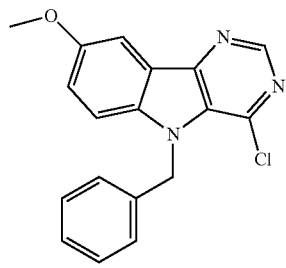 [SMILES: COc1ccc2c(c1)c1ncnc(Cl)c1n2Cc1ccccc1]

The title compound was prepared by dissolving 60 mg 4-chloro-8-methoxy-5H-pyrimido[5,4-b]indole (0.26 mmol, 1.0 eq.) in 4 ml DMF. To this solution 16 mg sodium hydride (60% in oil) (0.41 mmol, 1.6 eq.) and 3.1 mg DMAP (0.03 mmol, 0.1 eq.) were added. The mixture was stirred for around 20 minutes at RT and 53 mg (0.31 mmol, 1.2 eq.) benzyl bromide was added dropwise. After complete addition the reaction mixture was stirred for 18 h at 70° C.

After complete reaction the solvent was removed and the crude product was purified via preparative HPLC Method 1.

Yield: 11.6 mg MS (ES+) [M+H]: m/e=324

Example 41: 5-benzyl-8-methoxy-5H-pyrimido[5,4-b]indol-4-ol

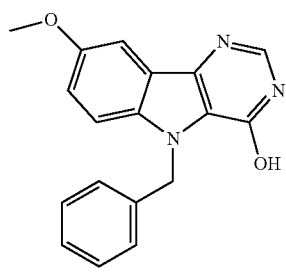 [SMILES: COc1ccc2c(c1)c1ncnc(O)c1n2Cc1ccccc1]

The title compound was obtained as a side product from the synthesis of example 40.

Yield: 14.8 mg MS(ES+) [M+H]: m/e=306

General Reaction to phenyl(5H-pyrimido[5,4-b]indol-5-yl)methanone Derivatives

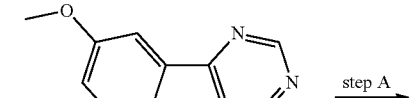

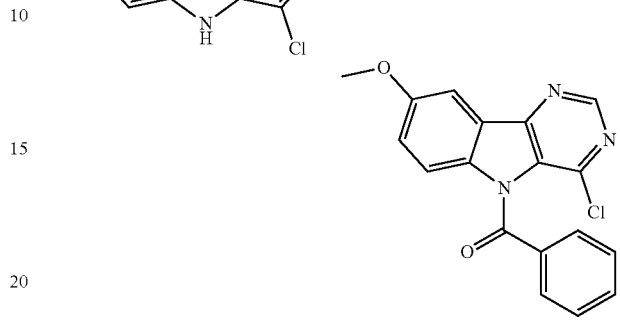

Example 42: (4-chloro-8-methoxy-5H-pyrimido[5,4-b]indol-5-yl)(phenyl)methanone

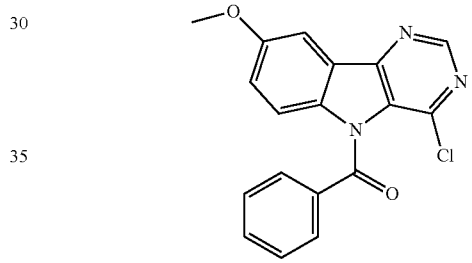

The title compound was prepared by adding to a suspension of 60 mg 4-chloro-8-methoxy-5H-pyrimido[5,4-b]indole (0.26 mmol, 1.0 eq.) in 5 ml ACN, sequentially 89 µl benzoyl chloride (0.77 mmol, 3.0 eq.), 94 mg DMAP (0.77 mmol, 3.0 eq.), and 107 µl TEA (0.7 mmol; 3.0 eq.). The mixture was stirred for 18 hours at RT and another 89 µl benzoyl chloride (0.77 mmol, 3.0 eq.) and 107 µl TEA (0.7 mmol; 3.0 eq.) were added. Afterwards the reaction mixture was diluted with water and the precipitate was removed. The filtrate was dried under vacuum and the crude product was purified by silica gel chromatography, with cyclohexane/ EtOAc as solvent.

Yield: 14.7 mg MS (ES+) [M+H]: m/e=338

General Reaction to 8H-dibenzo[b,f]pyrimido[4,5,6-hi]indolizin-8-one Derivatives

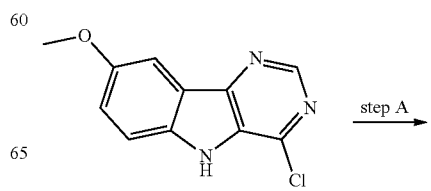

-continued

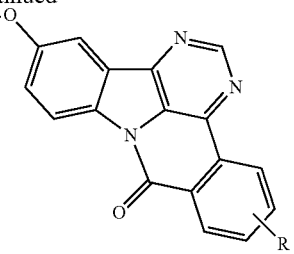

Example 43: 5,6,12-trimethoxy-8H-dibenzo[b,f]pyrimido[4,5,6-hi]indolizin-8-one

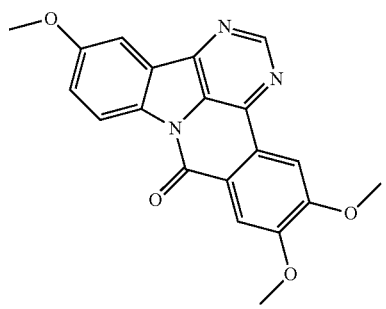

The title compound was prepared by dissolving 40 mg 4-chloro-8-methoxy-5H-pyrimido[5,4-b]indole (0.171 mmol, 1.0 eq.) and 88 mg bromotripyrrolidinophosphonium hexafluorophosphate (0.19 mmol, 1.1 eq.) under nitrogen in 1.4 ml 1,4-dioxane. To the solution 47 μl trimethylamine was added and the mixture was stirred for 2 h min at 70° C. Afterwards 27 mg 4,5-Dimethoxy-2-(methoxy carbonyl) benzeneboronic acid (0.18 mmol, 1.05 eq.), 6.0 mg bis (triphenylphosphine)palladium(II) dichloride (0.009 mmol, 0.05 eq.), 36 mg sodium carbonate (0.34 mmol, 2.0 eq.), and 0.7 ml water were added. The mixture was stirred at 70° C. for 18 h, a suspension is formed. After complete reaction, solid product was removed by filtration and washed with water and MeOH.

Yield: 41 mg MS (ES+) [M+H]: m/e=362

Example 44: 12-methoxy-8H-dibenzo[b,f]pyrimido[4,5,6-hi]indolizin-8-one

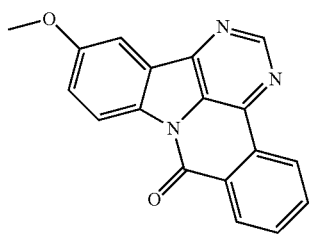 [SMILES: COc1ccc2c(c1)c1ncnc3c4ccccc4c(=O)n2c31]

The title compound was prepared by adapting the procedure described in example 43 with the difference that 2-methoxy carbonylphenylboronic acid was used instead of 4,5-Dimethoxy-2-(methoxy carbonyl)benzeneboronic acid.

Yield: 47 mg MS (ES+) [M+H]: m/e=302

General Reaction to Example 45 (MW01)

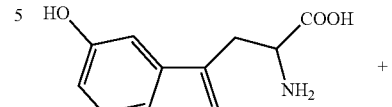

Example 45: 12-hydroxy-6,7-dimethoxy-8H-benzo[c]indolo[3,2,1-ij][1,5]naphthyridin-8-one

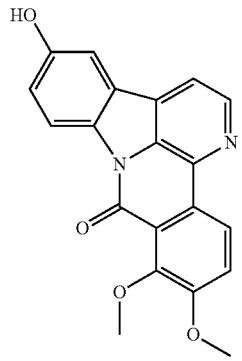 [SMILES: COc1ccc2c(c1OC)c(=O)n1c3ccc(O)cc3c3ccnc2c31]

The title compound was prepared by dissolving 2.00 g L-5-Hydroxytryptohan (9.1 mmol, 1.0 eq.) and 2.10 g 2-Carboxy-3,4-dimethoxybenzaldehyde (10 mmol, 1.1 eq.) in 9 ml glacial acetic acid. The mixture was kept under reflux for 6 h and another 18 h under reflux with a constant flow of air bubbling through the liquid. After complete reaction, solid product was removed by filtration and washed with water and acetic acid. The crude product was crystallized from DMF.

Yield: 1.18 g MS (ES+) [M+H]: m/e=347

Further examples of the present invention which can be prepared by using synthetic procedure well known to those skilled in the art and by adapting the general procedures described above are:

Example: 12-(2-(2-aminoethoxy)ethoxy)-6,7-dimethoxy-8H-benzo[c]indolo[3,2,1-ij][1,5]naphthyridin-8-one

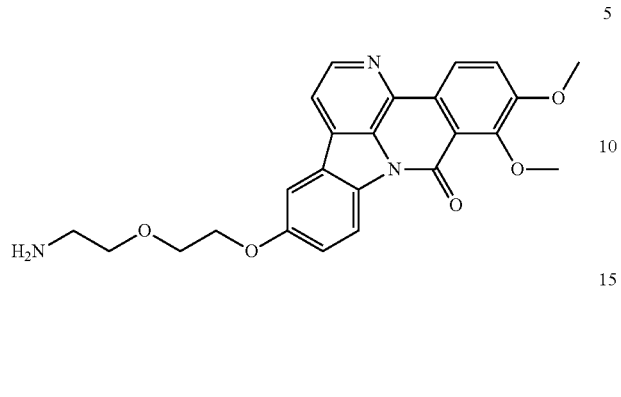

Example A1: 1-(4-chlorophenyl)-8H-benzo[c]indolo[3,2,1-ij][1,5]naphthyridin-8-one

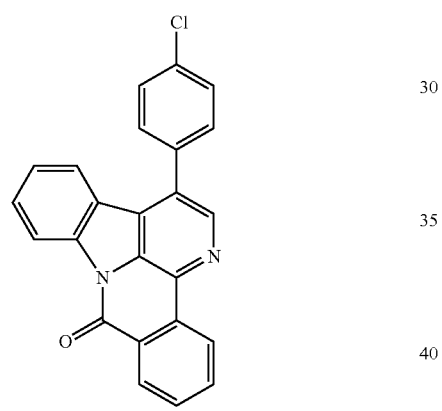

Example A2: 1-(2-chlorophenyl)-6,7-dimethoxy-8H-benzo[c]indolo[3,2,1-ij][1,5]naphthyridin-8-one

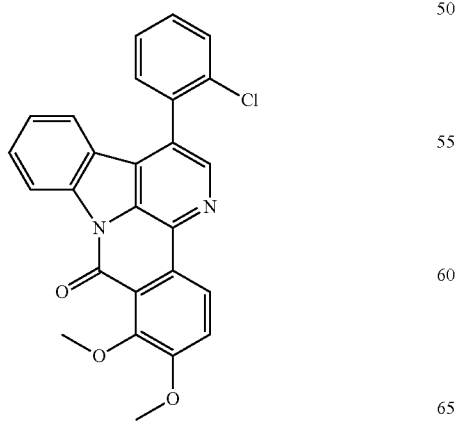

Example A3: 6,7-dimethoxy-1-(4-methoxyphenyl)-8H-benzo[c]indolo[3,2,1-ij][1,5]naphthyridin-8-one

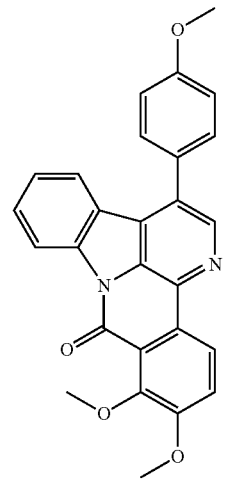 [SMILES: COc1ccc(-c2cnc3c4ccc(OC)c(OC)c4c(=O)n4c5ccccc5c2c34)cc1]

Example A4: methyl 6,7-dimethoxy-8-oxo-8H-benzo[c]indolo[3,2,1-ij][1,5]naphthyridine-2-carboxylate

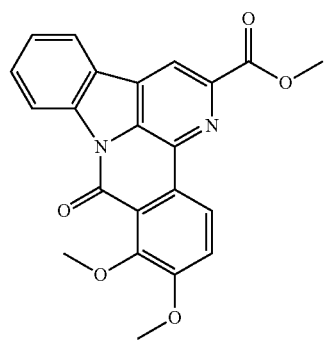 [SMILES: COC(=O)c1cc2c3ccccc3n3c(=O)c4c(OC)c(OC)ccc4c(n1)c23]

Example A5: 8-oxo-8H-benzo[c]indolo[3,2,1-ij][1,5]naphthyridine-2-carboxylic Acid

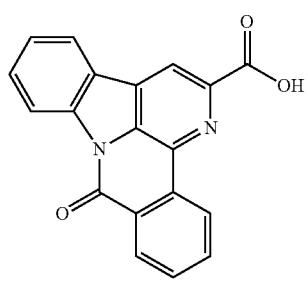 [SMILES: O=C(O)c1cc2c3ccccc3n3c(=O)c4ccccc4c(n1)c23]

Example A7: N-(3-methoxypropyl)-8-oxo-8H-benzo[c]indolo[3,2,1-ij][1,5]naphthyridine-2-carboxamide

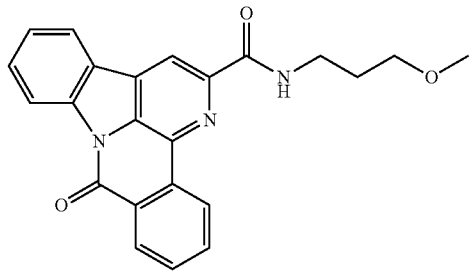 [SMILES: COCCCNC(=O)c1cc2c3ccccc3n3c(=O)c4ccccc4c(n1)c23]

Example A8: N-isopropyl-8-oxo-8H-benzo[c]indolo[3,2,1-ij][1,5]naphthyridine-2-carboxamide

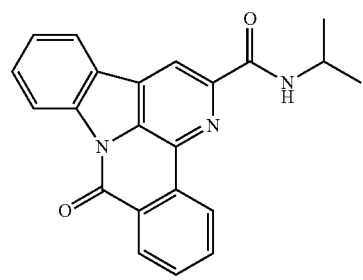 [SMILES: CC(C)NC(=O)c1cc2c3ccccc3n3c(=O)c4ccccc4c(n1)c23]

Example B1: 2-(4-methylpiperazine-1-carbonyl)-8H-benzo[c]indolo[3,2,1-ij][1,5]naphthyridin-8-one

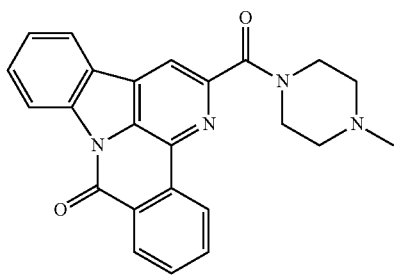 [SMILES: CN1CCN(C(=O)c2cc3c4ccccc4n4c(=O)c5ccccc5c(n2)c34)CC1]

Example B2: 13-((diethylamino)methyl)-12-hydroxy-8H-benzo[c]indolo[3,2,1-ij][1,5]naphthyridin-8-one

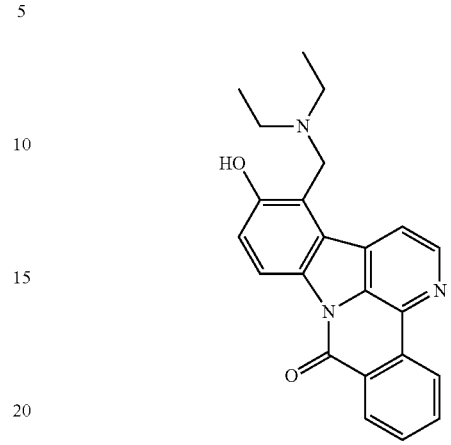

Example B3: 2-((6,7-dimethoxy-8-oxo-8H-benzo[c]indolo[3,2,1-ij][1,5]naphthyridin-12-yl)oxy)-N-(2-morpholinoethyl)acetamide

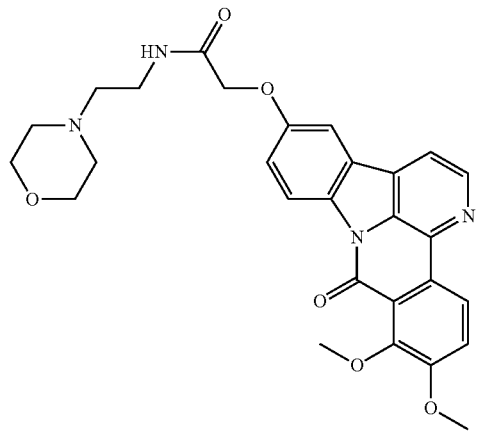 [SMILES: COc1ccc2c(c1OC)c(=O)n1c3ccc(OCC(=O)NCCN4CCOCC4)cc3c3ccnc2c31]

Example B4: 12-butoxy-8H-benzo[c]indolo[3,2,1-ij][1,5]naphthyridin-8-one

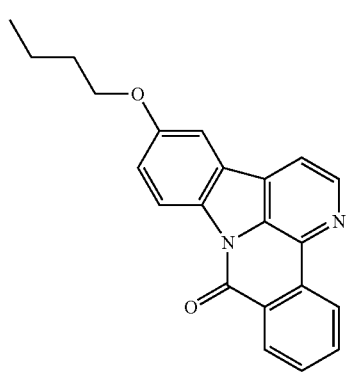 [SMILES: CCCCOc1ccc2c(c1)c1ccnc3c4ccccc4c(=O)n2c13]

Example B5: 12-ethoxy-6,7-dimethoxy-8H-benzo[c]indolo[3,2,1-ij][1,5]naphthyridin-8-one

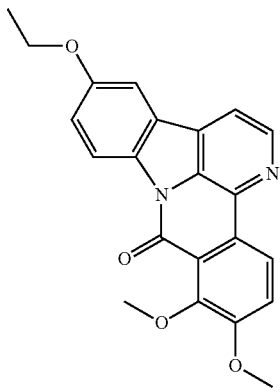 [SMILES: CCOc1ccc2c(c1)c1ccnc3c4ccc(OC)c(OC)c4c(=O)n2c13]

Example B6: 6,7-dimethoxy-8-oxo-N-pentyl-8H-benzo[c]indolo[3,2,1-ij][1,5]naphthyridine-2-carboxamide

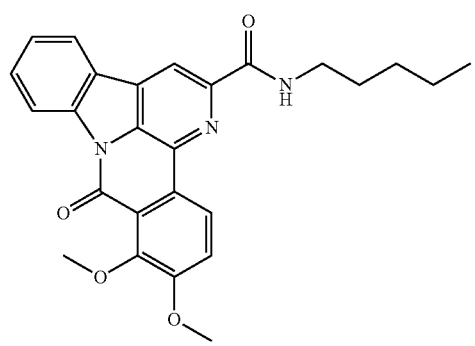 [SMILES: CCCCCNC(=O)c1cc2c3ccccc3n3c(=O)c4c(OC)c(OC)ccc4c(n1)c23]

Example B7: 6,7-dimethoxy-12-propoxy-8H-benzo[c]indolo[3,2,1-ij][1,5]naphthyridin-8-one

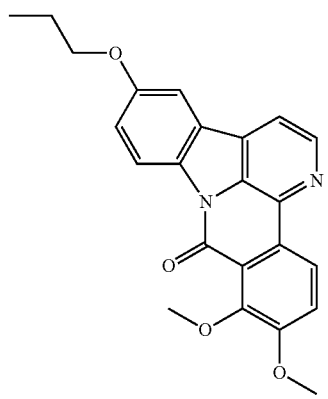 [SMILES: CCCOc1ccc2c(c1)c1ccnc3c4ccc(OC)c(OC)c4c(=O)n2c13]

Example B8: 6,7-dimethoxy-2-(4-methylpiperazine-1-carbonyl)-8H-benzo[c]indolo[3,2,1-ij][1,5]naphthyridin-8-one

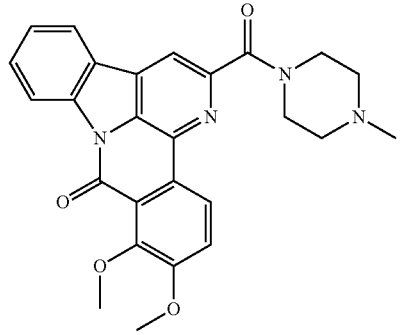 [SMILES: COc1ccc2c(c1OC)c(=O)n1c3ccccc3c3cc(C(=O)N4CCN(C)CC4)nc2c31]

Example C1: 6,7,11-trimethoxy-8H-benzo[c]indolo[3,2,1-ij][1,5]naphthyridin-8-one

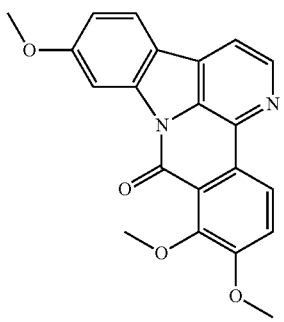

Example C2: 12-fluoro-6,7-dimethoxy-8H-benzo[c]indolo[3,2,1-ij][1,5]naphthyridin-8-one

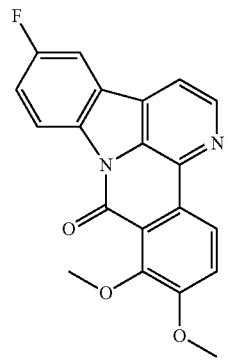 [SMILES: COc1ccc2c(c1OC)c(=O)n1c3ccc(F)cc3c3ccnc2c31]

Example C3: 12-methyl-8H-benzo[c]indolo[3,2,1-ij][1,5]naphthyridin-8-one

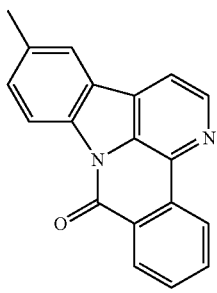 [SMILES: Cc1ccc2c(c1)c1ccnc3c4ccccc4c(=O)n2c13]

Example C4: 12-chloro-8H-benzo[c]indolo[3,2,1-ij][1,5]naphthyridin-8-one

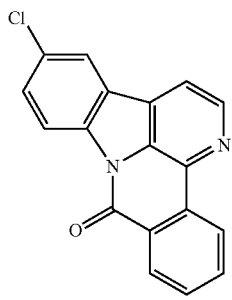 [SMILES: O=c1c2ccccc2c2nccc3c4cc(Cl)ccc4n1c32]

Example C5: 13-allyl-12-methoxy-8H-benzo[c]indolo[3,2,1-ij][1,5]naphthyridin-8-one

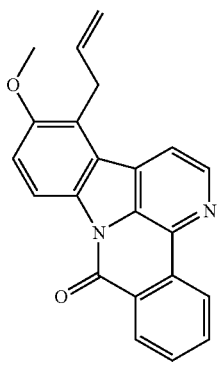 [SMILES: C=CCc1c(OC)ccc2c1c1ccnc3c4ccccc4c(=O)n2c13]

REFERENCES

Baud, V. & Karin, M. Is NF-kappaB a good target for cancer therapy? Hopes and pitfalls. Nat Rev Drug Discov 8, 33-40, (2009).

Christian, F., Smith, E. L. & Carmody, R. J. The Regulation of NF-kappaB Subunits by Phosphorylation. Cells 5, (2016).

Gibson, B. A. & Kraus, W. L. New insights into the molecular and cellular functions of poly(ADP-ribose) and PARPs. Nat Rev Mol Cell Biol 13, 411-424, (2012).

Hanahan, D. & Weinberg, R. A. Hallmarks of cancer: the next generation. Cell 144, 646-674, (2011).

Hayden, M. S. & Ghosh, S. Shared principles in NF-kappaB signaling. Cell 132, 344-362, (2008).

Hayden, M. S. & Ghosh, S. NF-kappaB, the first quarter-century: remarkable progress and outstanding questions. Genes Dev 26, 203-234, (2012).

Hinz, M., Stilmann, M., Arslan, S. C., Khanna, K. K., Dittmar, G. & Scheidereit, C. A cytoplasmic ATM-TRAF6-cIAP1 module links nuclear DNA damage signaling to ubiquitin-mediated NF-kappaB activation. Mol Cell 40, 63-74, (2010).

Hinz, M., Arslan, S. C. & Scheidereit, C. It takes two to tango: IkappaBs, the multifunctional partners of NF-kappaB. Immunol Rev 246, 59-76, (2012).

Hinz, M. & Scheidereit, C. The IkappaB kinase complex in NF-kappaB regulation and beyond. EMBO Rep 15, 46-61, (2014).

Kucharczak, J., Simmons, M. J., Fan, Y. & Gelinas, C. To be, or not to be: NF-kappaB is the answer-role of Rel/NF-kappaB in the regulation of apoptosis. Oncogene 22, 8961-8982, (2003).

Lim, K. H., Yang, Y. & Staudt, L. M. Pathogenetic importance and therapeutic implications of NF-kappaB in lymphoid malignancies. Immunol Rev 246, 359-378, (2012).

Mullard, A. European regulators approve first PARP inhibitor. Nat Rev Drug Discov 13, 877-877, (2014).

Scheidereit, C. (1998) Signal transduction: Docking IkappaB kinases. Nature 395, 225-226

Scheidereit, C. IkappaB kinase complexes: gateways to NF-kappaB activation and transcription. Oncogene 25, 6685-6705, (2006).

Shiloh, Y. & Ziv, Y. The ATM protein kinase: regulating the cellular response to genotoxic stress, and more. Nat Rev Mol Cell Biol 14, 197-210, (2013).

Stilmann, M., Hinz, M., Arslan, S. C., Zimmer, A., Schreiber, V. & Scheidereit, C. A nuclear poly(ADP-ribose)-dependent signalosome confers DNA damage-induced IkappaB kinase activation. Mol Cell 36, 365-378, (2009).

Sun, S. C. The noncanonical NF-kappaB pathway. Immunol Rev 246, 125-140, (2012).

Wu, C. J., Conze, D. B., Li, T., Srinivasula, S. M. & Ashwell, J. D. Sensing of Lys 63-linked polyubiquitination by NEMO is a key event in NF-kappaB activation [corrected]. Nat Cell Biol 8, 398-406, (2006).

Wu, Z., Wang, C., Bai, M., Li, X., Mei, Q., Li, X., Wang, Y., Fu, X., Luo, G., & Han, W. (2015) An LRP16-containing preassembly complex contributes to NF-κB activation induced by DNA double-strand breaks. Nucleic Acids Res. 43(6):3167-79

Zhang, J., Clark, K., Lawrence, T., Peggie, M. W. & Cohen, P. An unexpected twist to the activation of IKKbeta: TAK1 primes IKKbeta for activation by autophosphorylation. Biochem J 461, 531-537, (2014).

The invention claimed is:

1. A method of treatment of a cancer in a subject in need thereof comprising:
   (a) identifying the subject as having a cancer exhibiting genotoxic stress-induced IKK/NF-κB signaling activation that causes growth of the cancer,
   (b) selectively blocking activation of IKK/NF-κB in response to the genotoxic stress upstream of the IKK complex in the subject without blocking NF-κB activation upon signaling caused by other pathways in the subject by administering to the subject a compound according to Formula I,

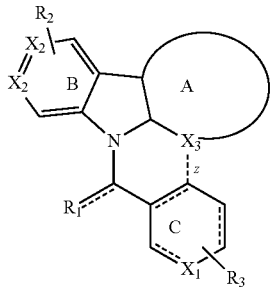

Formula I wherein
R1=H, O;
R2=from 0-4, can be the same or different, H, OH, halogen, C1-C7 alkyl, alkenyl, alkynyl, alkoxy, carbonyl, carboxyl, alkoxycarbonyl, amine, or wherein R2 is alkoxyamine, alkoxyamide;
R3=from 0-4, can be the same or different, H, OH, halogen, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms;
X1 and X2=N or C;
X3=C;
ring A is an aromatic cyclic structure of 5 or 6 members, optionally comprising 0, 1, or 2 heteroatoms selected from the group consisting of O and N,
wherein said cyclic structure is optionally substituted with 0-3 substituents that can be the same or different, selected from the group consisting of H, OH, halogen, C1-C7 alkyl, alkenyl, alkynyl, alkoxy, carbonyl, alkoxycarbonyl, amine, aryl, (optionally substituted with halogen, C1-C3 alkyl, alkoxy, amine) and alkoxyamine;
the bond z may be present or not present, wherein when bond z is not present:
the C of bond z of ring C is potentially substituted with R3, and X3 of the A ring is optionally substituted with H, OH, halogen, C1-C7 alkyl, alkenyl, alkynyl, alkoxy, carbonyl, carboxyl, alkoxycarbonyl, amine.

2. The method according to claim 1, wherein the compound is, according to Formula II,

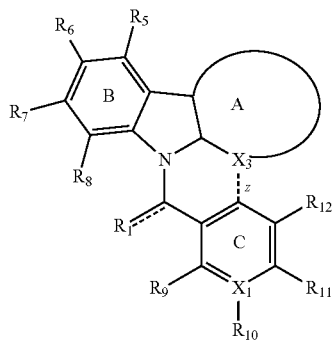

Formula II wherein
R1=H, O;
R5=H, halogen, C1-C5, alkyl, alkenyl, alkoxy, amine;
R6=H, OH, halogen, C1-C5, alkyl, alkoxy, or alkoxyamine, alkoxyamide;
R7=H, halogen, C1-C5, alkyl, or alkoxy;
R8=H, halogen, C1-C5, alkyl or alkoxy;
R9=H, halogen, C1-C5, alkyl or alkoxy;
R10=H, halogen, C1-C5, alkyl or alkoxy;
R11=H, halogen, C1-C5, alkyl, alkoxy, or carboxyl;
R12=H, halogen, C1-C5, alkyl or alkoxy;
or wherein when X1 is C, R9 and R10, R10 and R11, R11 and R12, or R12 and the C in the position of bond z of ring C, form an optionally aromatic cyclic structure of 5 or 6 members, comprising 0, 1, or 2 heteroatoms or forming phenyl;
X1=N or C;
X3=C;
ring A is an aromatic cyclic structure of 5 or 6 members, comprising 0, 1, or 2 heteroatoms selected from the group consisting of 0 and N, wherein said cyclic structure is optionally substituted with 0-3 substituents that can be the same or different, selected from the group consisting of H, OH, halogen, C1-C7 alkyl, alkenyl, alkynyl, alkoxy, carbonyl, carboxyl, alkoxycarbonyl, amine, aryl, (optionally substituted with halogen, C1-C3 alkyl, alkoxy, amine), and alkoxyamine;
the bond z may be present or not present, wherein when bond z is not present:
the C in the position of bond z of ring C is substituted with halogen, preferably Cl, Br, F, C1-C7, alkyl, and X3 of the A ring is optionally substituted with H, C1-C5, alkyl, or when X3 is C with H, C1-C5, alkyl, OH, halogen.

3. The method according to claim 1, wherein R1=0.

4. The method according to claim 1, wherein at least one of R2 from 0-4 is not H.

5. The method according to claim 1, wherein ring A is a heteroaromatic cyclic structure of 6 members, comprising 1 or 2 heteroatoms selected from 0 and/or N.

6. The method according to claim 1, wherein ring A is selected from the group consisting of

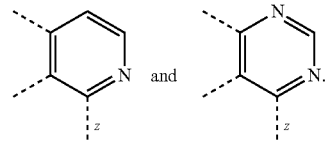

7. Compound according to Formula I,

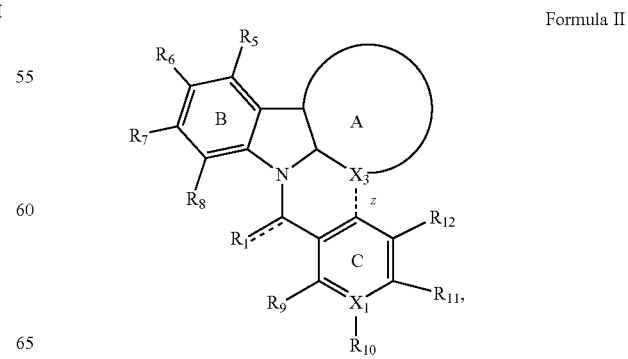

Formula II wherein:
R1=O;
R5=H, halogen, C1-C5 alkyl or alkoxy, or amine;
R6=H, OH, halogen, C1-C5 alkyl or alkoxy;
R7=H, halogen, C1-C5 alkyl or alkoxy;
R8=halogen, C1-C5 alkyl or alkoxy,
wherein at least one of R5 to R8 is not H;
R9=H, halogen, or C1-C5 alkyl or alkoxy;
R10=H, halogen, or C1-C5 alkyl or alkoxy;
R11=H, halogen, C1-C5 alkyl, alkoxy or carbonyl;
R12=H, halogen, or C1-C5 alkyl or alkoxy;
or wherein when X1 is C, R9 and R10, R10 and R11, R11 and R12, or R12 and the C in the position of bond z of ring C, form an optionally aromatic cyclic structure of 5 or 6 members, comprising 0, 1, or 2 heteroatoms or forming phenyl;
X1=N or C;
X3=C;
ring A is a heteroaromatic cyclic structure of 6 members, comprising 1 or 2 heteroatoms selected from 0 and/or N,
wherein said cyclic structure is optionally substituted with 0-3 substituents that can be the same or different, selected from the group consisting of H, OH, halogen, C1-C7 alkyl, alkenyl, alkynyl, alkoxy, carbonyl, carboxyl, alkoxycarbonyl, amine, aryl and alkoxyamine;
the bond z may be present or not present, wherein when bond z is not present; and
the C in the position of bond z of ring C is substituted with halogen or C1-C5 alkyl, or X3 of the A ring is optionally substituted with H, C1-C5 alkyl, OH or halogen.

8. Compound according to claim 7, wherein the compound is of Formula III,

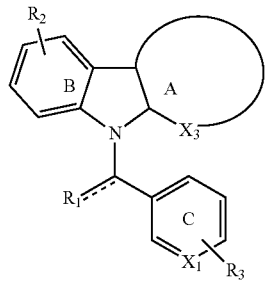

Formula III wherein
R1=O;
R2=from 0-4, can be the same or different, H, OH, halogen, C1-C7 alkyl, alkenyl, alkynyl, alkoxy, carbonyl, alkoxycarbonyl, amine, or wherein R2 is alkoxyamine or alkoxyamide, wherein at least one of R2 from 0-4 is not H;
R3=from 0-4, can be the same or different, H, OH, halogen, C1-C7 alkyl, alkenyl, alkynyl, alkoxy, carbonyl, carboxyl, alkoxycarbonyl, amine, or wherein two (adjacent) R3 substituents form an optionally aromatic cyclic structure of 5 or 6 members, optionally comprising 0, 1, or 2 heteroatoms or forming phenyl;
X1=N or C;
X3=C;
ring A is a heteroaromatic structure of 6 members, comprising 1 or 2 N atom, wherein said cyclic structure is optionally substituted with 0-3 substituents that can be the same or different, selected from the group consisting of H, OH, halogen, C1-C7 alkyl, alkenyl, alkynyl, alkoxy, carbonyl, carboxyl, alkoxycarbonyl, amine, aryl (optionally substituted with halogen, C1-C3 alkyl, alkoxy, amine), alkoxyamine, or wherein ring A is a heteroaromatic structure selected from the group consisting of:
and

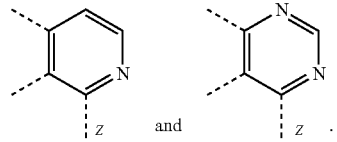

9. Compound according to claim 7, wherein the compound is of Formula VIII,

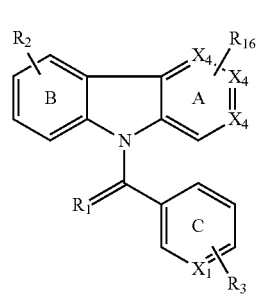

Formula VIII wherein
R1=O;
R2=from 0-4, can be the same or different, H, OH, halogen, C1-C7 alkyl, alkenyl, alkynyl, alkoxy, carbonyl, carboxyl, alkoxycarbonyl, amine, or wherein R2 is alkoxyamine, alkoxyamide, wherein at least one of R2 from 0-4 is not H;
R3=from 0-4, can be the same or different, H, OH, halogen, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms or form phenyl;
X1=N or C;
X4=N or C, whereby at least one X4 is N;
R16=can be 0-3, the same or different, H, halogen, C1-C5 alkoxy.

10. Compound according to claim 7, wherein the compound is of Formula IX,

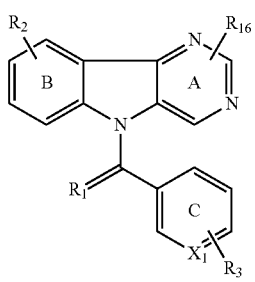

Formula IX wherein
R1=O;
R2=from 0-4, can be the same or different, H, OH, halogen, C1-C7 alkyl, alkenyl, alkynyl, alkoxy, carbonyl, carboxyl, alkoxycarbonyl, amine, or wherein R2 is alkoxyamine, alkoxyamide, wherein at least one of R2 from 0-4 is not H;
R3=from 0-4, can be the same or different, H, OH, halogen C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms or form phenyl;
X1=N or C;
R16=can be 0-3, the same or different, H, halogen, C1-C5, alkyl or alkoxy.

11. Compound according to claim 7, wherein the compound is of Formula X,

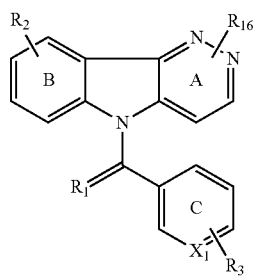

Formula X wherein
R1=O;
R2=from 0-4, can be the same or different, H, OH, halogen, C1-C7 alkyl, alkenyl, alkynyl, alkoxy, carbonyl, carboxyl, alkoxycarbonyl, amine, or wherein R2 is alkoxyamine, alkoxyamide, wherein at least one of R2 from 0-4 is not H;
R3=from 0-4, can be the same or different, H, OH, halogen C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms or form phenyl;
X1=N or C;
R16=can be 0-3, the same or different, H, halogen, C1-C5 alkyl, alkoxy or methoxy.

12. Compound according to claim 7, wherein the compound is of Formula VI,

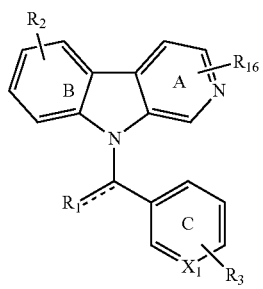

Formula VI wherein
R1=O;
R2=from 0-4, can be the same or different, H, OH, halogen, C1-C7 alkyl, alkenyl, alkynyl, alkoxy, carbonyl, carboxyl, alkoxycarbonyl, amine, or wherein R2 is alkoxyamine, alkoxyamide, wherein at least one of R2 from 0-4 is not H;
R3=from 0-4, preferably 0, 1, 2, can be the same or different, H, OH, halogen, C1-C7 alkyl, alkenyl, alkynyl, alkoxy, carbonyl, carboxyl, alkoxycarbonyl, amine, or wherein two (adjacent) R3 substituents can form an optionally aromatic cyclic structure of 5 or 6 members, optionally comprising 0, 1, or 2 heteroatoms or form phenyl;
X1=N or C;
R16=can be 0-3, the same or different, H, halogen, C1-C5 alkoxy.

13. The method according to claim 1, wherein the compound is

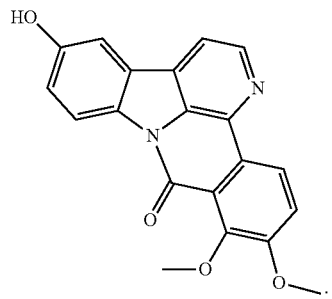 [SMILES: COc1ccc2c(c1OC)c(=O)n1c3ccc(O)cc3c3ccnc2c31]

14. The method according to claim 1, wherein the compound is more effective in inhibiting NF-κB-signaling induced by genotoxic stress compared to inhibiting NF-κB-signaling induced by TNF-alpha and/or IL-1 ß.

15. The method according to claim 1, wherein the disease is associated with genomic instability due to defective DNA-repair mechanisms.

16. The method according to claim 1, wherein said cancer is associated with NF-κB-mediated resistance to therapy-induced tumor cell apoptosis.

17. The method according to claim 1, wherein the compound is administered in combination with one or more genotoxic stress-inducing (DNA damage-inducing) cancer therapies.

18. In vitro method for the inhibition of genotoxic stress-induced NF-κB signaling or inhibition of DNA repair mechanisms comprising the use of a compound according to claim 1.

19. The method of claim 1, wherein the genotoxic stress-induced IKK/NF-κB signaling pathway is activated by a factor selected from the group consisting of a pro-inflammatory cytokine, PAMPS (pathogen associated molecular patterns), engagement of immune receptors and γ-irradiation (γ-IR).

* * * * *